United States Patent
Lo et al.

(10) Patent No.: US 9,645,010 B2
(45) Date of Patent: May 9, 2017

(54) FLUIDIC FLOW CYTOMETRY DEVICES AND METHODS

(75) Inventors: Yu-Hwa Lo, San Diego, CA (US);
Sung Hwan Cho, La Jolla, CA (US);
Jose Morachis, San Diego, CA (US);
Will Alaynick, San Diego, CA (US);
Kendall Chuang, San Diego, CA (US);
Nam Kim, San Diego, CA (US)

(73) Assignees: The Regents Of The University Of California, Oakland, CA (US);
NanoCellect Biomedical, Inc., San Diego, CA (US)

( * ) Notice: Subject to any disclaimer, the term of this patent is extended or adjusted under 35 U.S.C. 154(b) by 0 days.

(21) Appl. No.: 13/593,488

(22) Filed: Aug. 23, 2012

(65) Prior Publication Data

US 2013/0083315 A1 Apr. 4, 2013

Related U.S. Application Data

(63) Continuation-in-part of application No. 13/254,851, filed as application No. PCT/US2010/026884 on Mar. 10, 2010, now Pat. No. 9,134,221.

(Continued)

(51) Int. Cl.
*G01N 21/00* (2006.01)
*G01J 3/46* (2006.01)
(Continued)

(52) U.S. Cl.
CPC . *G01J 3/46* (2013.01); *G01J 3/28* (2013.01); *G01J 3/51* (2013.01); *G01N 15/1434* (2013.01);
(Continued)

(58) Field of Classification Search
CPC ........ G01N 21/53; G01N 15/02; G01N 21/64; G01N 21/00; G01N 33/48; G01N 1/10;
(Continued)

(56) References Cited

U.S. PATENT DOCUMENTS 3,790,760 A 2/1974 Stiller
3,984,307 A 10/1976 Kamentsky et al.
(Continued)

FOREIGN PATENT DOCUMENTS

EP 2351832 A1 8/2011
EP 2671065 A1 12/2013
(Continued)

OTHER PUBLICATIONS

"Microfluidic cell sorter with integrated piezoelectric actuator", Aug. 1, 2009, Biomed Microdevices (11:1223-1231) by Chun H. Chen et al.*

(Continued)

*Primary Examiner* — Tarifur Chowdhury
*Assistant Examiner* — Jamil Ahmed
(74) *Attorney, Agent, or Firm* — Perkins Coie LLP

(57) ABSTRACT

Devices, systems and methods facilitate analyzing, identifying and sorting particles in fluids, including cytometry devices and techniques. The described techniques can be used in a variety of applications such as in chemical or biological testing and diagnostic measurements. One exemplary flow cytometry device includes a channel that is capable of conducting a fluid containing at least one particle and also capable of allowing light be transmitted to and from the channel. The flow cytometry device also includes a lens that is positioned between the channel and a color filter. The lens directs at least a portion of light transmitted from the channel to the color filter. The color filter includes a plurality of zones, where each zone is adapted to allow transmission (Continued)

of only a particular spectral range of light. The flow cytometry device further includes a detector configured to receive the light that is transmitted through the color filter.

17 Claims, 43 Drawing Sheets

Related U.S. Application Data

(60) Provisional application No. 61/158,969, filed on Mar. 10, 2009, provisional application No. 61/262,787, filed on Nov. 19, 2009.

(51) Int. Cl.
| | |
|---|---|
| *G01J 3/51* | (2006.01) |
| *G01J 3/28* | (2006.01) |
| *G01P 5/26* | (2006.01) |
| *G01N 15/00* | (2006.01) |
| *G01N 15/14* | (2006.01) |

(52) U.S. Cl.
CPC ............ *G01N 15/1459* (2013.01); *G01P 5/26* (2013.01); *G01N 2015/0065* (2013.01); *G01N 2015/144* (2013.01); *G01N 2015/149* (2013.01)

(58) Field of Classification Search
CPC ...... G01N 21/55; G01N 30/00; G01N 33/533; G21K 5/04; H03M 13/00
USPC ........... 356/39, 246, 301, 335, 337, 417, 73; 422/73; 435/5, 29, 287.2; 250/492.1
See application file for complete search history.

(56) References Cited

U.S. PATENT DOCUMENTS

| | | | |
|---|---|---|---|
| 5,917,733 A | 6/1999 | Bangham | |
| 6,049,381 A | 4/2000 | Reintjes et al. | |
| 6,744,038 B2 | 6/2004 | Wang et al. | |
| 6,778,724 B2 | 8/2004 | Wang et al. | |
| 6,784,420 B2 | 8/2004 | Wang et al. | |
| 6,815,664 B2 | 11/2004 | Wang et al. | |
| 6,833,542 B2 | 12/2004 | Wang et al. | |
| 6,909,824 B1 | 6/2005 | Messica et al. | |
| 6,936,811 B2 | 8/2005 | Kibar | |
| 7,068,874 B2 | 6/2006 | Wang et al. | |
| 7,157,271 B2 | 1/2007 | Ryu et al. | |
| 7,160,687 B1 * | 1/2007 | Kapur .................. B01L 3/5027 356/300 | |
| 7,245,379 B2 | 7/2007 | Schwabe | |
| 7,298,478 B2 | 11/2007 | Gilbert et al. | |
| 7,355,699 B2 | 4/2008 | Gilbert et al. | |
| 7,492,522 B2 | 2/2009 | Gilbert et al. | |
| 7,576,861 B2 | 8/2009 | Gilbert et al. | |
| 7,701,580 B2 | 4/2010 | Bassler et al. | |
| 7,745,221 B2 | 6/2010 | Butler et al. | |
| 7,746,466 B2 | 6/2010 | Godin et al. | |
| 7,767,444 B2 | 8/2010 | Liu et al. | |
| 7,870,964 B2 | 1/2011 | Gilbert et al. | |
| 8,026,054 B2 | 9/2011 | Sharma et al. | |
| 8,277,764 B2 | 10/2012 | Gilbert et al. | |
| 8,373,860 B2 | 2/2013 | Kiesel et al. | |
| 8,426,209 B2 | 4/2013 | Butler et al. | |
| 8,629,981 B2 | 1/2014 | Martini et al. | |
| 8,691,164 B2 | 4/2014 | Butler et al. | |
| 8,822,207 B2 | 9/2014 | Foster et al. | |
| 8,993,311 B2 | 3/2015 | Foster et al. | |
| 9,011,797 B2 | 4/2015 | Gilbert et al. | |
| 9,134,221 B2 | 9/2015 | Lo et al. | |
| 2002/0011097 A1 * | 1/2002 | Kuderer et al. ............. 73/61.57 | |
| 2002/0108859 A1 | 8/2002 | Wang et al. | |
| 2002/0113204 A1 | 8/2002 | Wang et al. | |
| 2002/0115163 A1 | 8/2002 | Wang et al. | |
| 2002/0121443 A1 | 9/2002 | O'Connell | |
| 2002/0122167 A1 | 9/2002 | Riley et al. | |
| 2002/0123112 A1 | 9/2002 | Wang et al. | |
| 2002/0137059 A1 | 9/2002 | Wu et al. | |
| 2002/0160470 A1 | 10/2002 | Zhang | |
| 2003/0124516 A1 | 7/2003 | Chung et al. | |
| 2003/0137666 A1 * | 7/2003 | Johnson ........................ 356/417 |
| 2003/0159999 A1 | 8/2003 | Oakey et al. | |
| 2003/0194755 A1 | 10/2003 | Schnabel et al. | |
| 2003/0211461 A1 | 11/2003 | Kariv et al. | |
| 2003/0215791 A1 * | 11/2003 | Garini et al. ..................... 435/5 |
| 2004/0009540 A1 | 1/2004 | Soohoo et al. | |
| 2004/0023310 A1 | 2/2004 | Kariv et al. | |
| 2004/0033539 A1 | 2/2004 | Schnabel et al. | |
| 2004/0053209 A1 | 3/2004 | Kariv et al. | |
| 2004/0072278 A1 | 4/2004 | Chou et al. | |
| 2004/0161772 A1 | 8/2004 | Bohm et al. | |
| 2005/0036139 A1 * | 2/2005 | Johnson ........................ 356/246 |
| 2005/0105077 A1 * | 5/2005 | Padmanabhan et al. ........ 356/39 |
| 2005/0112541 A1 | 5/2005 | Durack et al. | |
| 2005/0164372 A1 | 7/2005 | Kibar | |
| 2006/0060767 A1 | 3/2006 | Wang et al. | |
| 2006/0066837 A1 * | 3/2006 | Ortyn et al. ..................... 356/73 |
| 2006/0117563 A1 | 6/2006 | Sugahara | |
| 2006/0192955 A1 * | 8/2006 | Jorgenson et al. ........... 356/301 |
| 2006/0197033 A1 | 9/2006 | Hairston et al. | |
| 2006/0282752 A1 * | 12/2006 | Kuroda ............... G06F 12/0215 714/785 |
| 2007/0086918 A1 * | 4/2007 | Hartley et al. ................... 422/73 |
| 2007/0117086 A1 | 5/2007 | Evans et al. | |
| 2007/0140638 A1 | 6/2007 | Yang et al. | |
| 2007/0159627 A1 * | 7/2007 | Johnson ........................ 356/335 |
| 2008/0233635 A1 * | 9/2008 | Evans et al. ............... 435/287.2 |
| 2008/0302732 A1 | 12/2008 | Soh et al. | |
| 2009/0027666 A1 | 1/2009 | Godin et al. | |
| 2009/0042737 A1 | 2/2009 | Katz et al. | |
| 2009/0155832 A1 * | 6/2009 | Lo et al. ......................... 435/29 |
| 2009/0190121 A1 | 7/2009 | Hegyi et al. | |
| 2009/0194705 A1 | 8/2009 | Kiesel et al. | |
| 2009/0195773 A1 * | 8/2009 | Bassler et al. .................. 356/73 |
| 2010/0018310 A1 | 1/2010 | Mutharasan et al. | |
| 2010/0051828 A1 * | 3/2010 | Doemer et al. ............. 250/492.1 |
| 2010/0108577 A1 | 5/2010 | Wang et al. | |
| 2010/0117007 A1 | 5/2010 | Kibar | |
| 2010/0155572 A1 | 6/2010 | Kiesel et al. | |
| 2011/0039258 A1 | 2/2011 | McNeeley et al. | |
| 2011/0086769 A1 | 4/2011 | Oliphant et al. | |
| 2011/0196637 A1 | 8/2011 | Sharpe et al. | |
| 2012/0009619 A1 | 1/2012 | Gilbert et al. | |
| 2012/0012508 A1 | 1/2012 | Deshpande et al. | |
| 2012/0045763 A1 | 2/2012 | Sharma et al. | |
| 2012/0077191 A1 | 3/2012 | Gunning et al. | |
| 2012/0078531 A1 | 3/2012 | Lo et al. | |
| 2012/0138513 A1 | 6/2012 | Johnson et al. | |
| 2012/0190105 A1 | 7/2012 | Foster et al. | |
| 2012/0202237 A1 | 8/2012 | Sedoglavich et al. | |
| 2012/0255373 A1 | 10/2012 | Foster et al. | |
| 2012/0261013 A1 | 10/2012 | Gilbert et al. | |
| 2012/0277902 A1 | 11/2012 | Sharpe et al. | |
| 2012/0307244 A1 | 12/2012 | Sharpe et al. | |
| 2013/0016335 A1 | 1/2013 | Lo et al. | |
| 2013/0171683 A1 | 7/2013 | Durack et al. | |
| 2013/0313170 A1 | 11/2013 | Bohm et al. | |
| 2013/0334407 A1 | 12/2013 | Perrault, Jr. et al. | |
| 2014/0251879 A1 | 9/2014 | Deshpande et al. | |
| 2015/0211979 A1 | 7/2015 | Lo et al. | |

FOREIGN PATENT DOCUMENTS

| | | |
|---|---|---|
| EP | 2872887 A1 | 1/2014 |
| WO | 94/05775 A1 | 3/1994 |
| WO | WO-02059577 | 8/2002 |
| WO | 2007/051170 A2 | 5/2007 |
| WO | 2010/104993 A2 | 9/2010 |
| WO | 2012083250 A2 | 6/2012 |
| WO | 2012106645 A1 | 8/2012 |
| WO | 2012154614 A1 | 11/2012 |

(56) References Cited

FOREIGN PATENT DOCUMENTS

WO    2013010134 A2    1/2013
WO    2013192342 A1    12/2013

OTHER PUBLICATIONS

Chen, C., et al., "Microfluidic cell sorter with integrated piezoelectric actuator," Biomedical Microdevices, 11 (6):1223-1231, Aug. 2009.

Cho, S., et al., "Micro-fabricated Fluorescence-Activated Cell Sorter," Annual International Conference of the IEEE Engineering in Medicine and Biology Society, pp. 1075-1078, Sep. 3-6, 2009.

Cho, S., et al., "Microfluidic Photonic Integrated Circuits," Optoelectronic Materials and Devices, vol. 7135, pp. 1-17, Jan. 2008.

Cho, S., et al., "Optofluidic Waveguides in Teflon AF-Coated PDMS Microfluidic Channels," IEEE Photonics Technology Letters, 21(15)1057-1059, Aug. 1, 2009.

Fu, A.Y., et al., A Microfabricated Fluorescence-Activated Cell Sorter, Nature Biotechnology, vol. 17, pp. 1109-1111, Nov. 1999.

Godin, J., et al., "Microfluidics and photonics for Bio-System-on-a-Chip: A review of advancements in technology towards a microfluidic flow cytometry chip," Journal of Biophotonics, 1(5):355-376, Oct. 2008.

International Search Report and Written Opinion mailed on Nov. 1, 2007 for International Application No. PCT/US2006/060313, filed Oct. 27, 2006 (4 pages).

International Search Report and Written Opinion mailed on Oct. 26, 2010 for International Application No. PCT/US2010/026884, filed Mar. 10, 2010 (10 pages).

Lee, G.-B., et al., "Micro Flow Cytometers with Buried SU-8/SOG Optical Waveguides," Sensors and Actuators A: Physical, 103(1):165-170, Jan. 2003.

Lien, V., et al., "High-Sensitivity Cytometric Detection Using Fluidic-Photonic Integrated Circuits with Array Waveguides," IEEE Journal of Selected Topics in Quantum Electronics, 11(4):827-834, Jul./Aug. 2005.

Lien, V., et al., "Microfluidic-photonic-dielectrophoretic integrated circuits for biophotonic sensing," The 17th Annual Meeting of the IEEE Lasers and Electro-Optics Society, vol. 2, pp. 533-534, Nov. 2004.

Tung, Y.-C., et al., "PDMS-based opto-fluidic micro flow cytometer with two-color, multi-angle fluorescence detection capability using PIN photodiodes," Sensors and Actuators B, 98(2-3):356-367, Mar. 2004.

Lien, V., et al., "A Prealigned Process of Integrating Optical Waveguides With Microfluidic Devices," IEEE Photonics Technology Letters, 16(6):1525-1527, Jun. 2004.

Lien, V., et al., "Fluidic Photonic Integrated Circuit for In-Line Detection," Applied Physics Letters, 87(19):194106(1-3), Nov. 2005.

Zhang, H., et al., "Time-of-Flight Optophoresis Analysis of Live Whole Cells in Microfluidic Channels," Biomedical Microdevices, 6(1):11-21, Mar. 2004.

\* cited by examiner

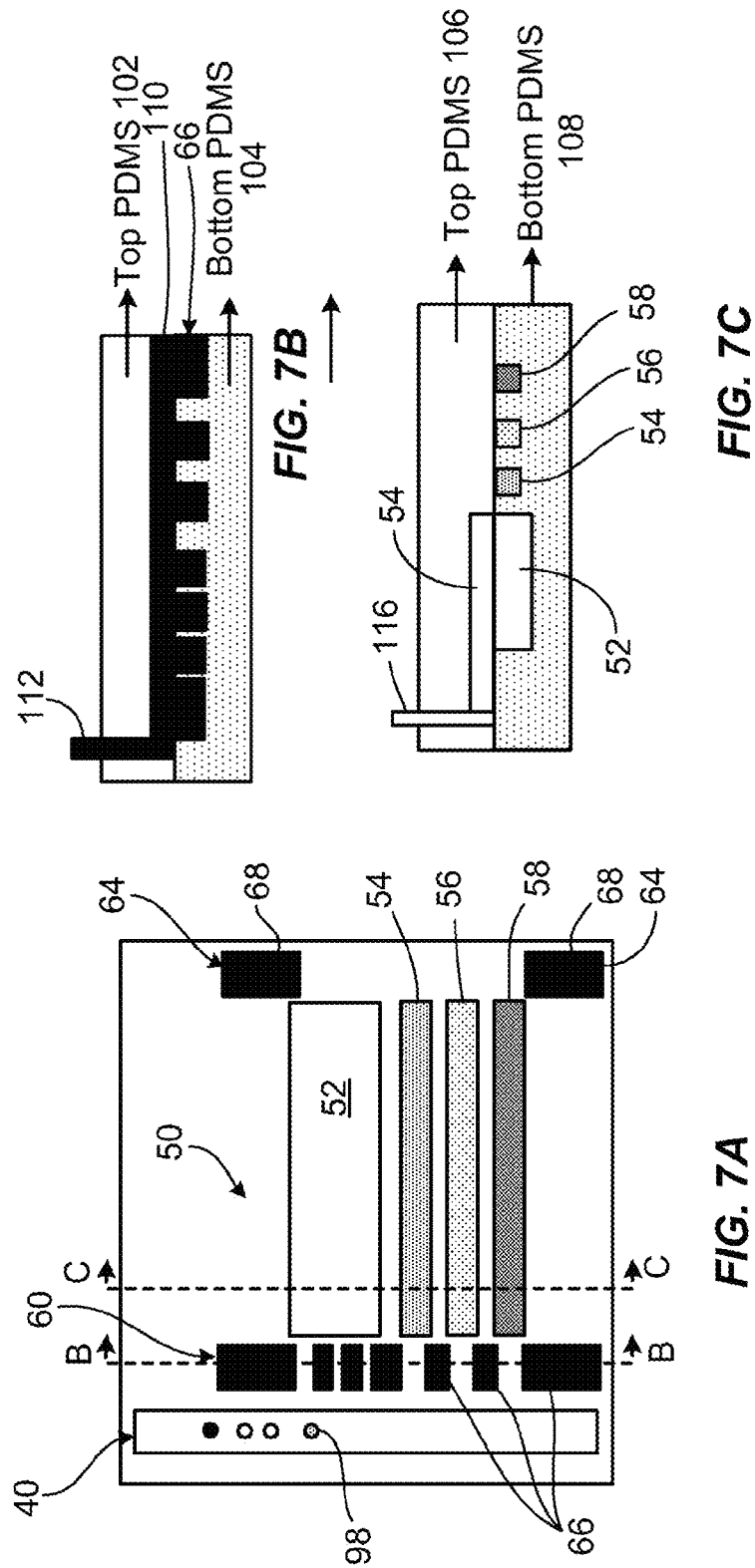

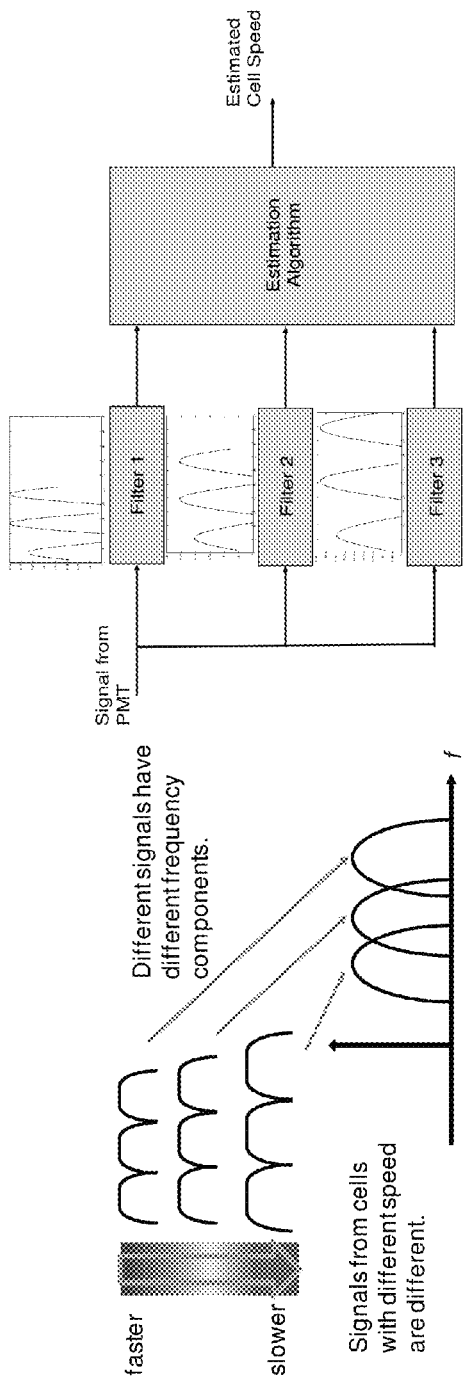
FIG. 12A
FIG. 12B
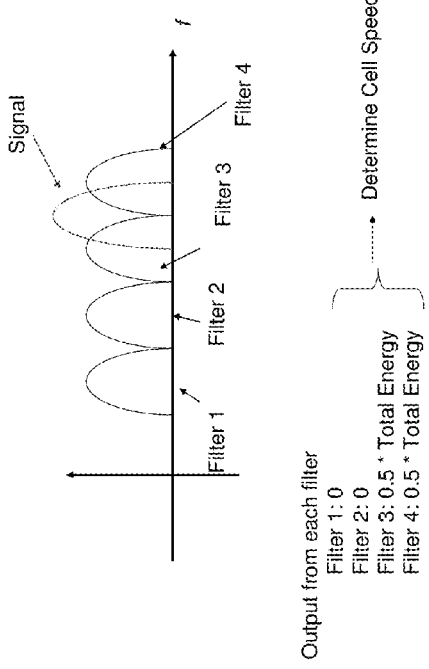
FIG. 12C

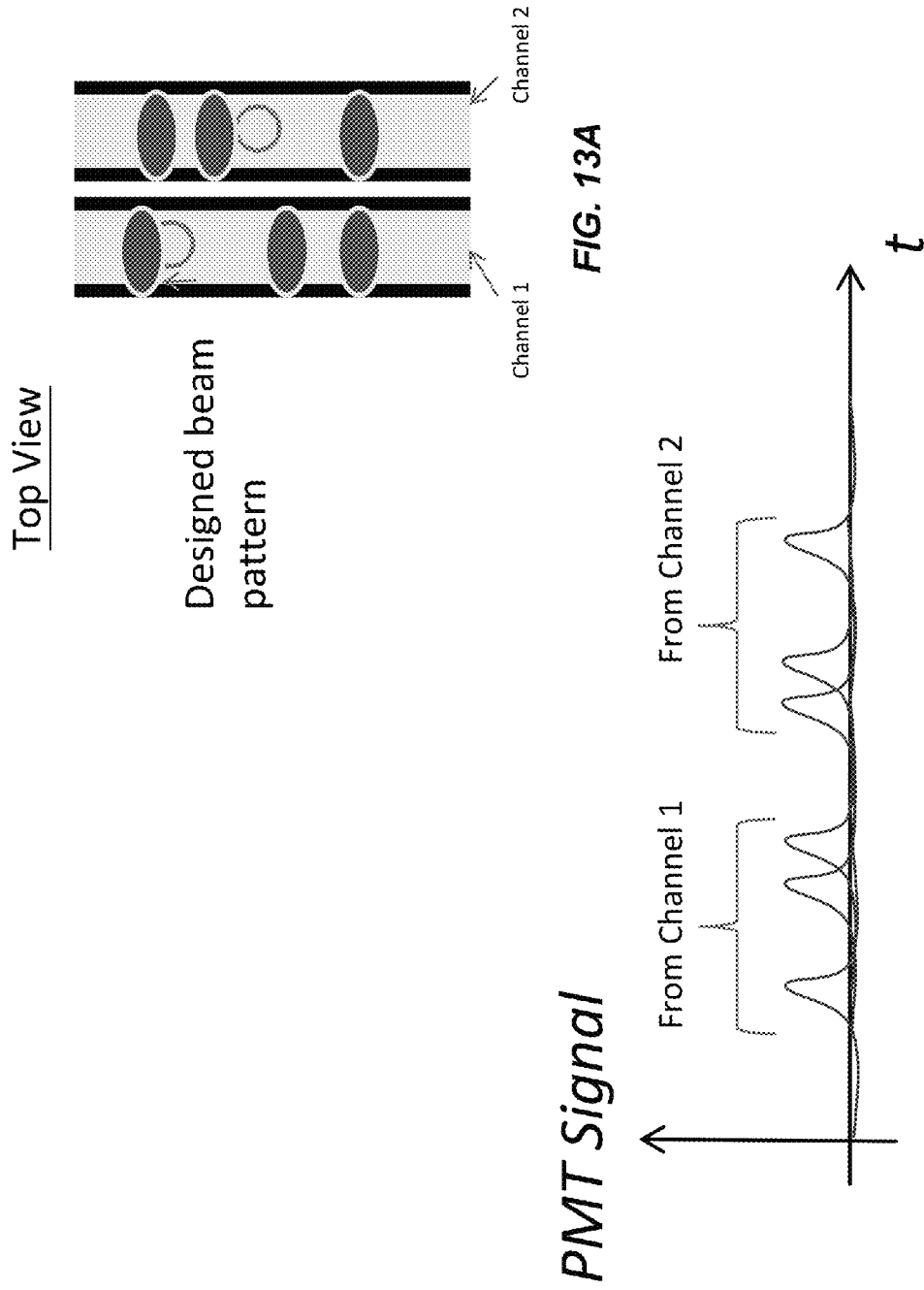

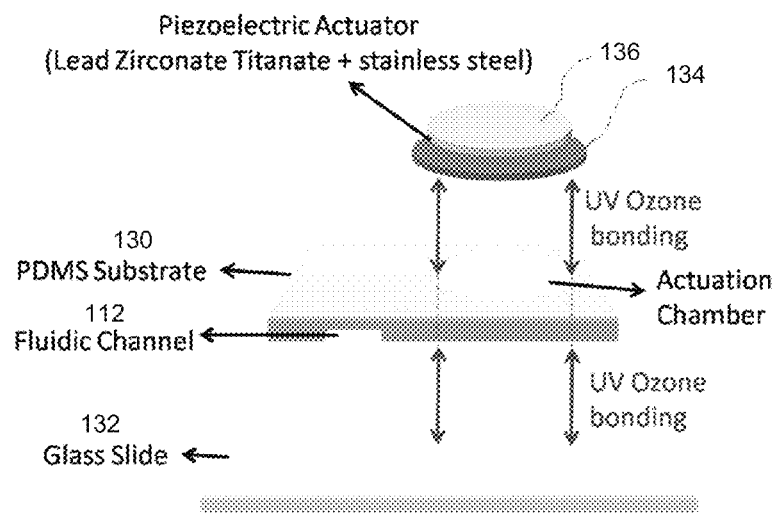
*FIG. 17A*
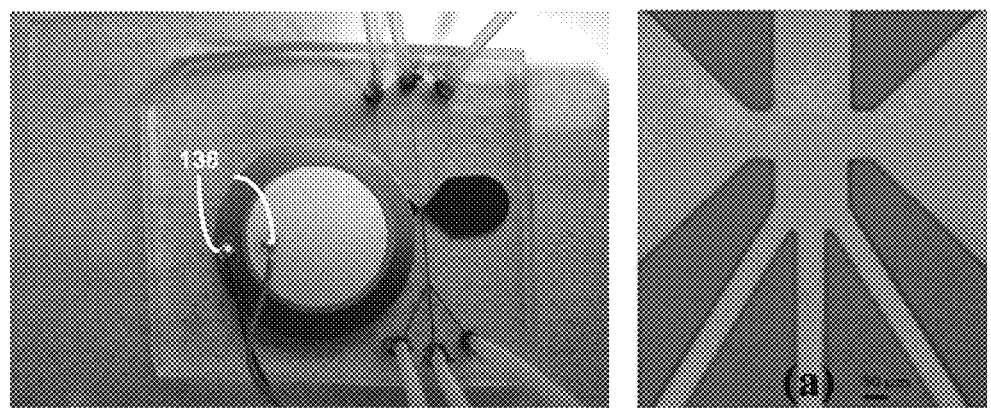
*FIG. 17B*  *FIG. 17C*

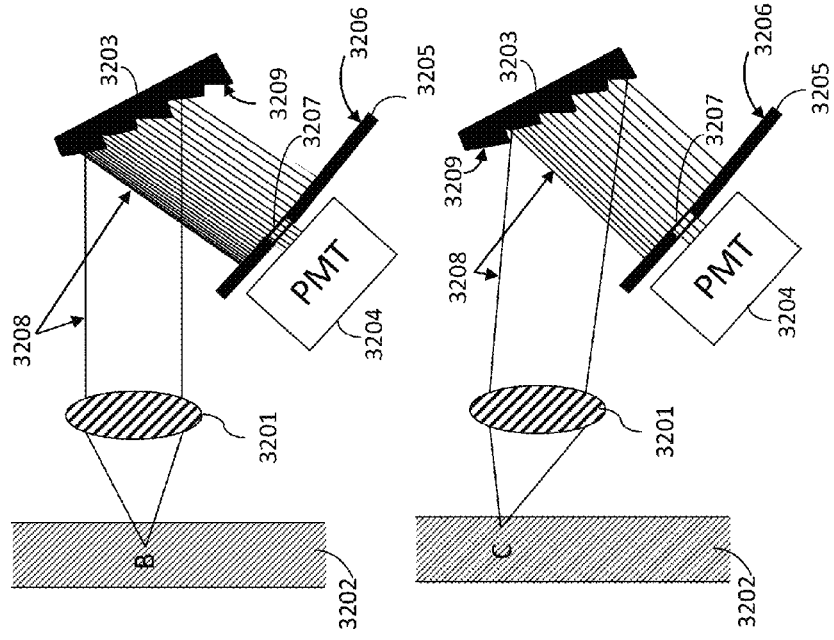
FIG. 32B
FIG. 32C
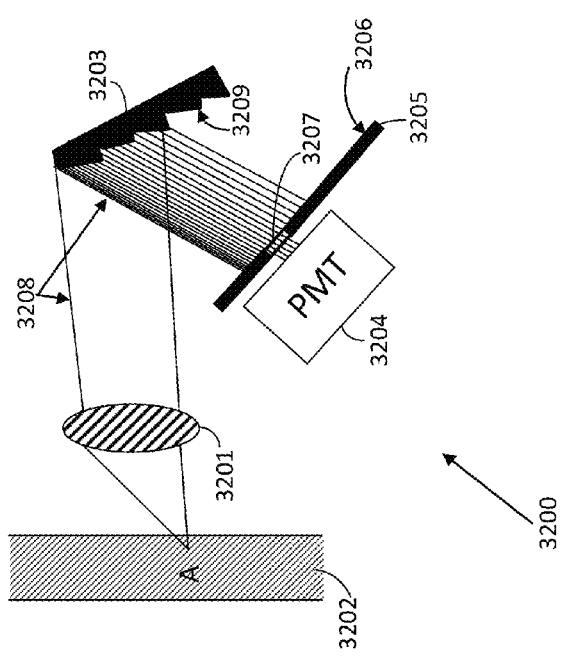
FIG. 32A

FLUIDIC FLOW CYTOMETRY DEVICES AND METHODS

CROSS REFERENCE TO RELATED PATENT APPLICATIONS

This application is a continuation-in-part of U.S. patent application Ser. No. 13/254,851, filed on Sep. 4, 2011, which is a U.S. National Stage application under 35 U.S.C. §371 of International Application No. PCT/US2010/026884, filed on Mar. 10, 2010, which claims benefit of priority of U.S. Provisional Application No. 61/158,969, filed on Mar. 10, 2009, and U.S. Provisional Application No. 61/262,787, filed on Nov. 19, 2009. The entire contents of the before-mentioned patent applications are incorporated by reference as part of the disclosure of this application.

STATEMENT REGARDING FEDERALLY SPONSORED RESEARCH OR DEVELOPMENT

The invention was made with government support under grant nos. HG004876, RR024453, R43RR031424, and R43RR032225 awarded by National Institutes of Health (NIH). The government has certain rights in the invention.

BACKGROUND

This patent document relates to fluidic devices and techniques in connection with particle sorting in fluid, including cytometry devices and techniques and applications in chemical or biological testing and diagnostic measurements.

Flow cytometry (FC) devices and systems can be used to characterize and analyze particles in fluid, e.g., physical and biochemical properties of cells and biochemical molecules or molecule clusters based on their optical responses as they are interrogated by external light sources in a serial manner. Optical signals from such particles can be collected by an optical detector, such as a photomultiplier tube (PMT), and are analyzed or processed to extract information carried by the optical properties of the particles. The optical signals from the particles can be caused by one or more interactions between the input light and the particles such as forward scattering (FSC), side scattering (SSC), and fluorescence.

Particle sorting, and in particular cell sorting (including cell sorting at the single-cell level) has become an essential feature in the field of flow cytometry as researchers and clinicians become more interested in studying and purifying certain cells such as stem cells, circulating tumor cells, and rare bacteria species. Cell sorting can be achieved by various techniques. One example is applying vibrations to the jet flow from the nozzle to cause breakage of jet flow into droplets and subsequently using electrically charged plates to deflect cell-containing droplets into their respective collection tubes (droplets of no interest flow straight down to the waste tube without deflection).

Flow cytometry (FC) devices and systems can be implemented based on microfluidic technologies for research assays and diagnostics as well as for clinical applications. Microfluidic technologies range from simple microfluidic channels to complex microfludic devices that can mix fluids, pump fluids, perform digital logic, individually culture cells, determine optimal reaction conditions, and much more. Small-scale fluidic devices have low Reynolds numbers and can be used to achieve controlled laminar flow systems. Microfluidics further offer the advantages of small size for miniaturization and parallelization of devices. The compact size of microfludic devices opens the door to the potential of portable devices. Additionally, various fabrication processes for microfludic devices are suitable for mass production which can reduce the cost of such devices. Advances in microfludic devices can lead to low-cost lab-on-a-chip devices, useful tools to researchers, clinical laboratories, and point-of-care clinicians in remote and/or resource-poor settings.

SUMMARY

This document describes, among others, examples and implementations of techniques and devices for analyzing, identifying and sorting particles in fluid, including cytometry devices and techniques.

On aspect of the disclosed embodiments relates to a flow cytometry device that comprises a channel capable of conducting a fluid containing at least one particle, where the channel is further capable of allowing light be transmitted to and from the channel. The flow cytometry device also includes a lens positioned between the channel and a color filter and adapted to direct at least a portion of light transmitted from the channel to the color filter, where the color filter comprises a plurality of zones, and each zone is adapted to allow transmission of only a particular spectral range of light. The flow cytometry further includes a detector configured to receive the light that is transmitted through the color filter.

In one exemplary embodiment, the flow cytometry device further comprises at least one light source positioned to direct light to the mirror, and one or more mirrors positioned to reflect the light from the light source(s) into the channel, where the one or more mirrors are substantially transparent to the light transmitted by the channel. In this exemplary embodiment, the flow cytometry device also includes an optical filter positioned between the lens and the detector and adapted to substantially block the light from the light source and to substantially transmit the light transmitted from the channel into the color filter.

According to one exemplary embodiment, at least one of the one or more mirrors is positioned between one of: the lens and the detector, and the lens and the channel. In another exemplary embodiment, at least one of the one or more mirrors is configured to block about 20% or less of the light transmitted by the channel, whereas in another example embodiment, at least one of the one or more mirrors is configured to block about 5% or less of the light transmitted by the channel. In yet another exemplary embodiment, the flow cytometry device further includes an additional lens positioned between the color filter and the detector. In still another exemplary embodiment, each zone allows transmission of a spectral range of light that is non-overlapping with spectral ranges allowed to be transmitted by all other zones. According to one example embodiment, at least one zone is adapted to allow transmission of a spectral range of light that is overlapping with transmission spectral range of at least one other zone. In another exemplary embodiment, the zones are continuously graded in the color filter.

Another aspect of the disclosed embodiments relates to a flow cytometry device that includes a fluidic channel capable of conducting a fluid containing at least one particle, where the channel is further capable of allowing light be transmitted to and from the fluidic channel. The above noted flow cytometry devices further includes a lens positioned between the fluidic channel and a diffractive component, where the lens is adapted to direct at least a portion of light transmitted from the fluidic channel to the diffractive component. Such a flow cytometry device additionally includes an aperture positioned between the diffractive component and a detector, where the aperture is adapted to allow a particular spectral range of light received from the diffractive component to reach the detector based upon the position(s) of the at least one particle within the fluidic channel.

In one exemplary embodiment, a first spectral range of light is received at the detector when the at least one particle is at a first position within the fluidic channel and a second spectral range of light is received at the detector when the at least one particle is at a second position within the fluidic channel. In another exemplary embodiment, the refractive component is a photodiffractive component that consists of one or more of a diffraction grating and a prism.

Another aspect of the disclosed embodiments relates to an imaging device that includes a stage configured to move in one or more dimensions and configured to receive an object for imaging, where at least a portion of the object is capable of transmitting light. The imaging device further includes a lens positioned between the stage and an image sensor and adapted to direct the light emitted by the at least a portion of the object to the image sensor. The image sensor of the imaging device comprises a plurality of light sensing elements arranged as a plurality of sensing element subsets, where each sensing element subset is responsive to a particular spectral range of light incident thereupon. The image sensor of the imaging device is aligned with the lens and the object so as to receive, at a first subset of the sensing elements, a first spectral range of light emitted by the object when the object is at a first position, and to receive a second spectral range of light emitted by the object at a second subset of sensing elements when the object is at a second position.

In one exemplary embodiment, the imaging device further includes a color filter positioned between the lens and the image sensor, where the color filter comprises a plurality of zones, and each zone is adapted to allow transmission of only a particular spectral range of light. In another exemplary embodiment, the zones are configured as sections in the color filter, whereas in another exemplary embodiment, the zones are continuously graded in the color filter. According to another exemplary embodiment, the plurality of zones are arranged as different sections of a filter wheel, and the filter wheel is configured to rotate and position each of the plurality of zones, one at a time, in an optical path of light transmitted by the object. In yet another exemplary embodiment, the image sensor is a digital charge-coupled device (CCD) active pixel sensor. In still another exemplary embodiment, the image sensor is a complementary metal oxide semiconductor (CMOS) active pixel sensor.

Another aspect of the disclosed embodiments relates to a method that includes receiving data corresponding to a particular spectral range of light emitted by a particle in a flow cytometry device, processing the received data to enhance signal-to-noise ratio (SNR) of the received data and determining particle velocity from the processed data with enhanced SNR. This method also includes determining one or more peak parameters for one or more peaks of the processed data with enhanced SNR, mapping colors in accordance with placement of the peak parameters and/or ratios of the peak parameters, and determining color of the light emitted by the particle in accordance with the mapping.

In one exemplary embodiment, the received data is produced at least in-part by processing the particular spectral range of light that is analog format with an analog filter. In another exemplary embodiment, the one or more peak parameters is selected from a group of parameters consisting of: a peak intensity, a peak width, and a peak area.

Another aspect of the disclosed embodiments relates to a method that includes flowing one or more particles through a channel of a flow cytometry device, causing the one or more particles to emit light, receiving light emitted by the one or more particles after transmission through a color filter, where the color filter comprises a plurality of zones and each zone is configured to allow transmission of only a particular spectral range of light incident thereupon, and where the light emitted by each particle at different positions within the channel is incident upon different zones of the color filter. Such a method also includes producing data associated with the received light, and processing the data to identify the one or more particles.

In one exemplary embodiment, the above noted method further includes determining velocity of the one or more particles flowing through the channel. In another exemplary embodiment, the above noted method further includes directing at least one of the one or more particles through a channel branch based on identity and velocity of the at least one of the one or more particles. In yet another embodiment, the one or more particles are identified based on at least a color of the received light. According to another embodiment, a first particle of the one or more particles emits light at a different spectral range than a second particle of the one or more particles. In still another embodiment, the color zones of the color filter are continuously graded, the received light emitted by the one or more particles corresponds to a continuous waveform, and the processing the data comprises parsing the data into a plurality of spectral bands, where the number of spectral bands is changeable.

According to another exemplary embodiment, the above noted method further includes modifying velocity of the one or more particles flowing through the channel to facilitate parsing of the data into a particular number of spectral bands. In one exemplary embodiment, at least one of the velocity and the number of spectral bands are specified by a user of the flow cytometry device. In another exemplary embodiment, the velocity is set according to instructions programmed into the flow cytometry device. In still another embodiment, each zone of the color filter is configured as a section of the color filter separate from other sections in the color filter. In yet another exemplary embodiment, the wavelength sub-range of the portion of the light transmitted by one zone overlaps with the wavelength sub-range of the portion of the light transmitted by a another zone, whereas in another exemplary embodiment, the wavelength sub-range of the portion of the light transmitted by one zone does not overlap with the wavelength sub-range of the portion of the light transmitted by another zone.

Another aspect of the disclosed embodiments relates to a method for identifying a particle by an imaging device that includes causing a particle within a sample affixed to a movable stage to emit light when the movable stage is at a first position, receiving light emitted by the particle at a first section of the imaging device, where the first section is responsive to a first spectral range of light incident thereupon. Such a method further includes moving the stage to one or more additional positions, receiving light emitted from the particle when the stage is positioned at each of the one or more additional positions at corresponding one or more additional sections of the imaging device, where each additional section of the imaging device is responsive to a particular spectral range of light incident thereupon. The above noted method also includes processing data corresponding to the light received at the first section and at the one or more additional sections of the imaging device to identify the particle.

In one exemplary embodiment, the above noted method further comprises using a lens to direct the light emitted from the particle onto the imaging device. In another exemplary embodiment, the method additionally includes using a color filter that includes a plurality of zones and is positioned between the lens and the image sensor to allow only a particular spectral range of the light emitted by the particle to reach the imaging device. According to another exemplary embodiment, the zones are continuously graded in the color filter. In yet another exemplary embodiment, where the plurality of zones are arranged as different sections of a filter wheel, using the color filter comprises rotating the wheel to position a first zone in optical path of the light emitted by the particle and rotating the wheel to position a second zone in optical path of the light emitted by the particle. In another exemplary embodiment, the light is received by a passive or an active pixel imaging sensor that is configured to detect, and generate a signal corresponding to, the light incident thereupon. According to another embodiment, identifying the particle is carried out based on a color of light detected at the imaging device.

Another aspect of the disclosed embodiments relates to a method that includes flowing at least one particle through a fluidic channel of a flow cytometry device, causing the at least one particle to emit light, and using a lens to direct the emitted light to a diffractive component, where the diffractive component directs a portion of the emitted light to an aperture. The above noted method also includes receiving, at a detector, the light is propagated through the aperture, where the received light at the detector consists of a particular spectral range dependent at least in-part on position(s) of the at least one particle within the fluidic channel, and processing data corresponding to the light received at the detector to identify the one or more particles.

In one exemplary embodiment, receiving the light comprises receiving a first spectral range of light when the at least one particle is at a first position within the fluidic channel and a second spectral range of light when the at least one particle is at a second position within the fluidic channel. In another exemplary embodiment, the above noted method further includes determining a velocity of the at least one particle flowing through the channel. According to another exemplary embodiment, the method additionally includes directing the at least one particle through a channel branch based on identity and velocity of the at least one particle. In still another exemplary embodiment, the at least one particle is identified based on at least a color of the light received at the detector.

Another aspect of the disclosed embodiments relates to a flow cytometry device that includes a microfluidic sensing channel through which sensing channel cells can flow and can be sensed, a branch downstream of the sensing channel, two or more microfluidic branch channels downstream of the branch, and an actuator configured for fluid communication with the branch and configured to drive cells, upon activation of the actuator, to one or more of the branch channels, wherein the device is configured for a cell viability of greater than about 70.8% after cells are flowed through the device.

In one exemplary embodiment, the device comprises a color filter comprising a plurality of zones, wherein the plurality of zones comprises (i) color zones, each of which color zones transmits a portion of the light transmitted by the lens, wherein a first color zone transmits a portion different than the portion transmitted by a second color zone, and (ii) a zone that transmits light transmitted by two or more of the color zones. In another exemplary embodiment, the device comprises a photodetector that detects light transmitted by the color filter. According to other exemplary embodiments, the cell viability is in one of the following ranges: about 75% or greater, about 80% or greater, and about 85% or greater.

In another exemplary embodiment, the actuator is a piezoelectric actuator. In another exemplary embodiment, the actuator is configured to be in fluid communication with the branch and cells capable flowing through the branch with substantially no air between the actuator and the branch. According to another exemplary embodiment, the device is not configured to generate droplets. In still another exemplary embodiment, the device does not include an element that electrically charges cells or fluid in the device.

Another aspect of the disclosed embodiments relates to a flow cytometry method that includes flowing cells through a microfluidic sensing channel, in which sensing channel cells can be sensed, in a flow cytometry device, wherein the flow cytometry device comprises the sensing channel, a branch downstream of the sensing channel, two or more microfluidic branch channels downstream of the branch, and an actuator in fluid communication with the cells, where the actuator is capable of driving cells to one of the branch channels upon activation of the actuator. Such a flow cytometry method also includes sorting the cells flowing through the microfluidic channel to one of the branch channels, where cells that have passed through the device have a cell viability of greater than about 70.8%.

According to one exemplary embodiment, the device comprises a color filter comprising a plurality of zones, where the plurality of zones comprises (i) color zones, each of which color zones transmits a portion of the light transmitted by the lens, where a first color zone transmits a portion different than the portion transmitted by a second color zone, and (ii) a zone that transmits light transmitted by two or more of the color zones. In another exemplary embodiment, the device comprises a photodetector that detects light transmitted by the color filter.

BRIEF DESCRIPTION OF THE DRAWINGS

FIG. 7A is a further schematic view of portions of the FACS device of FIG. 6A, which further shows matter of interest (in this embodiment, cells) passing through a microfluidic channel of the FACS device.

FIGS. 7B and 7C are respective cross-sectional views of the FACS device of FIGS. 2-4, taken along lines B-B and C-C of FIG. 7A.

FIGS. 12A, 12B and 12C show signal processing via a bank of filters at different signal frequencies in determining the cell speed. FIG. 12A shows particles (e.g., cells with fluorophores or quantum dots) with different speeds generate different signals in time and frequency domains. FIG. 12B shows that Filter-bank architecture can be applied to estimate the speed of each individual particles by matching its signal waveform to different filters in the filter-bank. FIG. 12C shows a processing example.

FIGS. 13A and 13B show another example of a signal encoding structure in fluidic channels for an FACS device.

FIGS. 17A-17C illustrate the fabrication of a particle sorter of FIG. 15.

FIGS. 32A-32C illustrate an embodiment of a device used for flow cytometry or fluorescence-activated cell sorting (e.g. a non-limiting example of a COlor-Space-Time (COST) coding operation) comprising a diffractive grating.

FIG. 36A shows an example of a 4-slit spectral filter and the signal. FIG. 36B shows an example of a continuously graded COST filter.

DETAILED DESCRIPTION

Figure 1:
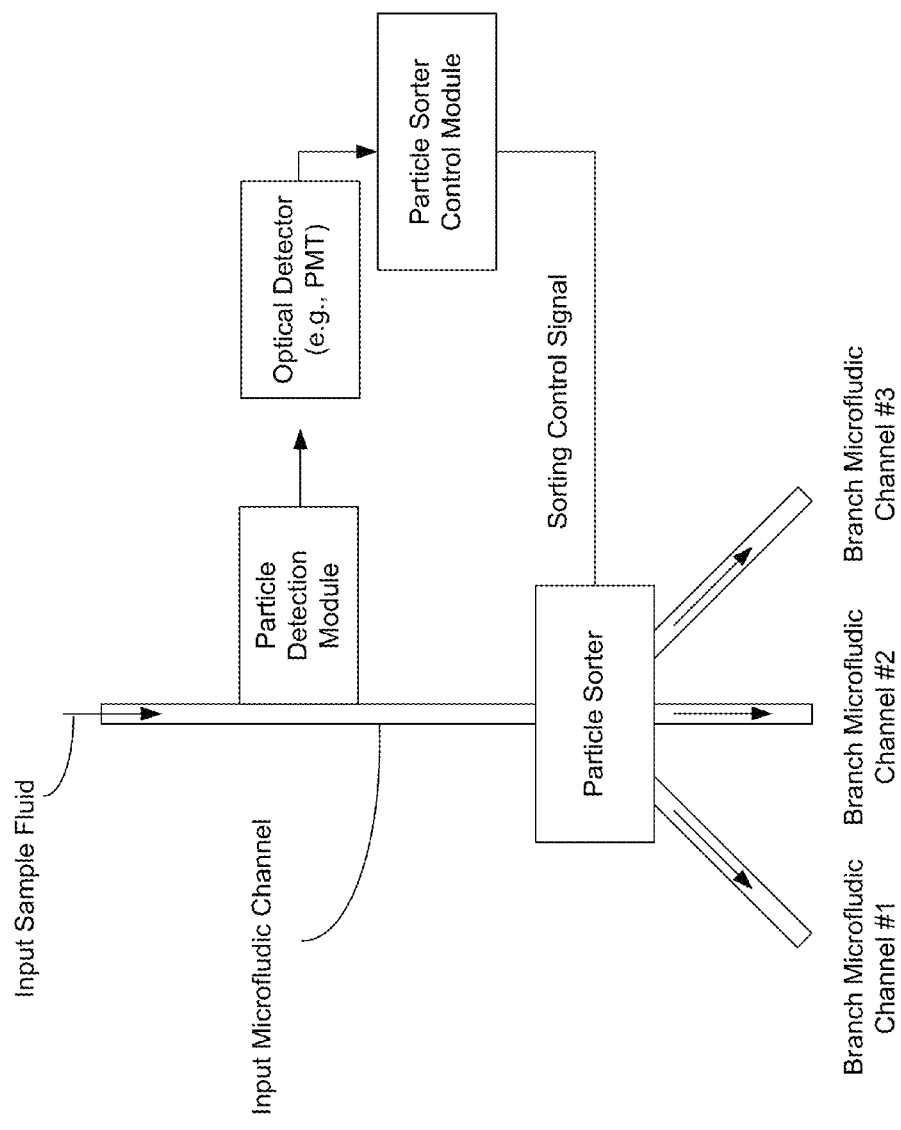
FIGS. 1, 2, 3A, 3B and 3C show examples of flow cytometry systems.

Examples of devices, systems and techniques for flow cytometry described in this document implement various technical features that are either alone or in various combinations can be used to achieve one or more technical benefits. One of the technical features, for example, is to provide optical illumination to the fluid in a flow cytometer device or system to allow optical sensing or monitoring in performing flow cytometry operations. The functionality of microfluidics can be combined with photonics to create a technology platform that provides integrated microfluidic photonics. Embracing photonics is a logical path of evolution for microfluidics, as a wide range of techniques for biological and chemical detection are photonic in nature. Fluorescence, fluorescence resonance energy transfer (FRET), optical scattering, and surface-enhanced Raman spectroscopy (SERS) are examples of effective and accurate methods to detect analytes at the cellular and molecular level. Integration of microfluidics with photonics represents not only a new technology platform but also a transformation to the new paradigm of bio-system-on-a-chip (BSoC). Integrated microfluidic photonic circuits have promising applications in biomedicine.

A flow cytometer based on FACS (fluorescence-activated cell sorter) is one example for combining photonics and microfluidics to meet some of the aforementioned requirements and can be a valuable bioanalysis tool for characterizing physical and biochemical properties of various chemical or biological particles, e.g., molecule clusters and cells, in a highly quantitative manner, and for detecting and monitoring the progression of diseases such as acute myeloid leukemia (AML) and AIDS. With the addition of the cell sorting capability to enrich the purity of biospecimens and extract rare cell types, a FACS can interrogate and sort cells with a throughput of tens of thousands of cells per second, making possible rare-event studies such as identification of bacterial cells or isolation of stem cells or tumor cells.

Various technical features described herein can be used to form a flow cytometer based on FACS. With the advent of lab-on-a-chip technologies, bulk optics in a FACS can now be replaced with integrated optics, affording some level of device miniaturization and cost reduction. The availability of small and inexpensive diode lasers—originally developed for optical disk and other devices—has also provided impetus for the development of micro FACS. Multicolor detection that scales with a lab-on-a-chip platform can be achieved in an integrated system described in this document by eliminating multiple photodetectors such as PMTs and by providing signal encoding in different optical signals generated in the system.

Cytometry devices often are utilized to detect and optionally sort particles according to light emitted by the particles and/or light that has interacted with the particles (e.g., light diffracted, scattered and/or reflected by particles). Light is electromagnetic radiation of any wavelength or frequency. The value for the wavelength or frequency generally is for light propagating through a vacuum. Light can be characterized as visible light, ultraviolet light and/or infrared light in some embodiments. Visible light generally is of a wavelength of about 390 nanometers to about 750 nanometers, and generally is of a frequency of about 400 terahertz (THz) to about 790 THz. Infrared light generally is of a wavelength of about 0.74 micrometers to about 300 micrometers, and generally is of a frequency of about 300 gigahertz (GHz) to about 400 THz (near infrared often is about 120 THz to about 400 THz; mid infrared often is about 30 THz to about 400 THz; and far infrared often is about 300 GHz to about 30 THz). Ultraviolet light generally is of a wavelength of about 10 nanometers to about 400 nanometers, and generally is of a frequency of about 0.75 petahertz (PHz) to about 30 PHz (near ultraviolet often is about 400 nm to about 300 nm, mid ultraviolet often is about 300 nm to about 200 nm, and far ultraviolet often is about 200 nm to about 122 nm). A photon is a quantum of light and a photon can have a particular photon energy.

A particle sometimes is an agent that emits light (e.g., a fluorophore), and sometimes is a complex of molecules that includes an agent that emits light. In some embodiments, a particle includes a one or more biological agents (e.g., cell, protein, nucleic acid, biological membrane (e.g., vesicle, liposome, the like and combinations thereof). A particle can include in some embodiments one or more antibodies in association with one or more biological agents (e.g., bound to a biological agent). An antibody sometimes is linked to an agent that emits light. A combination of different particles can be introduced to a flow cell of a flow cytometry device. A combination of different particles sometimes includes different particles that emit different wavelengths of light.

In some embodiments, light introduced by a light source is transmitted though a fluidic channel wall into the channel interior. The angle of light emitted by a light source can be at an angle with respect to the channel wall suitable for illuminating a particle within the channel. In certain embodiments, a particle in a fluidic channel can interact with light introduced into a channel, and light that has interacted with the particle and is scattered, reflected or diffracted by the particle can be transmitted from the channel to one or more other components in a cytometry device.

In some embodiments, a particle in a fluidic channel can emit light of a particular wavelength or in a particular wavelength range, and all or a portion of the wavelength range can be transmitted from the channel to one or more other components in a flow cytometry device. A particle sometimes emits light of a particular wavelength or wavelength range, which wavelength or wavelength range can be different than the wavelength or wavelength range emitted by a light source (e.g., excitation wavelength(s) emitted by the light source may excite a fluorophore particle or fluorophore attached to a particle and the fluorophore may emit light of different wavelength(s)). Light emitted by a particle, or that has interacted with a particle, can transmit through a fluidic channel, and transmitted through or conducted by one or more intermediary structures, to a detector. Non-limiting examples of intermediary structures include a mask, color filter, waveguide, mirror, lens, filter, photodiffractive component (e.g., prism, diffraction grating), the like and combinations thereof.

A cytometry device may include an optical filter, a reflector or combination thereof. A device may include one or more optical filters, non-limiting examples of which include absorptive filter, dichroic filter, monochromatic filter, infrared filter, ultraviolet filter, neutral density filter, longpass filter, bandpass filter, shortpass filter, guided-mode resonance filter, metal mesh filter, polarizer filter, optical notch filter (e.g., precision optical notch filter) the like and combinations thereof. Non-limiting examples of filters, such as color filters, are described in greater detail herein. A device may include one or more components that reflect light, non-limiting examples of which include flat mirrors, curved surface mirrors, parabolic surface mirrors and dichroic mirrors. A mirror sometimes substantially reflects light of a particular wavelength range and is substantially transparent to, and does not reflect, light of a different wavelength range. A mirror in some embodiments, substantially reflects light in a wavelength range that excites a fluorophore (e.g., a fluorphore particle or fluorophore linked to or associated with a particle) and is substantially transparent to light in a wavelength range emitted by the excited fluorophore.

Figure 5:
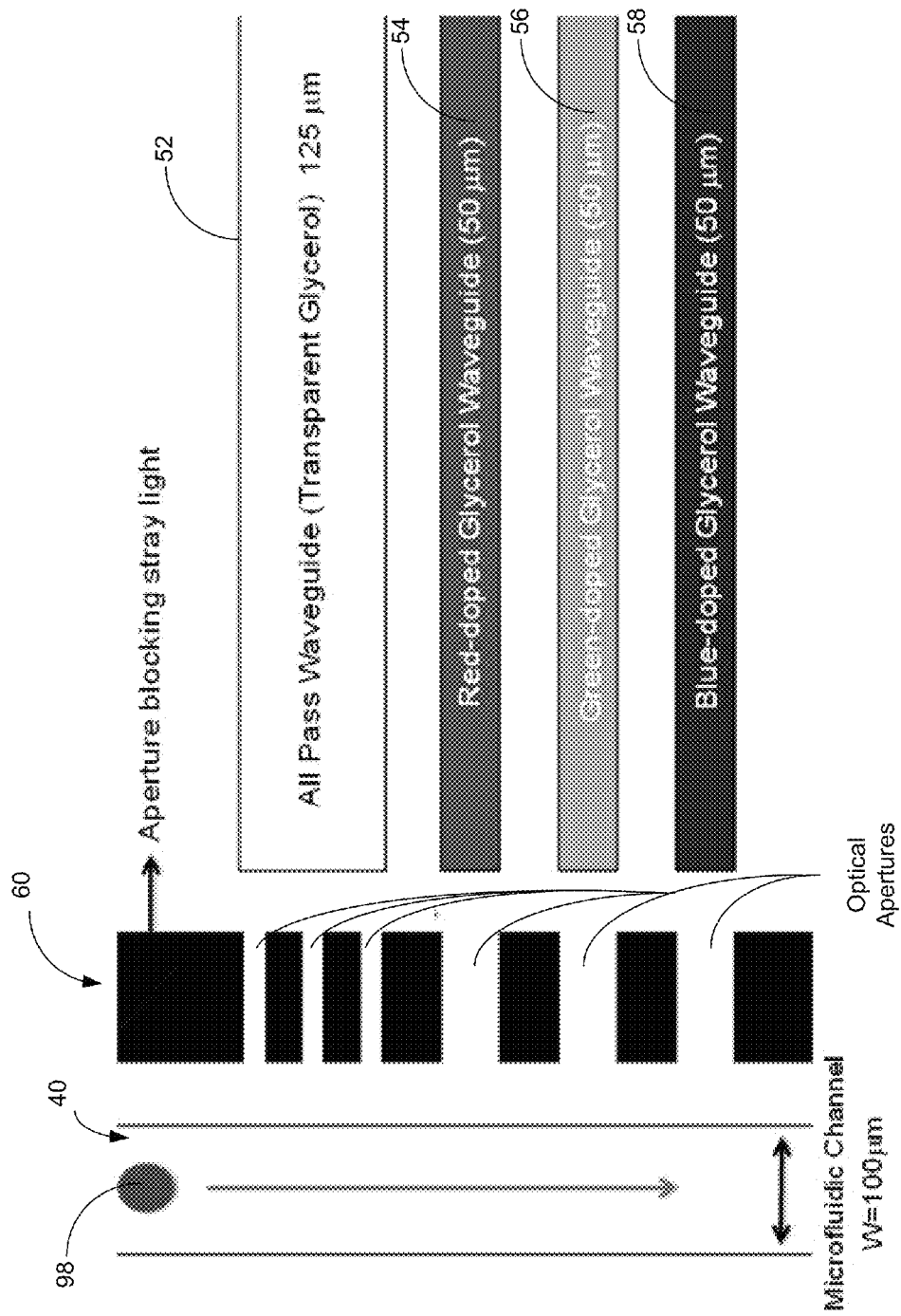
FIG. 5 shows an example of the FACS system with optical filter waveguides and optical apertures.

Light emitted from, or light that has interacted with, a particle in a channel sometimes is transmitted from a fluidic channel to a color filter. A color filter often includes two or more zones (e.g., about 2, 3, 4, 5, 6, 7, 8, 9, 10, 15, 20, 25, 30, 35, 40, 45, 50, 60, 70, 80, 90 or 100 or more zones). A color filter sometimes includes a mask comprising substantially transparent zones and substantially opaque zones (e.g., optical apertures, bands), and waveguides in effective connection with the substantially transparent zones. Some of the waveguides can be colored, and transmit a wavelength subrange of the wavelength range transmitted by the mask. A color filter that includes a mask and waveguides sometimes is in contact with a fluidic channel in which particles flow, and light from the fluidic channel sometimes does not transmit through any other component prior to being received by the mask or a waveguide. A non-limiting example of a color filter comprising a mask and waveguides is shown in FIG. 5.

Figure 36B:
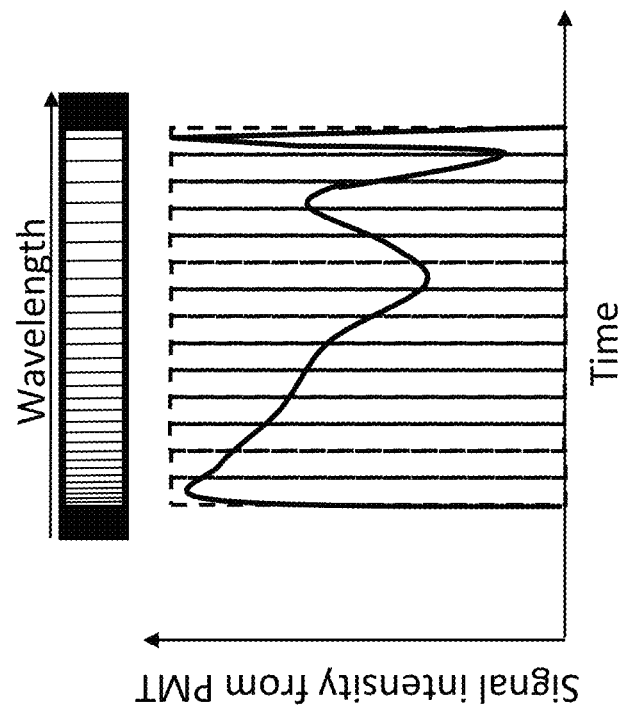
FIG. 36A and FIG. 36B illustrate two COST filter designs and the signals detected by the optical detectors in the optical path following corresponding filters.
Figure 36A:
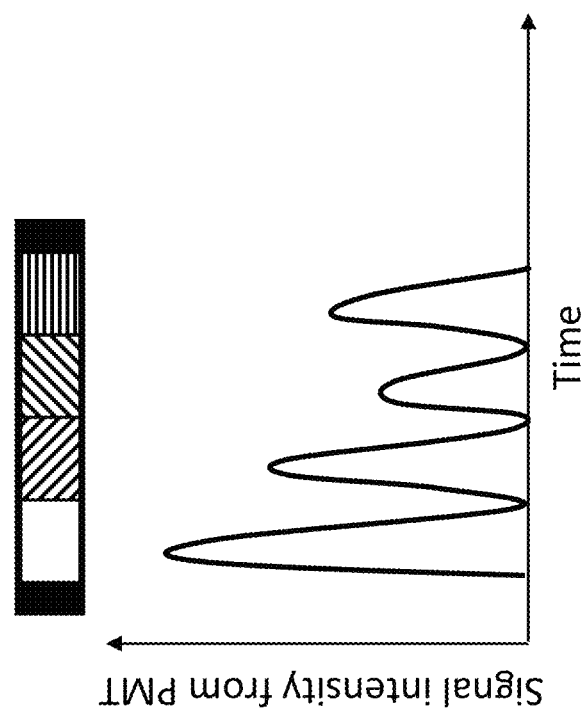

A color filter sometimes is not directly in contact with a fluidic channel in a cytometry device. A color filter sometimes is located a certain distance from a fluidic channel in which a particle flows, and sometimes a distance of about 1 centimeter (cm) to about 100 cm (e.g., about 5, 10, 15, 20, 25, 30, 40, 50, 60, 70, 80 or 90 cm). Light emitted by a channel sometimes is transmitted through one or more other components (e.g., lens, mirror) before the light, or modified version thereof, contacts a color filter. Zones sometimes are discrete zone segments on a filter and sometimes zones are substantially continuous (e.g., continuously graded color zones). A non-limiting example of a color filter that includes discrete zones is illustrated in FIG. 36A and a non-limiting example of a color filter that includes substantially continuous transitions between zones is illustrated in FIG. 36B.

A color filter often includes one or more zones that transmit substantially all of the light that is transmitted to the filter (e.g., all pass filter zone). A color filter generally includes two or more zones that transmit a portion of the light transmitted to the filter (i.e., referred to color filter zones), where at least one color zone transmits a different portion of light than another color zone. Color zones in a color filter sometimes perform as broad pass, continuous, band pass filters, the like or combinations thereof. A different portion of light sometimes is a different wavelength subrange of, a different energy subrange of, and/or a different frequency subrange of, the light wavelength range, light energy range and/or light frequency range, respectively, received by the color filter. Thus, a first color zone can transmit a first wavelength subrange, and a second color zone can transmit a second wavelength subrange, which first wavelength subrange and second wavelength subrange are different (e.g., overlapping or not overlapping), and which wavelength subranges are within the wavelength range of the light received by the color filter. The different wavelength subranges transmitted by color zones sometimes overlap and sometimes do not overlap. The lowest wavelength and the highest wavelength in a subrange of light transmitted by a color zone in a color filter sometimes differ by about 0.1 nm to about 500 nm in some embodiments (e.g., a range of about 1, 5, 10, 15, 20, 25, 30, 35, 40, 45, 50, 55, 60, 65, 70, 75, 80, 85, 90, 100, 150, 200, 250, 300, 350, 400 or 450 nm). A color filter sometimes includes one or more zones that transmit substantially none of the light transmitted to the color filter (e.g., substantially opaque zone). A color filter comprising multiple zones sometimes is referred to as a filter with a "series of optical filters" and an "array of optical filters" herein, where each of the optical filters in the series or the array is a zone.

In some embodiments, a color filter includes three or more zones that transmit different portions of light transmitted to the filter. For example, a color filter may include a first zone that transmits substantially green light, a second zone that transmits substantially blue light, and a third zone that transmits substantially red light. The latter example is not limiting, and certain color zones within a color filter can transmit any suitable wavelength subrange of the wavelength range of light received by the filter.

A color filter and zones of a color filter can have dimensions suitable for detecting a particle, determining velocity of a particle, determining size of a particle and/or detecting wavelength(s) of light emitted or that have interacted with a particle, for example. In some embodiments, a color filter is substantially circular and includes suitably shaped zones distributed around the circular structure for transmitting light (e.g., circular, ovoid, rectangular, square, triangular, segment of the circle).

In some embodiments a color filter is substantially rectangular and includes substantially one zone across the shorter rectangular dimension and multiple zones sequentially distributed along the longer rectangular dimension, according to a top view of the color filter. In such embodiments, the width of a discrete zone is the length of the zone parallel to the longer rectangular dimension of the color filter. In such embodiments, the zone widths can be regular or can vary. In color filter embodiments that include varying zone widths, the widths may be distributed in any suitable pattern, non-limiting examples of such patterns including periodic, chirp and pseudo-random patterns. In some embodiments, substantially opaque zones are distributed in a pattern of varying width, and zones that transmit light sometimes are distributed in a pattern of regular widths.

A color filter can be manufactured by any suitable process known in the art. A color filter sometimes includes a structure infused with one or more agents that permit at least one color zone to transmit light having a wavelength range different than the wavelength subrange of light transmitted by another zone. Zones with different transmission properties may include different agents or one agent in different amounts, for example.

A color filter may comprise multiple layers. A color filter sometimes includes a support structure on which one or more coating layers are deposited. Any suitable structure or support structure can be utilized, and non-limiting examples include glass, polymers and the like. Each zone independently may be of substantially uniform thickness or varying thickness (e.g., stepped thickness, tapered or flared thickness (e.g., substantially uniform taper or flare). Each zone independently may include one or more coatings (e.g., same or different materials in each coating) and/or one or more layers (e.g., same or different materials in each layer). A zone comprising multiple layers may include alternating layers, each layer comprising different materials. Each coating or layer in a zone may have the same refractive index or may have different refractive indices. Zones of a color filter that transmit different wavelength ranges of light may have the same refractive index or may have different refractive indices. Zones that transmit different wavelengths of light sometimes have a different number of layers, different materials, different thicknesses, the like or combination thereof. Where adjacent zones have different thicknesses, the transition from one thickness to another may be any suitable transition, such as stepped, tapered or flared for example.

In some embodiments, a cytometry device comprises a splitter that effectively receives light emitted by, or light that has interacted with, a particle in a fluidic channel. The light emitted from the fluidic channel may be transmitted through one or more other components in the device (e.g., lens, filter) prior to the splitter receiving such light. A splitter can split received light into two or more split beams. Each of the two or more split beams sometimes is directed to a separate color filter. Thus, a cytometry device sometimes includes two or more color filters, and each or the color filters sometimes include color zones that transmit different wavelength subranges of light than color zones in other color filters. Light in one split beam can be of the same wavelength range or different wavelength range as light in another split beam. Non-limiting examples of splitters include those that comprise two triangular glass prisms, half-silvered mirrors and dichroic mirrored prisms.

A flow channel, color filter and optical detector (e.g., photodetector, photosensor) in a cytometry device often are configured for detecting light from a particle in the channel multiple times as the particle translocates through the channel. As a particle travels from one position to a second position in a particular portion of a channel in a flow cytometry device, light emitted from the particle, or light that has interacted with the particle, at the first position can be transmitted through the channel to a first position on the image plane of the color filter. Light emitted from the particle, or light that has interacted with the particle, at the second position can be transmitted through the channel to a second position on the image plane of the color filter. Where the first position and second position on the color filter are at different color zones, the wavelength range of light transmitted by each color zone to a photodetector will differ, and the photodetector will detect two different light signals over time for the same particle at the two different positions in the flow channel. In such embodiments, a color filter transmits multiple, discrete wavelength ranges of light by multiple, discrete zones in the filter for the same particle to a photodetector (e.g., one photodetector). In some embodiments, a device does not transmit different wavelengths of light from one filter to multiple photodetectors in a photodetector array.

A color filter in a cytometry device sometimes includes no mirrored surfaces, and in some embodiments, a color filter is not a Fabry-Perot cavity filter or Fabry-Perot etalon. In certain embodiments, a color filter in a cytometry device is not a Bragg reflector, which Bragg reflector is defined as having multiple layers and reflects light having a wavelength about four times the optical thickness of the layers.

A color filter often is not directly in contact with a photodetector component of a device. A color filter often is located a certain distance from a photodetector component surface, for example a distance of about 0.1 cm to about 20 cm away from a photodetector component surface (e.g., about 0.5, 1, 2, 3, 4, 5, 6, 7, 8, 9, 10, 15, 20 cm). In certain embodiments, one color filter is oriented with one photodetector such that light transmitted by the color filter is transmitted to the one photodetector and no other photodetector. A device includes no photodetector array in some embodiments, and one color filter is in detectable association with one photodetector and no other sensor cells of a photodetector array. A photodetector component surface often is not directly in contact with, and often not distributed along, a fluidic channel in a flow cytometry device, and often is located a certain distance from the fluidic channel.

A cytometry device may include one or more lenses. A lens may be included in a device as a single lens or an array or plurality of lenses (e.g., compound lens; a lens array may include about 2, 3, 4, 5, 6, 7, 8, 9, 10 or more lenses). A lens can be constructed from any suitable material for transmitting light, and sometimes is constructed from glass and/or a polymer, for example. A lens may be of a suitable geometry for transmitting light, and non-limiting examples of lenses include biconvex (double convex, convex), equiconvex, biconcave (concave), plano-convex, plano-concave, convex-concave (meniscus). A lens in a device sometimes focuses light. A lens sometimes focuses light on an image plane of a color filter, and sometimes a lens focuses light on an image plane of a photodetector. A lens sometimes magnifies an image, such as an image transmitted from a flow channel. A lens in some embodiments demagnifies an image, such as image transmitted from a color filter to a photodetector. Magnification or demagnification can be at any suitable level, and sometimes is about 2× to about 1,000× (e.g., about 10×, 50×, 100×, 200×, 300×, 400×, 500×, 600×, 700×, 800×, 900× magnification or demagnification). A lens sometimes receives light from a channel and focuses that light on an image plane of a color filter. A lens sometimes receives light from a color filter and focuses the light on an image plane of a sensor surface.

A flow cytometry device sometimes includes a waveguide and sometimes includes no waveguide (e.g., no waveguide in association with a channel in which particles flow). In some embodiments, a cytometry device includes a structure that substantially blocks ambient light from interacting with one or more components of the device. Such a structure sometimes is one or more tubes of suitable cross section (e.g., rectangular, square, circular, ovoid) and sometimes is a box, for example. A structure that substantially blocks ambient light sometimes functions as a support for certain components (e.g., lens).

Any of the cytometry device embodiments shown by non-limiting examples in FIGS. 28 to 32C and 35 to 36B can be coupled with one or more sorting components described herein. In certain embodiments, a flow cytometry device contains fluid and there is substantially no air-to-fluid interface, or meniscus, located between a piezoelectric actuator and a fluidic channel branch. In some embodiments, a cytometry device contains fluid and there is substantially no air-to-fluid interface, or meniscus, located between a piezoelectric actuator and a particle to be sorted. Channels in a flow cytometry device often contain fluid and there often is substantially no air-to-fluid interface or meniscus in the channels of the device. A cytometry device often includes no gas-filled reservoir, no gas pocket or component that applies a gas (e.g., air) to a channel.

FIG. 1 shows an example of a system for flow cytometry in which various technical features described in this document can be implemented. This system includes an input fluidic channel including a first port for receiving a sample fluid or the input sample fluid, and a second port for outputting the received sample fluid. A particle sorting junction or a particle sorter is provided for sorting particles within the sample fluid and is coupled to the second port of the input fluidic channel. Downstream from the particle sorting junction, two or more branch fluidic channels are coupled to the particle sorting junction as outlets of the sample fluid from the second port of the input fluidic channel. An actuator is coupled to the particle sorting junction to control a direction of the sample fluid in the particle sorting junction in response to a sorting control signal. This actuator can reside inside the particle sorting junction or in a fluid containing region that is adjacent to or in fluid communication with the particle sorting junction so that the movement of the actuator causes movement of the sample fluid at the particle sorting junction to change the flow direction of the sample fluid. In this regard, the actuator is structured to interact with the sample fluid to change the direction of sample fluid to be in different directions corresponding to the branch fluidic channels, respectively, in response to changes in the sorting control signal. Under this design, the actuator is operable to direct a target particle in the sample fluid into a selected one of the branch fluidic channels.

The actuator for sorting particles in FIG. 1 can be implemented based on various cell sorting techniques. Examples of sorting techniques include electric field-based sorting, dielectrophoretic (DEP) sorting, magnetic sorting, and hydrodynamic sorting. Sorting is useful for the detection and isolation of rare stem cells, circulating tumor cells, and *E. coli* cells, among others. Implementing a hydrodynamic sorter may involve external check values, integrated valves, or external syringe pumps. Notably, the actuator in FIG. 1 can be implemented to include a piezoelectric actuator that moves in response to a voltage signal as the sorting control signal to cause the sample fluid in the particle sorting junction to change the flow direction. Such a microfluidic cell sorter with integrated piezoelectric actuator is easy to fabricate and can operate at low voltages, e.g., less than 10 Vp-p. In the experiment of instantaneous flow switching, a prototype piezoelectrical actuator can be operated to change the flow stream at a relatively high frequency (e.g., ~1.7 kHz) and the amount of deflection of cells/particles in the flow can be precisely controlled. Particles of varying size, shape, and density of interest can be individually sorted in a controlled manner by the present piezoelectrical actuator. In the experiment of *E. coli* deflection, a sinusoidal voltage deflects cells at a rate of 330 cells/s and shows a highly repeatable operation in consistent with the theory. Using a specially design spatial filter and a real-time signal processing algorithm implemented in FPGA, a closed-loop sorting system can be built with a low error rate and a sorting efficiency of around 70%. Compared with other μFACS, this sorting system has a number of advantages. For example, the spatial filter design and the real-time signal processing algorithm enhance the signal-to-noise ratio by 18 dB and allow verification of sorting. For another example, the PZT-actuated sorting module is easy to fabricate, consumes little power (e.g., 0.1 mW), operates at a low voltage (e.g., <10 Vpp), and has a much faster response (e.g., 0.1-1 ms) than off-chip mechanical actuators such as check-valves and syringe pumps. As yet another example, the FPGA-based electronics control enables real-time signal amplification, user-defined delay time, programmable output waveform, and low timing jitter (e.g., <10 μsec). These features contribute significantly to a low-cost sorter that can perform high-throughput particle sorting at a single-particle level.

In the system in FIG. 1, a particle detection module is coupled to the input fluidic channel to receive light from the sample fluid in the input fluid channel. The light can be obtained form a light source such as a laser or other light source and the light is directed to illuminate the sample fluid in the input fluidic channel. This illumination of a particle in the sample fluid causes light to be generated by the particle. As such, the particle detection module produces one or more first optical signals from the received light indicative of at least a speed of a particle in the sample fluid detected by the particle detection module. In some implementations, the particle detection module can include an encoding structure that produces different optical signals from the received light and encodes the different optical signals with different codes. This encoding can be spaced-based codes or time-based codes and allows for using a single optical detector to detect multiple optical signals in the system, e.g., different optical signals from different locations in the system. An optical detector such as a PMT or avalanche photodiode is provided to receive the one or more optical signals from the particle detection module or light from other locations in the system to produce a detector signal that carries information carried by the received light. The information in the received light is extracted out by processing the detector signal from the optical detector for various purposes, including controlling the actuator and the respective sorting in the particle sorting junction.

In FIG. 1, a particle sorter control module is provided to be in communication with the particle detection module to receive the detector signal and in communication with the actuator to send the sorting control signal to the actuator. The particle sorter control module includes a signal processing mechanism to extract information from the detector signal by processing the detector signal with proper processing techniques, e.g., by using a digital signal processing (DSP) circuitry. When the optical signals are encoded, the signal processing mechanism can process the detector signal based on the different codes in the different optical signals to separate information carried by different optical signals. The particle sorter control module also includes a control mechanism that produces the sorting control signal based on the extracted information, including timing of a particle detected at the particle detection module for arriving at the particle sorting junction.

In the specific example in FIG. 1, different branch microfluidic channels #1, #2 and #3 are coupled to the particle sorting junction to receive the sorted particles from the particle sorting junction.

Figure 2:
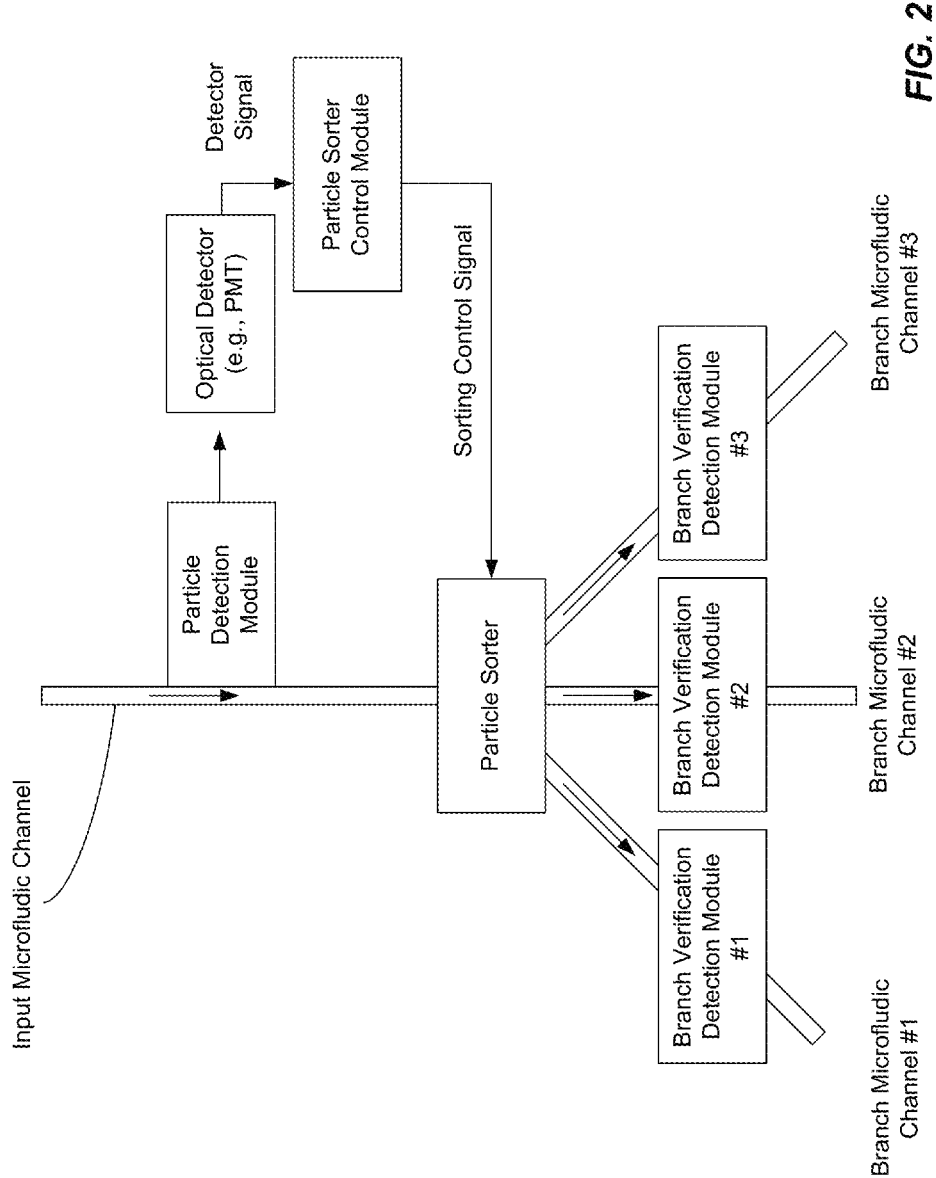

FIG. 2 shows another exemplary system for flow cytometry which provides an optical sensing mechanism in one or more branch fluidic channels downstream from the particle sorting junction. This combination of using the optical sensing at a pre-sorting location and optical sensing at a post-sorting location in the system can be used to provide better controlled operation for more efficient flow cytometry measurements. In the illustrated example, the post-sorting sensing is used to verify whether a desired particle sorting performed by the actuator in the particle sorting junction is properly executed.

The system in FIG. 2 has similar features in the system in FIG. 1. Different from FIG. 1, the system in FIG. 2 includes a branch verification structure that is coupled to one of the branch fluidic channels to receive light from the one branch fluidic channel and to produce a branch verification optical signal that can be used to verify whether a target particle is directed by the actuator into the one branch fluidic channel. Two or more such branch verification structures can be implemented in some systems. In FIG. 2, all three branch fluidic channels have such verification detection modules. In some systems, only selected branches may have such verification structures while some branches may not.

In FIG. 2, the optical detector is located to receive light which includes at least the one or more optical signals from the particle detection module and the branch verification optical signal. The optical detector produces a detector signal that carries information contained in the received light. The signal processing mechanism in the particle sorter control module extracts information of the branch verification optical signal to produce an indicator that verifies whether a target particle is directed by the actuator into the one branch fluidic channel. In some systems, this verification may be automatically fed back to the particle sorter control module which may, in response to a verification of malfunction in the sorting, interrupt the system operation, e.g., stopping the incoming sample flow and the sorting operation by the actuator. In other systems, an alert signal may be generated by the particle sorter control module to alert the operator of the system of this malfunction in the sorting.

One of technical limitations in some other flow cytometry systems is using multiple PMTs to respectively detect optical signals at different fluorescent wavelengths. Presence of multiple PMTs in such systems complicates the system design, increases the cost, and renders the systems bulky and heavy. One of technical features described in this document is to provide signal encoding in multiple different optical signals so that different optical signals are encoded with unique and mutually different or orthogonal codes. As such, these optical signals can be multiplexed together for optical detection by a single optical detector and the information carried by the different optical signals can be separated by demultiplexing based on the unique and mutually different or orthogonal codes. The demultiplexing can be performed via digital signal processing.

Figure 3A:
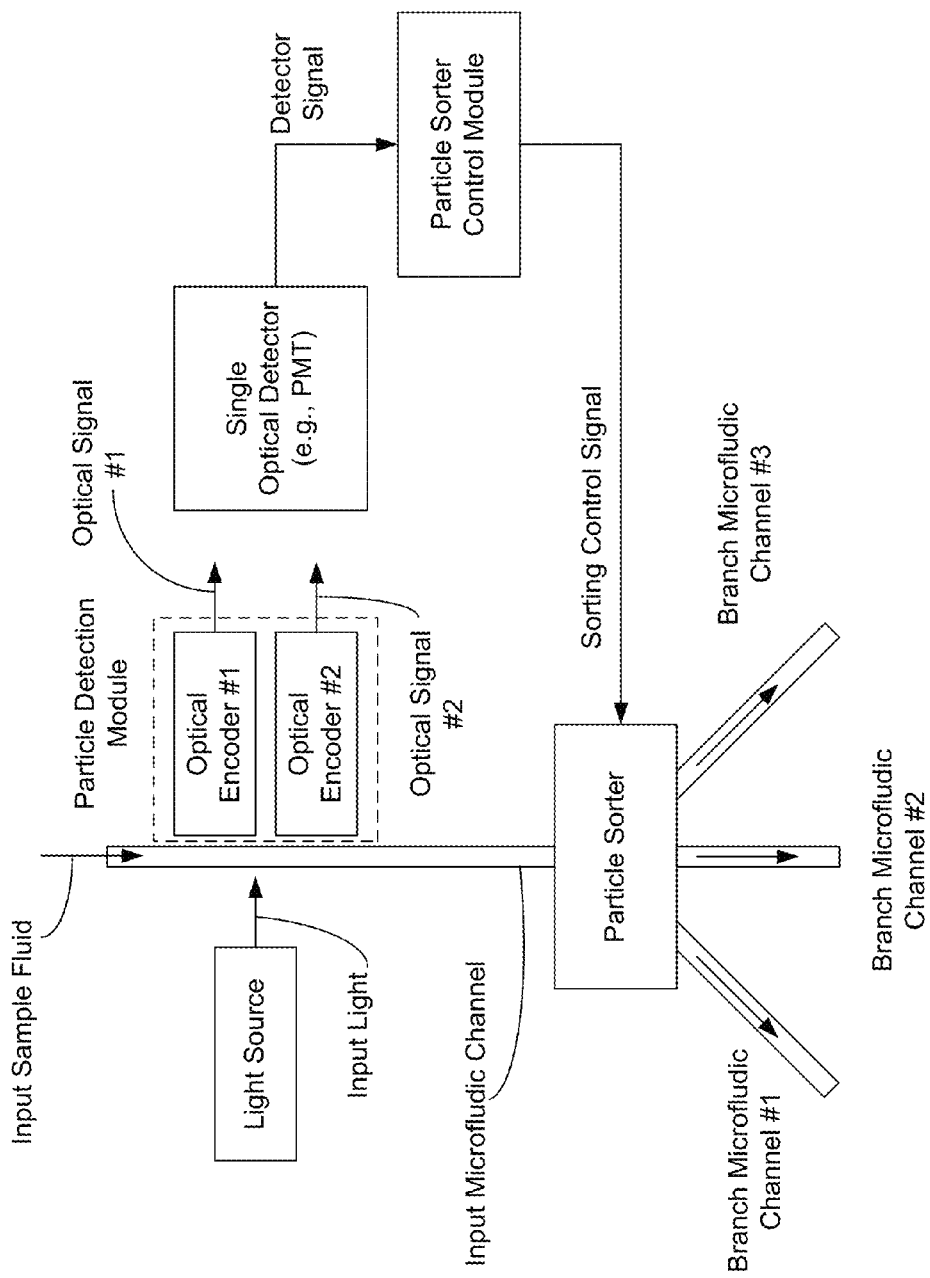
Figure 3B:
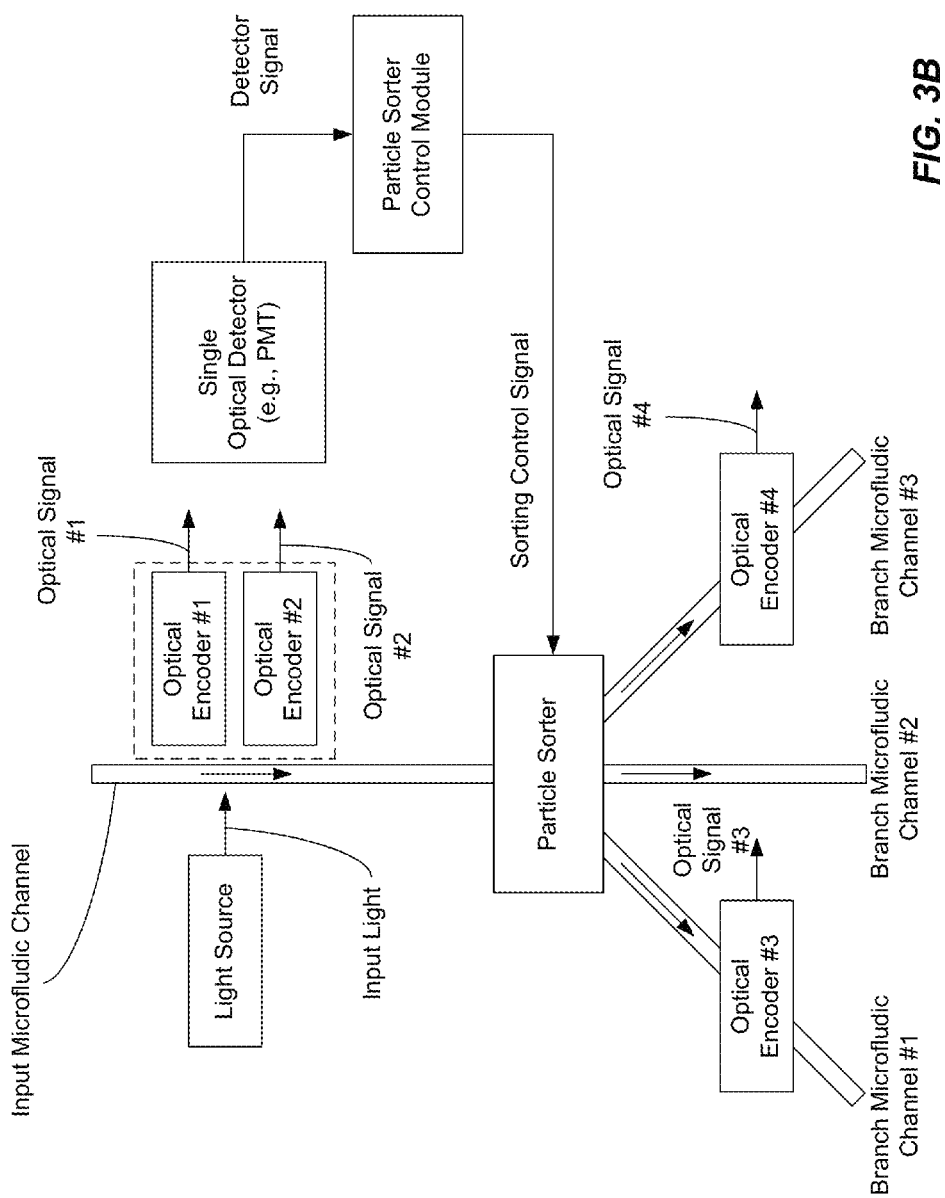

FIGS. 3A and 3B show two system examples that implement such signal encoding.

In FIG. 3A, the particle detection module coupled to the input fluidic channel is structured to include an encoding structure that produces different optical signals from the received light and encodes the different optical signals with different codes. Two optical encoders #1 and #2 are shown as examples of such an encoding structure. The first optical encoder #1 produces a first optical signal with a first code and the second optical encoder #2 produces a second optical signal with a second code that is different from the first code. The optical detector receives the different optical signals to produce a detector signal that carries information of the different optical signals and the different codes. The signal processing mechanism, e.g., the DSP, of the particle sorter control module extracts information of the different optical signals from the detector signal based on the different codes in the different optical signals. The control mechanism in the particle sorter control module produces the sorting control signal based on the extracted information, including timing of a particle detected at the particle detection module for arriving at the particle sorting junction.

In FIG. 3B, additional optical encoders are provided in the system to allow for the same optical detector to detect the encoded optical signals. The two additional optical encoders #3 and #4 are shown as examples of encoding structures in the branch fluidic channels #1 and #3, respectively. The third optical encoder #3 produces a third optical signal #3 with a third code different from the first and second codes and the fourth optical encoder #4 produces a fourth optical signal with a fourth code that is different from all other three codes. The optical detector receives the different optical signals #1-#4 to produce a detector signal that carries information of the different optical signals #1-#4 and the different codes. As a specific example, referring to FIG. 2, the third and fourth optical signals in FIG. 3B can be the branch verification optical signals when each of the optical encoders #3 and #4 are implemented as branch verification structures. The optical detector receives both the two optical signals #1 and #2 and the branch verification optical signals #3 and #4.

Figure 3C:
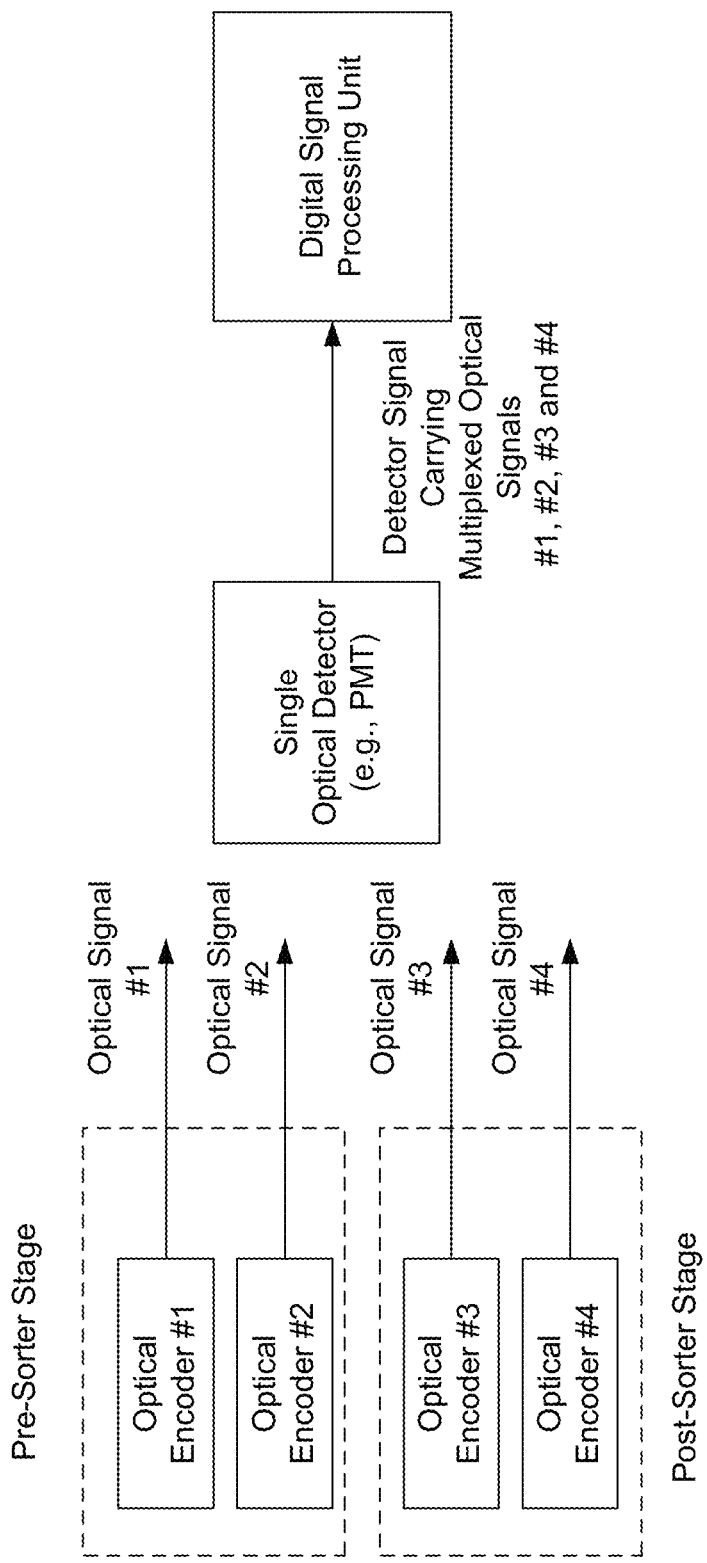

FIG. 3C shows the signal detection and processing in FIG. 3B. The signal detection is performed by the single optical detector that receives light of all four optical signals #1-#4 which are multiplexed together as the input light which is converted into the detector signal carrying the multiplexed signals #1-#4. After an analog to digital conversion, a DSP unit is used to process the multiplexed signal and to separate the four different signals based on their unique codes.

Hence, the above examples for optical encoding and decoding in flow cytometry are based on an optical interrogation method with a single optical detector based on signal encoding via optical signal structures like optical encoders illustrated in FIGS. 3A-3C. This method includes directing light to one or more of the fluidic channels that are coupled to form a network of fluidic channels to illuminate fluid carried by the fluidic channels and providing optical signal structures that are respectively coupled to at least some of the fluidic channels at different locations to produce optical signals from the light illuminating the fluid. Each optical signal carries information indicative of a property of a particle carried in the fluid at a location of the respective optical signal structure. The optical signal structures are structured to produce, respectively, unique codes in the optical signals that are different from one another. This method uses a single optical detector to collect light from all the optical signals generated at the optical signal structures to produce an electrical detector signal in response to the collected light. The electrical detector signal is processed based on the unique codes in the optical signals to separate information carried by the optical signals to extract information carried by each of the optical signals.

Specific examples of signal encoding and decoding based on a COlor-Space-Time (COST) encoding are described below in which an improved flow cytometry system can be achieved by COST to support detection of multiple (e.g., 20 or more) fluorescent wavelengths using a single detector and, more particularly in at least some embodiments, a single photo-multiplier tube (PMT) or single-photon avalanche detector (SPAD) or avalanche photodiode. In at least some embodiments, the improved flow cytometry system is implemented using lab-on-a-chip technology and architecture. A simpler version of such architecture (which can be referred to as space-time coding) in at least some embodiments is also provided to allow for multi-point detection and the consequent generation of "verification signals" to record sorting efficiency and accuracy in real time.

The following examples include methods and architectures, and/or devices embodying such, for COST coded detection of multiple fluorescent wavelengths using a single detector within a lab-on-a-chip fluorescence-activated cell sorter (FACS) or flow cytometer. Such embodiments can be considered an extension of space-time coding, which is modified to include color coding by incorporating color dyes in the waveguides transmitting the fluorescence to the detector. With the appropriate choice of dyes and calibration of the absorption spectrum, twenty or more fluorescent wavelengths can pass through the color-filter waveguides and be detected using a single detector such as a PMT or SPAD. Although in some embodiments of the present application, colored waveguides/filters are integrated on a chip to achieve COST coded detection, in other embodiments it is also possible to implement the COST concept using one or more external color filters not integrated with the chip. In such case, when the chip is disposed of after a single use or a few uses, the color filter(s) is/are not (or need not be) disposed of.

In at least some additional embodiments, the flow cytometer and/or FACS also include one or more additional components and/or features. These can include, for example, an array of integrated lenses that focus light and shorten the interrogation zone to enhance detection throughput. Also, these features can include flow disturbance minimization, 3D flow confinement and/or cascaded sorting strategies to achieve >1M enrichment factor with minimum cell loss. Also, these features can include system integration architectures with real-time electronic control and signal processing algorithms to coordinate detection and sorting, enhance sensitivity and minimize sorting error. In at least some embodiments, the COST approach provides an integrated, optofluidic solution to multicolor detection thus enabling the construction of FACS or flow cytometers that are orders of magnitude smaller, lighter and/or less expensive than existing commercial systems.

In at least one embodiment, a system for flow cytometry includes a microfluidic channel, and a first light conveying structure configured to convey substantially all visible light components, and having a first end proximate the microfluidic channel. The system also includes at least one second light conveying structure having at least one second end proximate the microfluidic channel, and extending substantially alongside the first light conveying structure, where the at least one second light conveying structure is configured to convey at least one subset of the visible light components. The system further includes a light sensing device arranged proximate respective additional ends of each of the light conveying structures, the respective additional ends being respectively opposite the respective first and second ends. Respective portions of light emanating from material passing through the microfluidic channel are received by the respective light conveying structures and communicated at least in part thereby to the light sensing device, whereby an indication of the material passing through the microfluidic channel can be determined based upon one or more signals output by the light sensing device.

Additionally, in at least one embodiment, a method of performing flow cytometry includes injecting first light into a microfluidic channel through which material is passing, and receiving second light from the microfluidic channel into a plurality of waveguides, where a first of the waveguides is conductive of substantially all visible light components, and a second of the waveguides is conductive of a subset of the visible light components. The method further includes conveying first and second portions of the second light through the first and second waveguides from respective first ends of the waveguides to respective second ends of the waveguides, communicating at least some of each of the conveyed first and second portions of the second light to a photodetector, and outputting a color-space-time signal from the photodetector.

Further, in at least one embodiment, a method of performing flow cytometry includes injecting first light into a microfluidic channel through which material is passing, and receiving second light from the microfluidic channel into a plurality of optical filters, where a first of the filters is conductive of substantially all visible light components, and a second of the filters is conductive of a subset of the visible light components. The method additionally includes communicating at least some of each of the conveyed first and second portions of the second light to a photodetector; and outputting a color-space-time signal from the photodetector.

Figure 4:
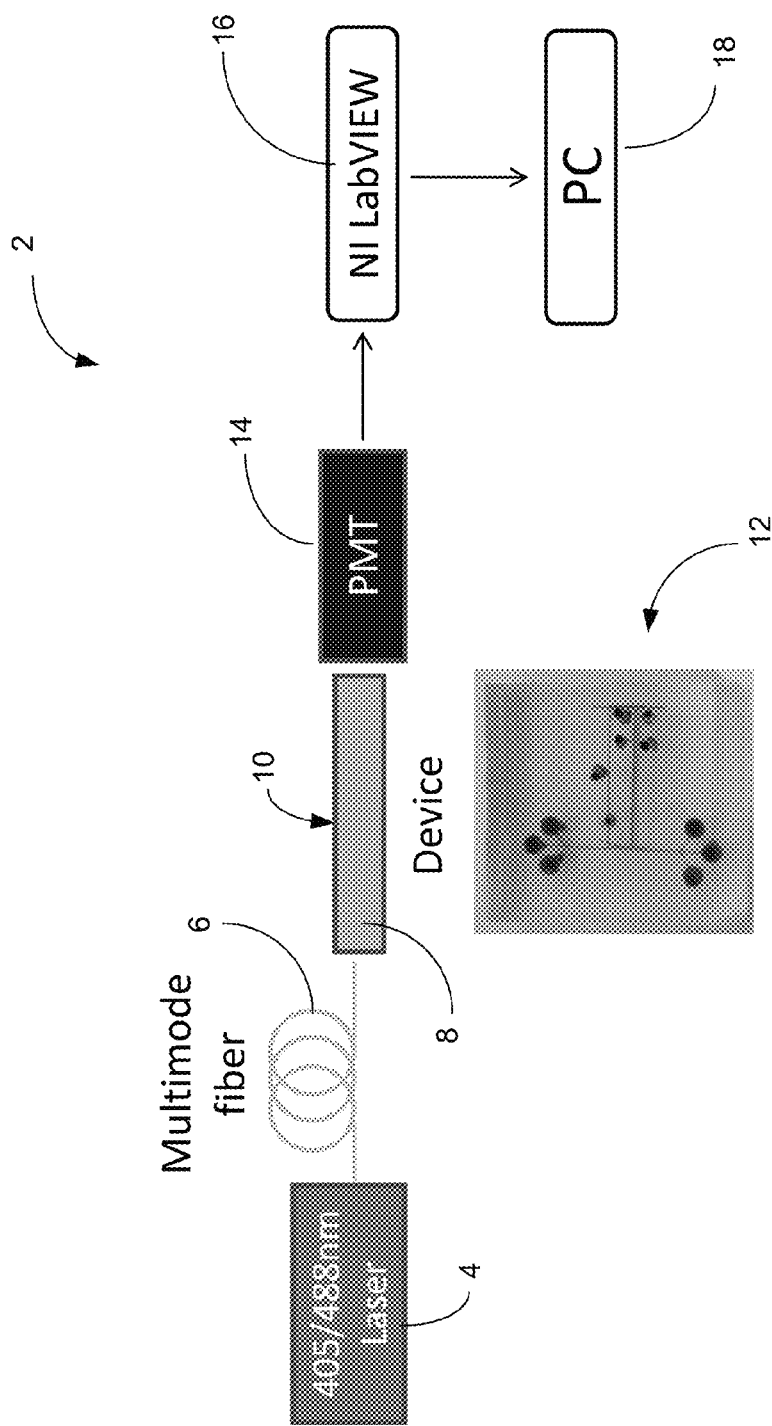
FIG. 4 is a schematic diagram showing components of an exemplary fluorescence-activated-cell-sorter (FACS) system.

Referring to FIG. 4, a schematic view is provided of an exemplary fluorescence-activated-cell-sorter (FACS) system 2 in accordance with one embodiment of the present application. As shown, the FACS system 2 includes a laser 4 that generates laser light and provides that light into a multimode fiber 6. The multimode fiber 6 in turn directs the light toward a FACS device 10 represented schematically by a box 8. An image 12 of internal components of the FACS device 10 is also provided adjacent to the box, and those internal components are described in further detail below. Finally, after the light has been provided to the FACS device 10, the light interacts with the cells or other materials or matter passing through a microfluidic channel (described further below) of that device and, as a result of that interaction, resultant light is provided from the FACS device 10 to a photo-multiplier tube (PMT) 14 that senses that light. The PMT 14 upon sensing of the light in turn output signals indicative of the sensed light to National Instruments LabView-based software 16 (available from National Instruments Corp. of Austin, Tex.), which in turn provides data to personal computer 18 (notwithstanding the representation provided in FIG. 1, the software 16 can be considered implemented on the personal computer).

In the embodiment in FIG. 4 and at least some other embodiments, multiple parameter detection is achieved by applying COlor-Space-Time (COST) coding technology. Multiple parameter detection is of greater interest when it allows for detection of 12 or more different fluorescent wavelengths of light emanating from the FACS device 10. In the embodiment of FIG. 4, it is envisioned that the FACS system 2 can support detection of multiple (e.g., 20 or more) fluorescent wavelengths of light emanating from the FACS device 10 using a single detector. The single detector can take different forms depending upon the embodiment and, while FIG. 4 shows the PMT 14 as the single detector, in other embodiments, the detector can take other forms, for example, a single-photon avalanche detector (SPAD).

The laser light source 4 in the present embodiment takes the form of a 405/488 nm (or Blu-ray standard) laser. In other embodiments, a variety of other excitation lasers can be used instead (e.g, lasers at 630-650 nm and/or other lasers manufactured by a variety of companies such as Nichia, Sony, Xerox, Omicron, etc.). Additionally, in the embodiment of FIG. 4, and at least some other embodiments, the FACS system 2 or at least certain portions thereof (e.g., the FACS device 10) can be devices employing a lab-on-a-chip technology platform that replaces the bulk optics with integrated optics.

FIG. 5 shows one example for the design of the FACS device 10 where the encoding structure includes optical aperture structure 60 with multiple optical apertures long the sensing region 40 of the input fluidic channel, and optical waveguides 52, 54, 56 and 58 that receive light from the sensing region 40 via the optical apertures in the structure 60. A particle 98 (e.g., a cell) in the sample fluid flowing through the sensing region 40 emits light that sequentially passes through the optical apertures along the input fluidic channel at different positions at different times. The light received by the waveguides 52, 54, 56 and 58 are collected by the optical detector 14 (e.g., PMT). The waveguide 52 conduct light of all wavelengths emitted by the particles 98. Waveguides 54, 56 and 58 are optical filter waveguides with optical transmission bands that are respectively centered at different center transmission frequencies. The waveguides 54, 56 and 58 produce different filtered optical transmission signals with different optical spectral bands centered at the different center transmission frequencies, e.g., red, green and blue wavelengths and at different times to be received by the optical detector 14. In some implementations, the waveguides 54, 56 and 58 are configured to have spectral overlaps in the optical transmission bands respectively centered at different center transmission frequencies. Therefore, the red waveguide 54 that transmits at a red center wavelength also transmits some light at green wavelengths and some light at blue wavelengths; the green waveguide 56 that transmits at the green center wavelength also transmits some light at red wavelengths and some light at blue wavelengths; and the blue waveguide 58 that transmits at a blue center wavelength also transmits some light at green wavelengths and some light at red wavelengths. Under this design, the signal processing may be based on the overlapping spectral information in each of the different filtered optical transmission signals to improve the signal processing fidelity. For example, the imaging processing by the human visual system based on signals from the red, green and blue color receptors or cone cells in the eye with overlapping spectral ranges can be modeled for the signal processing in the above device.

Figure 6A:
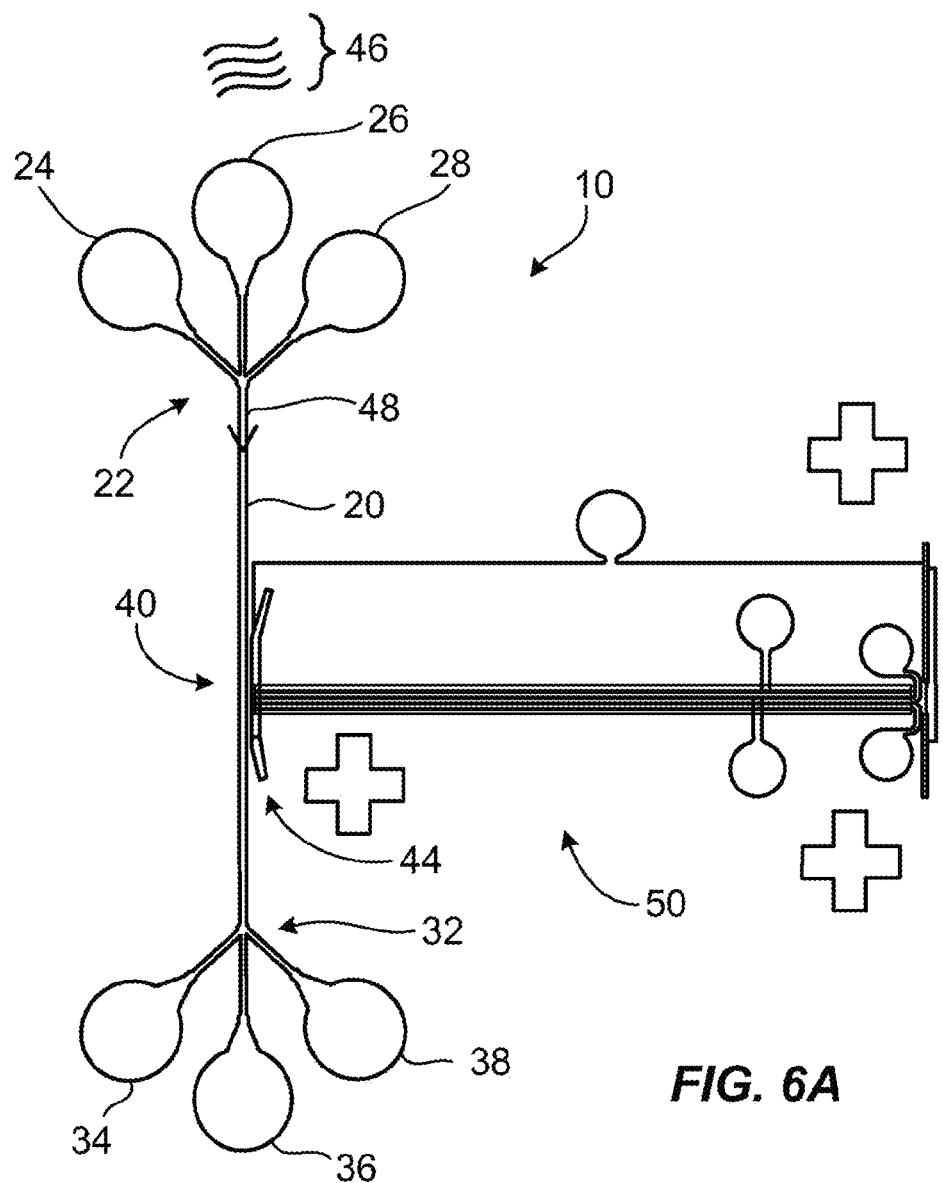
FIG. 6A is a top plan view showing in more detail components of a FACS device employed by the FACS system of FIG. 4.

Turning to FIG. 6A, the components of the FACS device 10 are shown in more detail. As shown, the FACS device 10 includes a microfluidic channel 20 through which cells or other matter of interest, suspended in fluid, pass. The microfluidic channel 20 at a first end 22 is coupled to first, second and third entry orifices 24, 26 and 28, respectively, and at a second end 32 is coupled to first, second and third outlets 34, 36 and 38, respectively. Additionally, at a sampling region 40 of the microfluidic channel 20 intermediate its ends 22, 32, an additional waveguide structure 50 is provided. The additional waveguide structure 50, along with the sampling region 40 of the microfluidic channel 20, is shown in more detail in FIG. 6B. The FACS device 10 can in at least some embodiments be considered disposable because of its low fabrication cost.

In the present embodiment, to improve reliability and reusability of the FACS device 10 as a lab-on-a-chip device, the microfluidic channel 20 is made of polydimethylsiloxane ("PDMS") and, additionally, the PDMS surfaces that are in contact with fluid (e.g., the interior surfaces of the channel) are further coated with a thin, smooth, uniform layer of amorphous Teflon (Teflon AF), particularly a Teflon coating having a lower refractive index (e.g., ~1.31) than that of water (~1.33). Use of the Teflon coating alleviates concerns (which can be present with a variety of PDMS-based microfluidic devices) associated with the porosity and permeation properties of PDMS (which can present concerns especially when dealing with small molecules).

In addition to the above benefits, another benefit of employing the Teflon-coated microfluidic channel 20 is that it facilitates the operation of the microfluidic channel additionally as a low-loss optical waveguide. That is, through the use of the Teflon-coated microfluidic channel 20, in the present embodiment light 46 entering the FACS device 10 from the multimode fiber 6 during operation generally is directed into and guided within the microfludic channel 20 (as indicated by an arrow 48) toward and into the sampling region 40 of the microfluidic channel 20. Upon reaching the sampling region 40, the light 46 impinges the cells or other matter of interest passing through the microfluidic channel and causes fluorescent light to be emitted, some or all of which the enters into the additional waveguide structure 50 arranged along a side 44 of the microfluidic channel 20/sampling region 40.

The above-described implementation of lab-on-a-chip technology is particularly advantageous insofar it constitutes an architecture that allows for multiple detection points along the flow path to enhance sensitivity and suppress noise. In some conventional flow cytometry device architectures, light from a light source (such as an excitation laser source) suffers from power splitting loss. In other words, if a cell (or other subject matter of interest) passes several (e.g., 4) different optical interrogation zones, the excitation laser power may be divided at each of those zones (e.g., divided 4 times) in a manner that results in excessive splitting loss (e.g., 6 dB splitting loss). In contrast, using the above-described embodiment employing the Teflon-coated microfluidic channel 20, the channel conducting the cells (or other subject matter of interest) serves also as the excitation light-guiding waveguide, and consequently it is possible to achieve multi-point optical interrogation as discussed further below. At the same time, the optical intensity of the guided light is lower than a tightly focused laser beam spot to avoid the effect of photo bleaching.

Figure 6B:
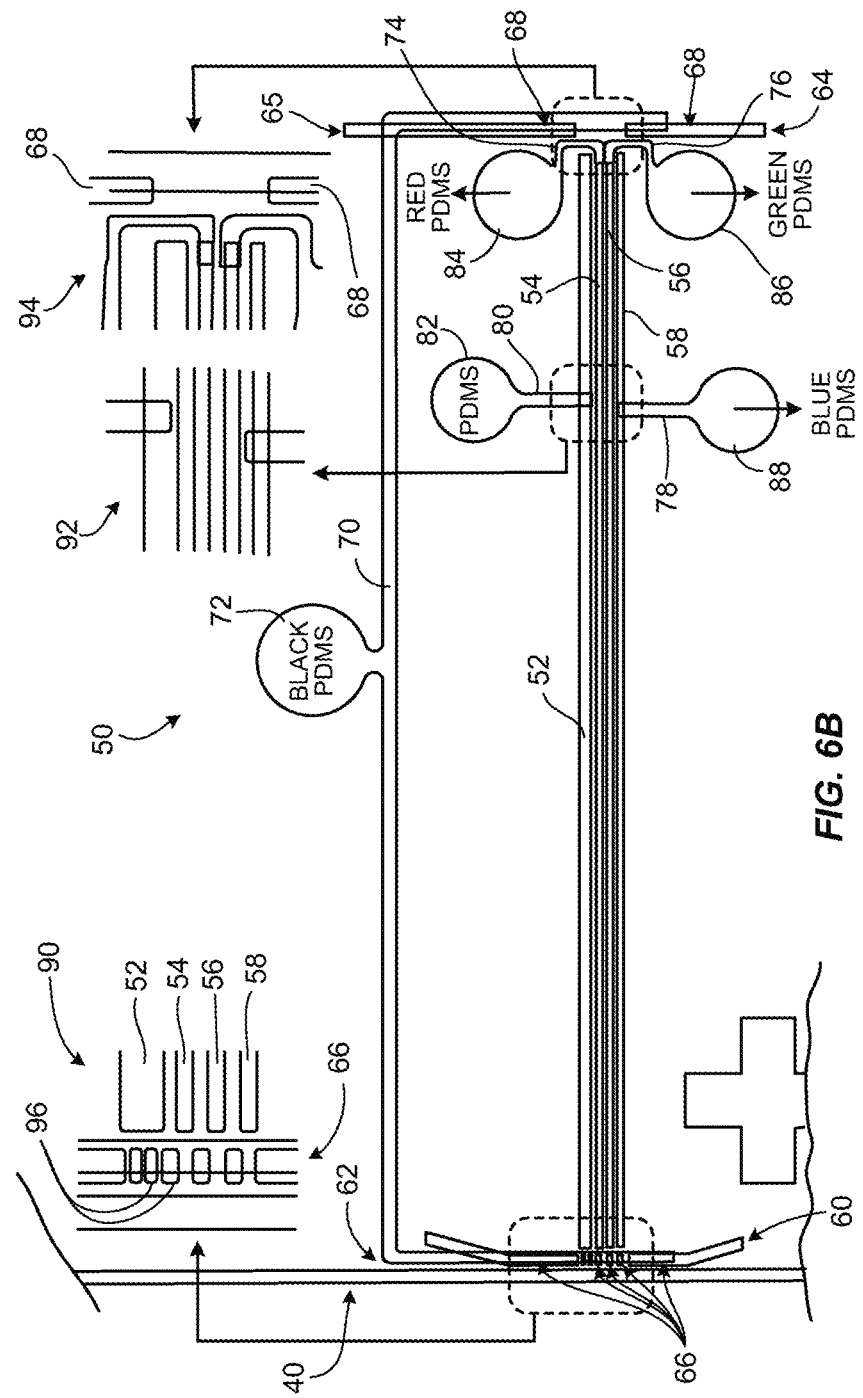
FIG. 6B is an additional view showing portions of the FACS device of FIG. 6A in cut-away in greater detail, which further includes three inset image portions.

Referring additionally to FIG. 6B, the FACS device 10 in the present embodiment achieves multi-point optical interrogation by employing the additional waveguide structure 50 extending away from the sampling region 40 of the microfluidic channel 20. As shown, then additional waveguide structure 50 does not merely include a single waveguide, but rather is shown to include first, second, third and fourth transverse waveguides 52, 54, 56 and 58, respectively. Each of the waveguides 52-58 of the additional waveguide structure 50 extends between a first filter structure 60 positioned at a first end 62 of the additional waveguide structure, which is between the waveguides 52-58 and the sampling region 40, and a second filter structure 64 positioned at a second end 65 of the additional waveguide structure opposite the first end.

Each of the first, second, third and fourth waveguides 52, 54, 56 and 58 has a different respective color. More particularly, the first waveguide 52 is transparent with no particular color (e.g., clear), while the second waveguide 54, third waveguide 56 and fourth waveguide 58 are red, green and blue, respectively. Consequently, while the first waveguide 52 is able to transmit all (or substantially all) components of light within the visible light spectrum (e.g., all light components having wavelengths within the range of about 380 nm to 750 nm, or "white light"), the other waveguides 54, 56, and 58 tend to only transmit red, green and blue light components, respectively, with other colored light components being partially filtered out. Thus, the waveguides 54-58 can also be considered optical filters. As for the first filter structure 60, this structure encompasses several block features 66 that are black or blackened/darkened and that limit the ability of light to proceed form the sampling region 40 to the waveguides 52-58. Further, with respect to the second filter structure 64, this structure also includes block features 68 that are blackened/darkened and that restrict the ability of light to proceed out of the waveguides 52-58 and out of the FACS device 10 toward the PMT 14. The features 66, 68 in particular serve to increase the contrast ratio and reduce crosstalk, and further serve as a beam block for optical isolation.

Typically, it is desirable to take care with optimizing and characterizing the various waveguides 52-58 (and particularly 54-58) to obtain desired operation. To create the red, green and blue waveguides 54-58 as well as the filter structures 60, 64, red, green, blue, and black color dyes are respectively injected into the transverse waveguides and the filter structures. In the present embodiment, the color dyes are oil soluble and can be mixed with high-index (e.g., n=1.42 to 1.46) PDMS to form a colored optical waveguide/filter structures. These high index PDMS prepolymers fill the waveguide channels, which are formed using low-index (n=1.41) PDMS. By properly choosing the color dye or a mixture of different dyes and by calibrating the absorption spectrum, the waveguides 54-58 can each have a respective desired transmission spectrum. In the present embodiment, to cover the maximum number of wavelengths, the center wavelength for the three color filters should occur at around 510 nm, 570 nm, and 640 nm.

In some implementations, each of the red, green and blue (RGB) waveguides (which as mentioned above also can be considered optical filters) 54-58 can be designed to exhibit a gradual change (rather than rapid cutoff) in its transmission characteristics with wavelength. If a single dye is not able to produce the desired spectral response, mixture of dyes may be used. Further, by appropriately coloring/darkening the features 66, 68 of the filter structures 60, 64, and appropriately choosing the shapes and arrangements of those features, light can be appropriately directed from the sampling region 40 to the waveguides 52-58 as well as directed out of the waveguides 52-58 toward the PMT 14. After the color filter design is chosen, optical design software such as ZEMAX (as available from Zemax Development Corporation of Belleview, Wash.) can be used to further design the COST coding FACS system 2.

Referring still to FIG. 6B, in the present embodiment the colored/black dyes are injected into the waveguides 54-58 and filter structures 60, 64 by way of input orifices and channels leading from those input orifices to the waveguides/filter structures. After fluid injection, all PDMS prepolymers are thermally cured to arrive at the waveguides/filter structures. To avoid formation of gaps or voids during curing, the curing is performed in vacuum. More particularly as shown, a black channel 70 leads between a black input orifice 72 and each of the filter structures 60, 64, and thus black dye input at the orifice is able to enter into the filter structures 60, 64 and form the features 66, 68 thereof. Also as shown, red, green and blue channels 74, 76 and 78 respectively lead from respective red, green and blue input orifices 84, 86 and 88, respectively, to the red, green and blue waveguides 54, 56 and 58, respectively, and thus the respective red, green and blue dyes can be injected into the respective waveguides via the respective orifices and respective associated channels. Likewise, a clear channel 80 leads between a clear input orifice 82 and the waveguide 52, allowing for clear dye to be provided to that waveguide.

Additionally, FIG. 6B also includes first, second and third insert images 90, 92 and 94 of FIG. 6B that further illustrate details of the additional waveguide structure 50 and the sampling region 40. More particular, the first inset image 90 shows with more clarity the particular features 66 of the first filter structure 60 as arranged in between the sampling region 40 and the waveguides 52-58. As will be evident from the inset image 90, the features 66 (which again are blackened/darkened to restrict light passage therethrough) are positioned generally in between adjacent ones of the waveguides 52, 54, 56 and 58, with the exception of two small features 96 that are positioned between the sampling region 40 and the waveguide 52. As for the second inset image 92, that image shows in particular the coupling of the channels 80 and 78, respectively, to the waveguide 52 and the waveguide 58, respectively. Further, with respect to the third inset image 94, that image shows the coupling of the channels 74 and 76 respectively to the waveguide 54 and waveguide 56, respectively, as well as the coupling of the channel 70 to the second filter structure 64.

Turning to FIG. 7A, a further schematic illustration is provided of the sampling region 40 and portions of the additional waveguide structure 50, namely, the waveguides 52-58 and the first filter structure 60, including the features 66 of the first filter structure 60, and the second filter structure 64 including the features 68 of the second filter structure 64. FIG. 7A also illustrates the matter of interest, in this example, cells 98 passing through the sampling region 40 of the microfluidic channel 20. As illustrated by different shading of the cells 98, different ones of the cells have been fluorescently labeled with different dyes, such that when those different cells are impinged by the light 46 (as shown in FIG. 6A), the different cells give off different colors of light suitable for transmission by the different ones of the waveguides 54-58 (all of the different colors of light are conducted by the waveguide 52).

It should be understood that, depending upon the embodiment, the additional waveguide structure 50 can be formed by multiple layers of materials. Referring additionally to FIGS. 7B and 7C, respectively, exemplary layers of the additional waveguide structure 50 taken along lines B-B and C-C of FIG. 4 are shown, respectively. FIGS. 7B and 7C in particular show that, in the present embodiment, the channels 70, 74, 76, 78 and 80 by which the colored or black PDMS prepolymers are introduced into the waveguides 52-58 and filter structures 60, 64 are at a different layer from the detection plane along which those waveguides/filter structures exist (and along which detected light passes).

More particularly, FIG. 7B shows a cross-sectional view of the additional waveguide structure 50 particularly at the location of the filter structure 60. As shown, the filter structure 60 is formed as a cavity in between a top PDMS layer 102 and a bottom PDMS layer 104. More particularly, the filter structure 60 includes both a tunnel region 110 positioned above the features 66 that particularly serve as the filtering elements. The tunnel region 110, which is positioned above the features 66 (and positioned more within the top PDMS layer 102 than within the bottom PDMS layer 104, within which are positioned the features), connects an input orifice 112 with each of the features so that black dye input at the orifice is able to enter into and form the features 66. It will be observed that the tunnel region 110 and input orifice 112 can be understood to correspond to (and serve the function as) the black channel 70 and black input orifice 72 described above with respect to FIG. 6B, albeit the arrangement of these structures is slightly different in FIG. 7B relative to FIG. 6B.

Similarly, FIG. 7C shows a cross-sectional view of the additional waveguide structure 50 at which are located only the waveguides 52-58 (but not the filter structure 60). As shown, at the particular location shown (corresponding to line C-C of FIG. 7A), all of the waveguides 52-58 are present, positioned in between a top PDMS layer 106 and a bottom PDMS layer 108. Additionally, a tunnel region 114 is shown positioned above the waveguide 52 (that is, more within the top PDMS layer 106 than within the bottom PDMS layer 108, within which are positioned the waveguides 52-58) that connects that waveguide with an input orifice 116. It will be observed that the tunnel region 114 and input orifice 116 can be understood to correspond to (and serve to function as) the channel 80 and input orifice 82 described above with respect to FIG. 6B, albeit the arrangement of these structures is slightly different in FIG. 7C relative to FIG. 6B. It will also be noted that, although corresponding tunnel regions and input orifices can be provided in relation to the waveguides 54-58 (as already discussed with respect to FIG. 6B).

Figures 8A, 8B:
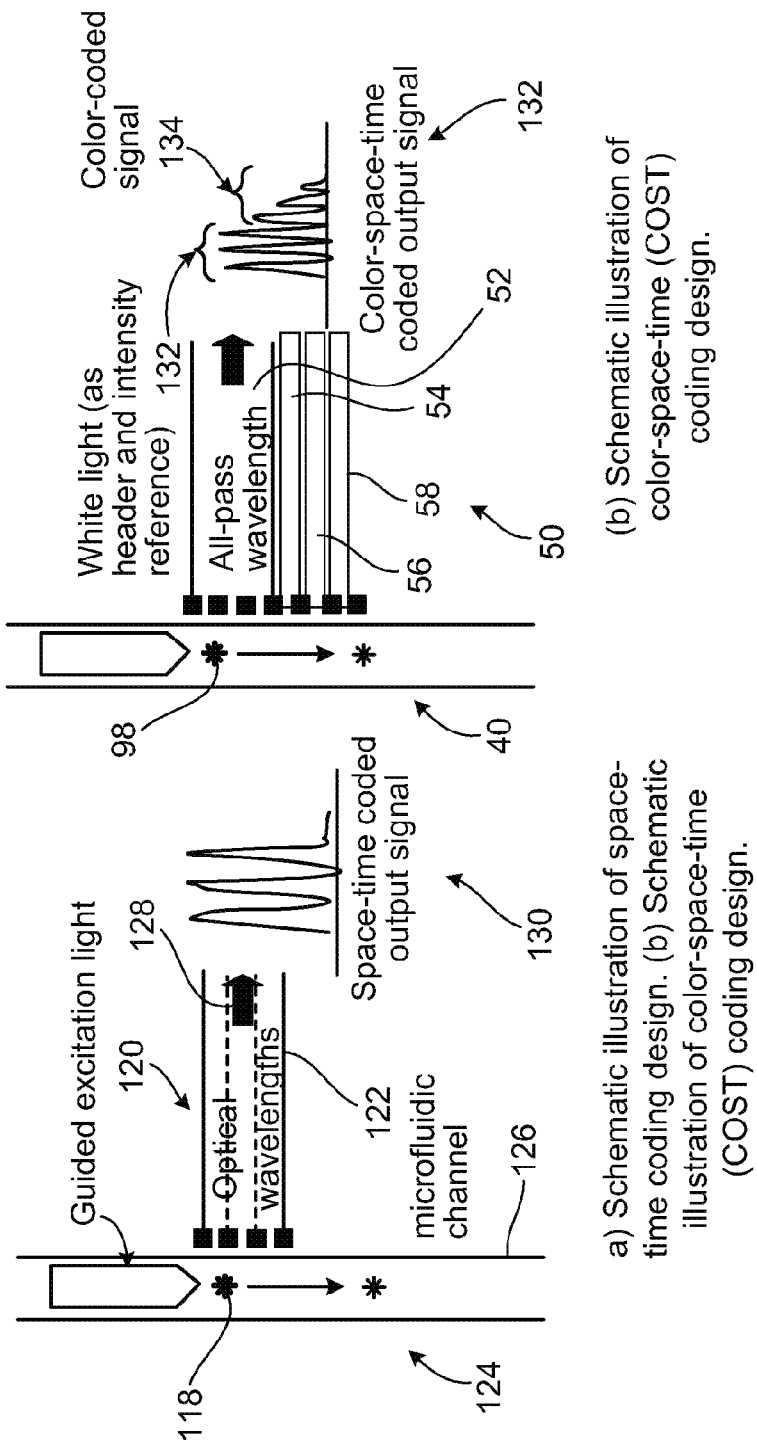
FIG. 8A is a schematic illustration of space-time coding operation of an alternate embodiment of FACS device.
FIG. 8B is a schematic illustration of exemplary COlor-Space-Time (COST) coding operation of the FACS device of FIGS. 6A-7C.

Turning to FIGS. 8A-8B, operation of FACS systems to perform space-time coding and COST coding is illustrated in greater detail. Referring first to FIG. 8A, a simpler design of a FACS system 120 is shown that only performs time-space coding. As shown, the FACS system 120, in contrast to the FACS system 2 discussed above and further below, only has an array of three clear optical waveguides 122 extending transversely away from the side of the microfluidic channel 126, and that receive fluorescent light given off by cells 118 from a sampling region 124 of a microfluidic channel 126 as filtered by a filter section 128. More particularly, one of the fluorescent cells 118 travels through the channel 126 at a typical speed of 10 cm/s to 100 cm/s. In the present embodiment, the cell 118 is optically excited along its way in a light-fluid co-propagation configuration enabled by the Teflon-coating method discussed above.

The three waveguides 122 of the waveguide array each conduct light away from the microfluidic channel 126 as indicated by an arrow 128, and provide their light output to a single PMT detector. Consequently, as one of the cells 118 travels along the microfluidic channel 126 successively past the waveguides 122 of the waveguide array, three serial peaks separated by the time of travel are detected via the PMT, thus converting the space signal (representing the cell positions) into a space-time coded output signal or time-domain signal 130. Using a digital match filter to match the waveform of the time-domain signal, one can suppress noise and obtain the travel speed of each individual cell, thus establishing the timing for downstream sorting. Further, if one chooses to interrogate a given one of the cells 118 multiple times along its path (e.g. oversampling to enhance the signal-to-noise ratio or to verify whether the cell is sorted to the right channel), it is possible to alter the coding patterns so that the resulting time-domain signal at each point of detection can be extracted using a corresponding match filter.

Turning to FIG. 8B, COST coding improves upon time-space coding by making use of additional transverse waveguides including colored waveguides such as the waveguides 54-58 discussed above. As shown, using the FACS system 2, the output signal provided by the additional waveguide structure 50 to the PMT 14 in response to fluorescent light coming from the sampling region 40 is now a color-space-time (COST) coded signal 132. Again, the waveguide 52 is clear and consequently serves as an "all-pass" waveguide, while the other waveguides 54-58 only pass light of particular colors corresponding to the coloring of those waveguides. Consequently, the COST coded signal 132 includes both a white light signal portion 132 representative of a variety of light components emanating from the waveguide 52, which can be used to establish a reference for overall fluorescence intensity, and also a color-coded signal portion 134 representative of the light of specific colors emanating from the waveguides 54-58. Assuming each fluorescence wavelength has a spectral width of around 30 nm and the three color filter waveguides 54-58 have their maximum transmission wavelengths at 510 nm, 570 nm, and 640 nm, respectively, it is estimated that more than 20 fluorescent wavelengths can be detected using a single detector (e.g., the PMT 14).

Although the waveguide 52 was described above as being a single clear waveguide, as with the array of waveguides 122 shown in FIG. 8A, the waveguide 52 can also include more than one waveguides that form an overall waveguide array. Also, it should be noted that the non-fluorescent dyes in the color filters are not in the path of the excitation laser, so the background fluorescence is not a concern.

The above-described COST technology offers significant benefits in system functionality and cost. Further, assuming particular design constraints, the technology also is consistent with satisfactory device throughput. In particular, assuming the entire transverse waveguide area takes 100 um (in width) and the cell travels at 50 cm/s, the time to pass the optical interrogation zone (that is the zone defined by the outermost edges of the outermost waveguides 52, 58 of the additional waveguide structure 50) within the sampling region 40 is 0.2 ms. This limits the detection throughput to 2,000 to 5,000 cells/s or in the order of 10M cells/hr. Although this can be a satisfactory number for some applications, it still falls short in certain other applications. Therefore, to further increase the throughput, it is further proposed that in certain embodiments in-plane lenses to implement the COST design. In such an integrated lens approach, a lens array creates a series of focal spots that are separated by less than 5 um from each other, thus reducing the total width of the interrogation zone to be around 25 microns. As a result, the time to travel through the COST region becomes less than 50 us. This design can potentially increase the throughput to 20-30K/s or about 100M particles per hour.

Depending upon the embodiment, additional structures can be used to further enhance performance of the FACS and/or other flow cytometry designs described herein. For example, in at least some embodiments, prisms and other structures can be used as described for example, in U.S. patent application Ser. No. 12/152,665 filed on May 14, 2008 entitled "System and Method for Flow Cytometry", U.S. provisional patent application 61/068,198 filed on Mar. 5, 2008 also entitled "System and Method for Flow Cytometry", and further U.S. provisional patent application 60/917, 848 filed on May 14, 2007 and entitled "Light Conveying Device", each of which is hereby incorporated by reference herein.

Figure 9:
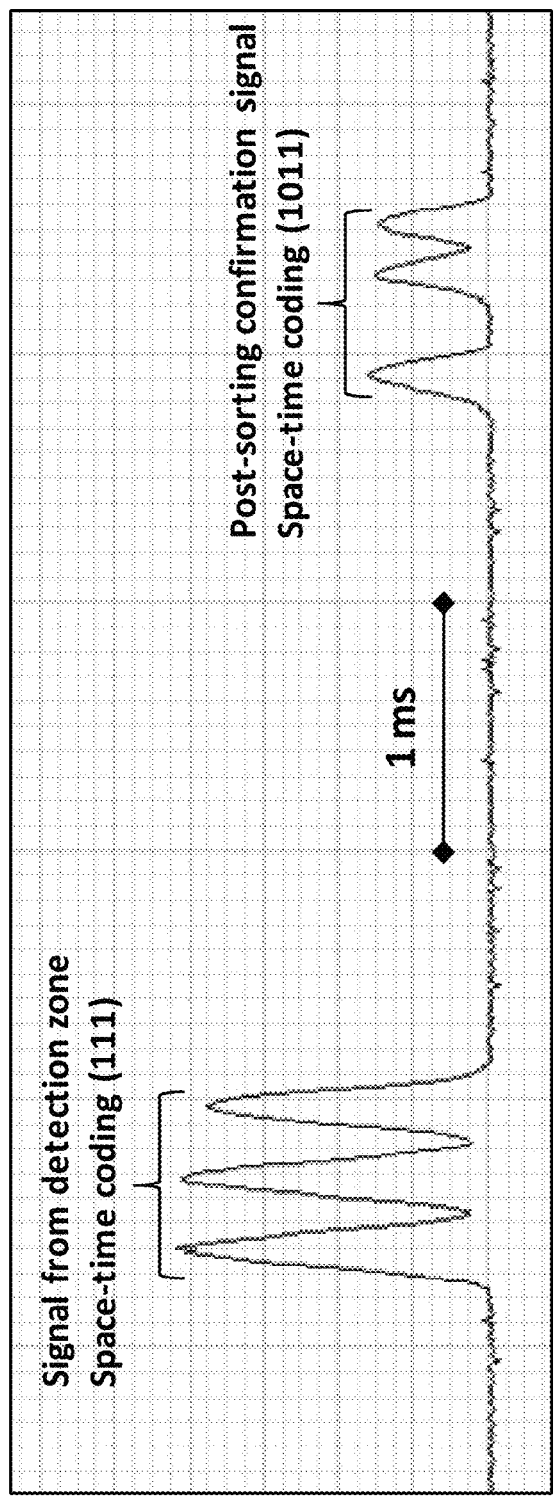
FIG. 9 shows an example of the space-time coding in FIG. 8A.

In FIG. 8A, as the fluorescent cell travels through the channel at a typical speed of 10 cm/s to 100 cm/s, the cell is optically excited along its way in a light-fluid co-propagation configuration. Transverse to the fluidic channel is an array of three apertures that feed their optical transmissions to a single PMT detector. As the cell travels across this array of three apertures, three serial peaks separated by the time of travel are detected, thus converting the space signal (i.e. cell positions) into a time-domain signal. Using a digital match filter to match the waveform of the time-domain signal, the noise in the signal can be suppressed to obtain the travel speed of each individual cell, thus establishing the timing for downstream sorting. If the cell is interrogated multiple times along its path (e.g. oversampling to enhance the signal-to-noise ratio or to verify whether the cell is sorted to the right channel), the coding patterns can be altered so that the resulting time-domain signal at each point of detection can be extracted using a corresponding match filter. FIG. 9 shows that the space-time coded signal (111) at the upstream detection area, followed by another space-time coded signal (1011) downstream after sorting, verifying that the sorting was performed successfully. The first signal (code: 111) represents the detected fluorescence when the bead passes the detection zone. After sorting, the second signal (code: 1011) that is 3.5 ms trailing the first signal indicates that the bead has been correctly switched into the sorting channel.

The multi-parameter on-chip detection and the cell sorting need to function in a well coordinated manner controlled by a real-time electronic system. Sensitivity, latency, and timing jitter are three key issues a good electronic control system needs to address. Sensitivity depends on the quality of the device itself and on the effectiveness of the real-time signal processing capability embedded in the electronic system. Latency is the amount of time required for the algorithms to complete computation. Timing jitter is the variation in latency. The control circuit architecture can be implemented in: (1) analog circuits, (2) microprocessors, or (3) application specific integrated circuit (ASIC). Because of the difficulty in implementing advanced signal processing algorithms in analog circuits and the limited computational power of microprocessors that yields long latency and large timing jitter, the ASIC approach may be implemented for the control circuit. For example, the National Instruments compactRIO system provides a complete embedded system with real-time operating system (RTOS) running on a microprocessor and a field-programmable-gate-array (FPGA), which is basically a highly cost-effective type of ASIC. This system may be used for the control.

The RTOS provides a device driver to access the Ethernet connection chips and the TCP/IP protocol stack for internet communication. This connection is important for data feedback from the compactRIO system and for controlling the real-time hardware. The real-time algorithm can be implemented in the FPGA and the timing jitter is expected to be less than 10 us. In the proposed approach, the electronic control provides the following 3 functions: (1) increasing signal-to-noise ratio (SNR) to improve detection efficiency, (2) instant cell speed estimation to improve sorting accuracy, and (3) sorting signal generation through a waveform generator.

Figure 10:
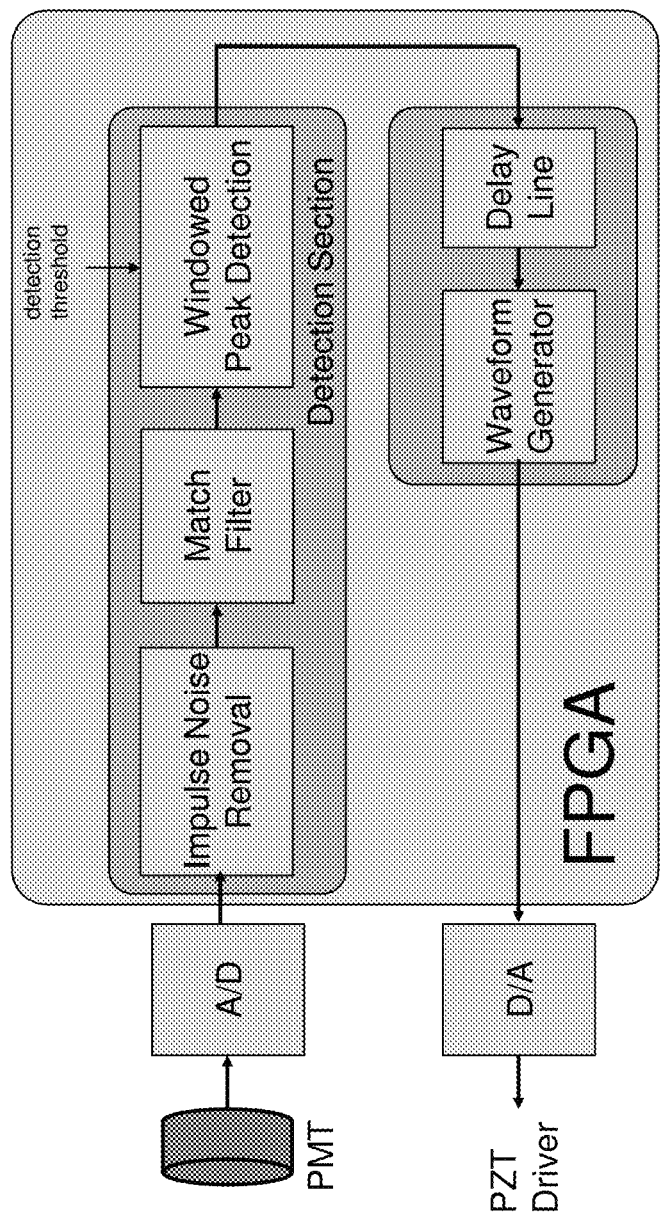
FIG. 10 shows an example of the ASIC architecture of the real-time process control for the FACS device.

The real-time processing control unit shown in FIG. 10 includes the detection section and the control section. In this example, the use of the dedicated hardware for cell detection is to achieve low timing jitter and the control section is to accurately control the timing between the detection of a cell passing and the firing of the actuator with a synthetic waveform to optimize single-cell sorting.

To increase the accuracy of cell detection, three forms of noise that affect the sensitivity can be considered and addressed in designing the detection circuitry: (1) thermal noise of the detection circuit that is nearly white Gaussian noise (WGN), (2) PMT or SPAD dark count noise, and (3) low frequency noise due to laser power fluctuation and stray light. Understanding the characteristics of the noise spectrum, signals can be generated using the aforementioned space-time and COST design so that the signal frequency band has the least overlap with the noise spectrum. Under the WGN condition, the highest S/N ratio can be achieved with the design of match filter, a filter having a response that is the inverse reciprocal of the waveform of the signal. The finite impulse response (FIR) implementation of the match filters is illustrated in FIGS. 11A-11B.

Figures 11A, 11B:
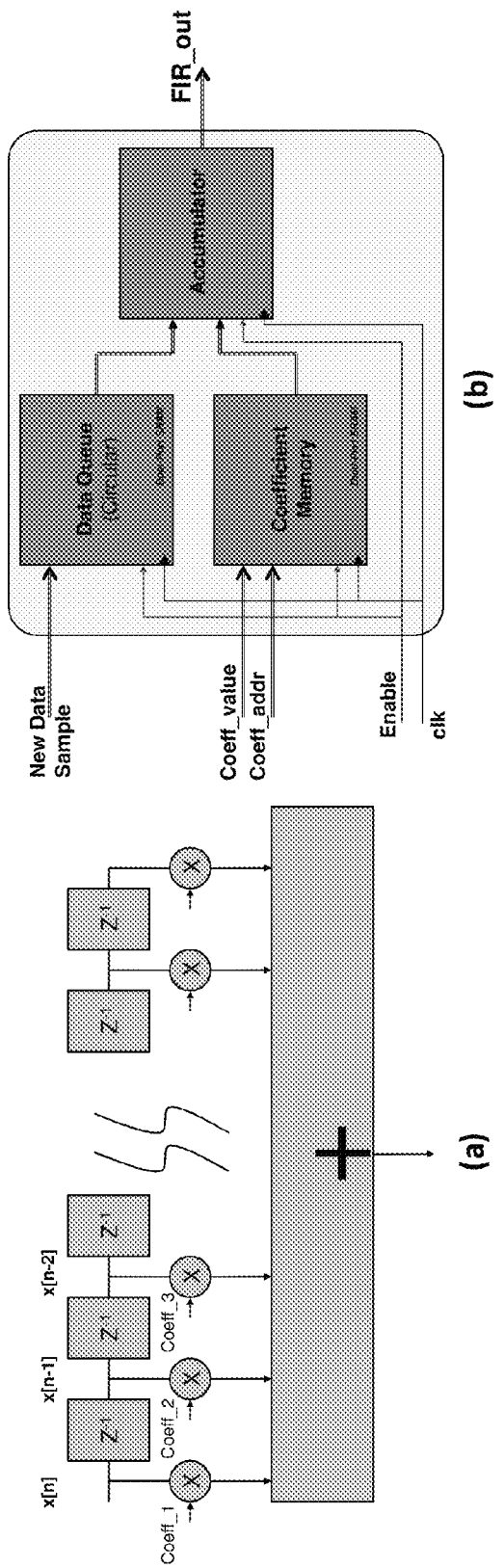
FIGS. 11A-11B show an example of a programmable match filter.

FIG. 11A shows the basic structure of an FIR filter. This is used as a programmable match filter. FIG. 11B shows the hardware implementation of the FIR filter. This design utilizes a special hardware component—dual-port random access memory (RAM), which is a RAM module that can read and write at the same time. Dual-port RAM is a built-in module in Xilinx FPGA. By utilizing the dual-port RAM, a very high sampling rate filter can be achieved.

In some implementation, real-time cell speed estimation can be implemented for high accuracy single-cell sorting. As the speed of the flowing cells changes, the signal generated from the passing cell changes as well. If the cell speed in the microfluidic channel increases, the signal duration becomes shorter. If the speed of each cell varies in a random fashion, the variation of cell speed can be treated as an additional source of noise. It affects both the S/N ratio and the timing jitter. A more effective match filter can be designed based on the knowledge of the speed of each cell and the match filter can be programmed accordingly. The acquired information of cell speed can also be used to adjust the timing control for high accuracy single-cell sorting.

In the frequency domain analysis, variations in cell speed can be treated as variations of the frequency response of the signal. An increase in cell speed adds more high frequency components to the signal, as illustrated in FIG. 12A. Since the frequency spectra for different cell speeds are different, a filter-bank architecture can be used to estimate the flow speed of each individual cell. An example of such architecture is shown in FIG. 12B. For example, a filter bank of 400 FIR filters can be used to measure, in real time, the flow speed from 1 cm/s to 100 cm/s with an accuracy of 0.25 cm/s. FIG. 12C further shows the process for estimating the cell speed based on outputs of the filters in the filter bank.

The signal encoding structures used in FIGS. 3A-3C can be in various configurations in addition to the examples shown in FIGS. 5-8B. FIG. 13A, for example, shows another example of a signal encoding structure that uses optical apertures with different inter-aperture spacings to form different beam patterns as the codes. Two fluidic channels with different optical aperture designs are illustrated to provide two signal codes. FIG. 13B shows the PMT signals from the two channels in the time domain.

Referring to optical filter design for COST coding in FIGS. 5, 7A, 7B, and 8B, the wide-band filtering for the waveguides 54, 56 and 58 is a mechanism to reduce the number of samples required to differentiate color, e.g. the three filter waveguides 54, 56 and 58 can be used to differentiate 20 different fluorescent wavelengths without using 20 filter waveguides. This is a drastic reduction in cost. The single PMT can be used in connection with the three filter waveguides 54, 56 and 58 because time-multiplexing is performed on the information from different wavelengths into the PMT. For instance, in the example in FIG. 8B, the PMT receives the red light via the waveguide 54 first, then green via the waveguide 56, then blue via the waveguide 58. This time multiplexing is by utilizing flow and waveguides (or spatial filters). Time multiplexing with wideband filtering allows us to have high-throughput color detection.

Figure 14:
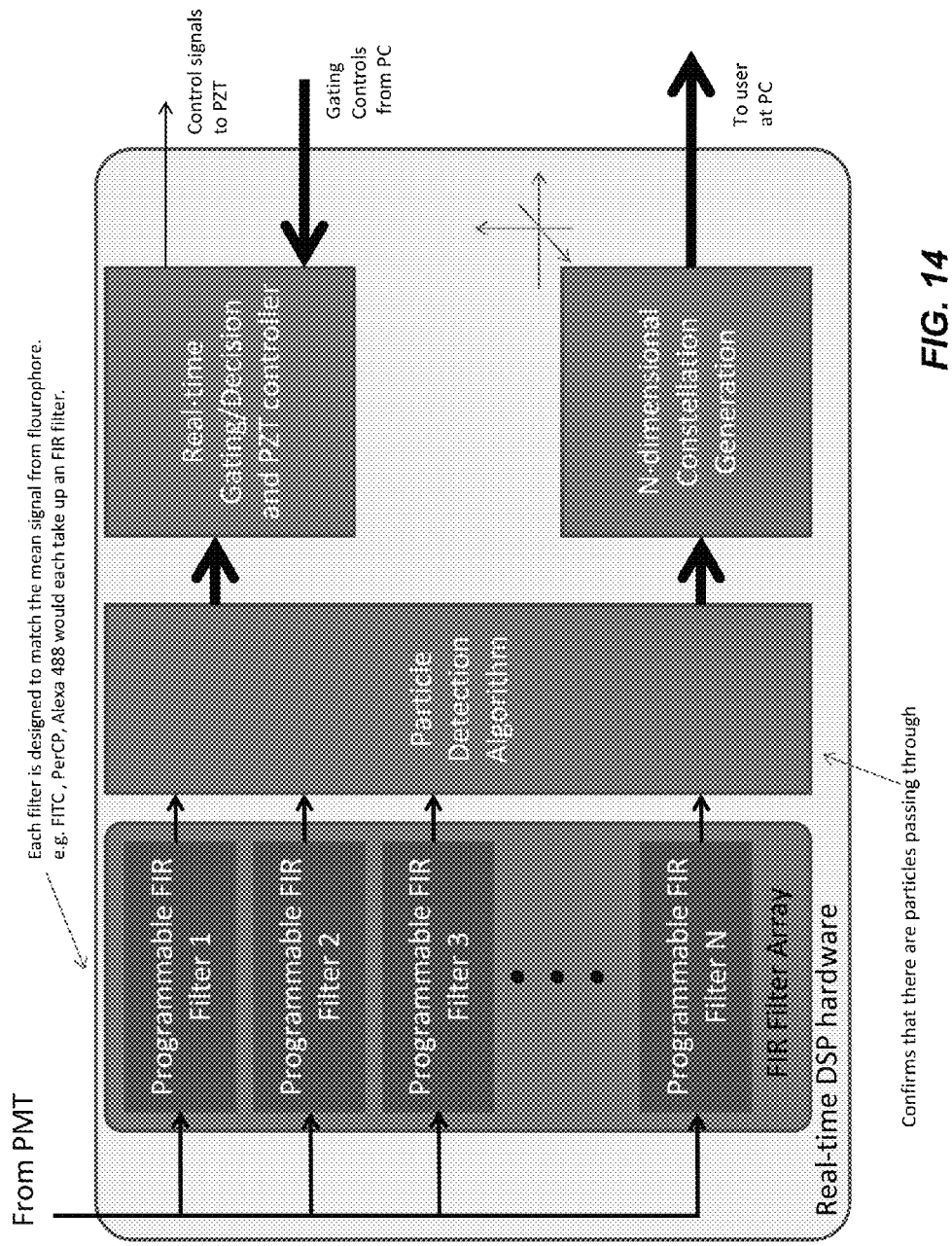
FIG. 14 shows an example of DSP processing block based on programmable FIR filtering bank.

FIG. 14 shows an example of DSP processing block based on programmable FIR filtering bank.

The particle sorting mechanism in flow cytometry devices and systems can be implemented in various configurations. The following sections provide a particle sorter based on a piezoelectric actuator which can be configured to operate with low voltage (typically less than 10 $V_{p\text{-}p}$), having low power requirements (typically less than 0.1 mW), and having a fast response time of approximately 0.1-1 msec with particle flow speeds of approximately 1-10 cm/sec. The particle sorting system is operable in a closed loop manner using a spatial filter and processing techniques for determining the presence of a particle by analyzing a light signal over time, which signal is output by a detector.

Figure 15:
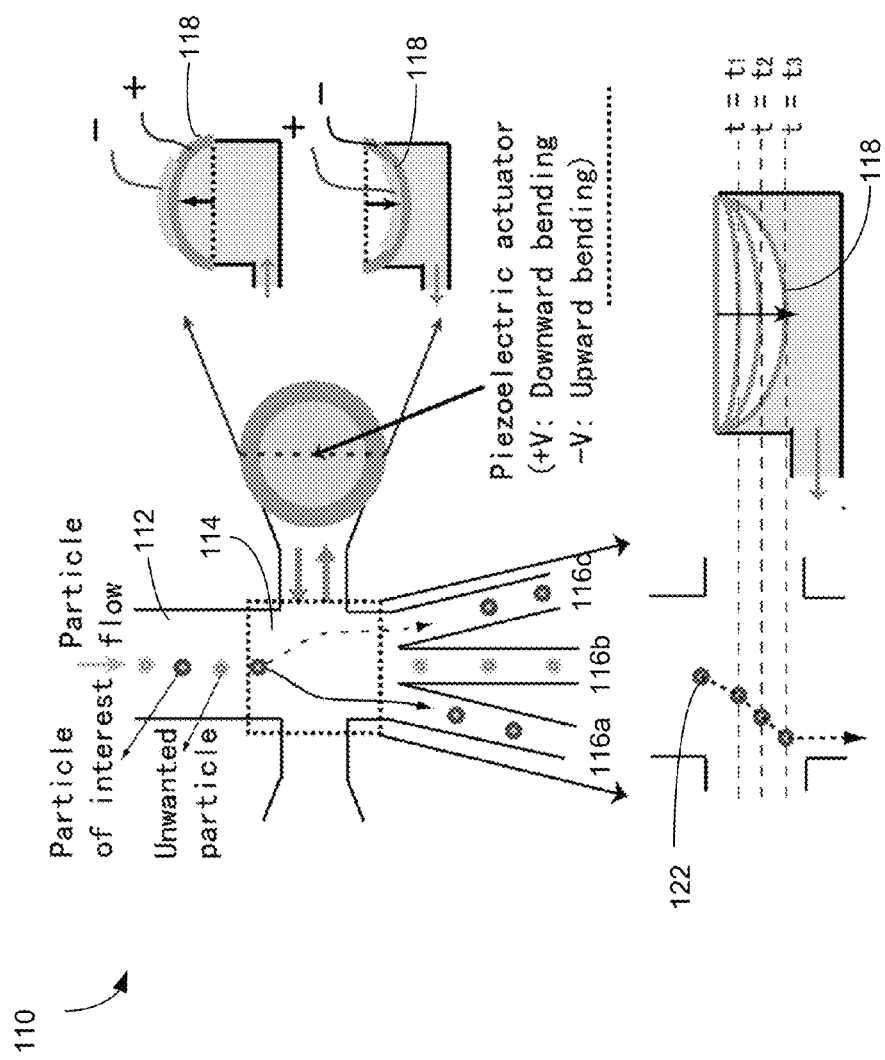
FIG. 15 illustrates a particle sorter and its operation in accordance with at least one exemplary embodiment.

Referring to FIG. 15, illustrated is a particle sorter 110 for sorting particles in a fluid. The particle sorter 110 includes an input channel 112 connected at an actuation area 114 to a plurality of output channels 116a, 116b, and 116c. Particles flow through the input channel 112 to the actuation area 114, and each particle travels from the actuation area 114 to one of the plurality of output channels 116a, 116b, 116c.

A piezoelectric actuator 118 operates to cause a flow disturbance to fluid in the actuation area 114 in response to a control signal such as a voltage control signal from a controller or driver as illustrated in FIG. 1. For example, as illustrated a positive voltage signal applied to the piezoelectric actuator 118 causes downward bending, and a negative voltage signal causes upward bending. This bending causes a flow disturbance in the actuation area 114, specifically by causing a transverse displacement of fluid (on the order of nanoliters). The flow disturbance directs a particle entering the actuation area along a trajectory to one of the output channels 116a or 116c, which is different than the output channel 16b to which the particle would travel without the flow disturbance. For example, as illustrated in the lower portion of FIG. 15, a positive voltage applied results in downward bending of the piezoelectric actuator 118, causing a flow disturbance in actuation area 114 causing a particle 122 to alter its trajectory and travel to the left and to output channel 116a.

Figure 16A:
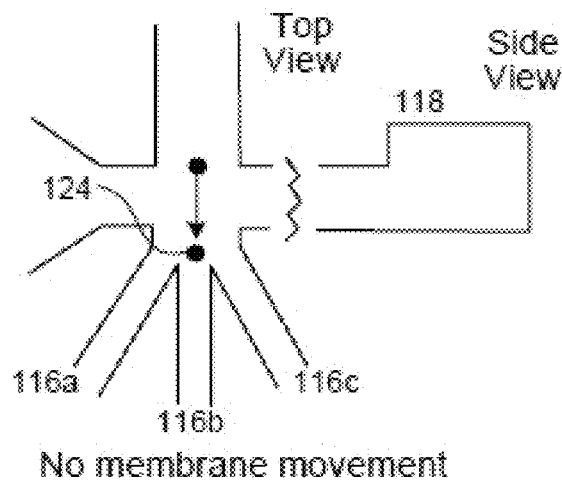
FIGS. 16A-16C further illustrate the operation of the particle sorter of FIG. 1.
Figure 16B:
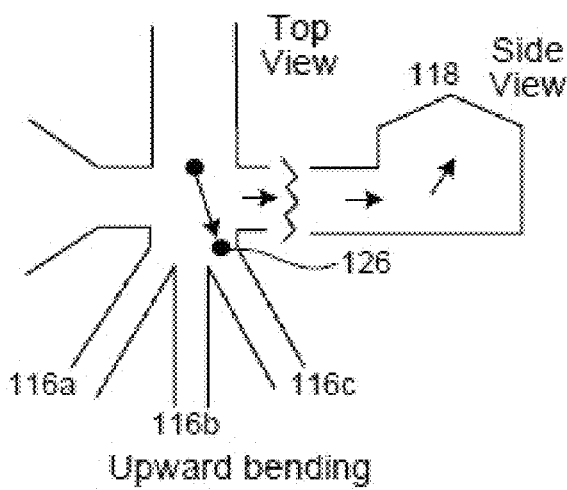
Figure 16C:
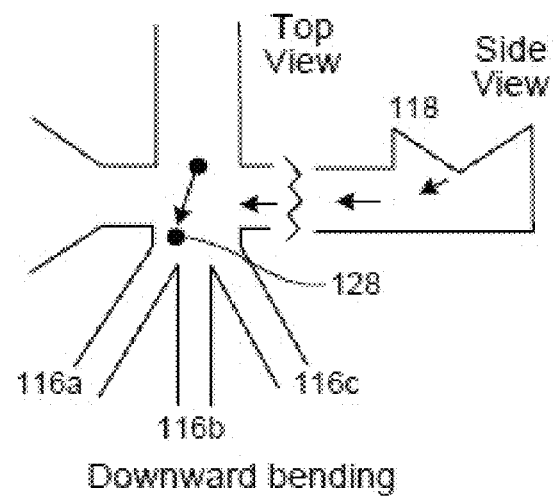

More completely, FIG. 16A illustrates travel of a particle 124 when there is no control voltage signal applied, showing travel of the particle to output channel 116b. FIG. 16B shows travel of a particle 126 to output channel 116c in response to application of a negative voltage signal. Similarly, FIG. 16C shows travel of a particle 128 to output channel 116a in response to application of a positive voltage signal.

FIGS. 17A-17C illustrate the simple, low cost fabrication of particle sorter 110, which is accomplished by UV ozone bonding together an etched polydimethylsiloxine (PDMS) substrate 130 and a glass substrate 132. The PDMS substrate 130 has been etched to form the input channel 112, output channels 116a, 116b, 116c, and actuation area 114. Specifically, the PDMS substrate and glass substrate are surface treated in a UV ozone chamber with a lamp output of 28 mW at 254 nm, and bonding occurs as the substrates 130, 132 physically contact each other.

The piezoelectric actuator is formed using a first layer 136 such as stainless steel or copper and a second layer 134 such as lead zirconate titanate. Lead zirconate titanate has a chemical formula of $Pb[Zr_xTi_{1-x}]O_3$, where $0<x<1$, and is a ceramic perovskite material that shows a marked piezoelectric effect. It is also known as PZT which is an abbreviation of the chemical formula. Contact pads 38 are provided for application of the control signal across the two layers.

The piezoelectric actuator 118 is integrated with the PDMS substrate by first forming a hole in the PDMS substrate, such as by using a 16 mm diameter punch, and then both the PDMS substrate and the piezoelectric actuator 118 are UV ozone treated for another five minutes. The actuator is then aligned and brought into contract with the PDMS substrate 130, and the sorter 10 is then baked at 85 degrees C. for 8 hours.

Figures 18A, 18B, 18C:
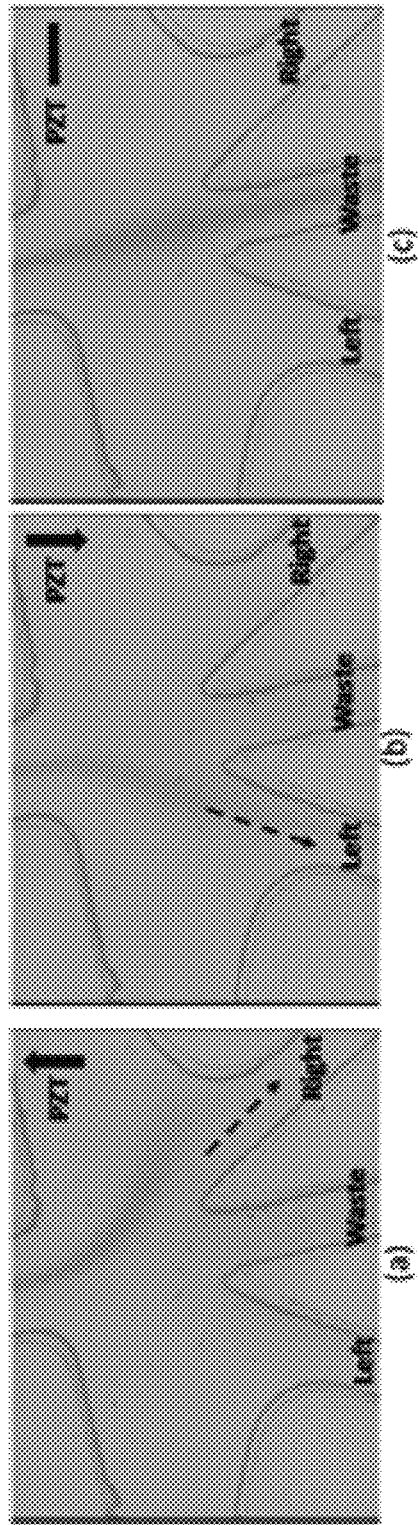
FIGS. 18A-18C show deflection of rhodoamine in the particle sorting system of FIG. 1.

FIGS. 18A-18C illustrate the capability of the particle sorter for sorting particles, and shows the deflection of rhodamine caused by the instantaneous finite fluid displacement in the actuation area. In particular, the sorter 110 is mounted on a microscope stage with a high-speed video camera attached for visualization, and the control signal to the piezoelectric actuator 118 is provided by a function generator. Fluid with rhodamine is introduced to the channel, a 250 Hz, 9 V p-p voltage signal provided, and video obtained.

Figure 19A:
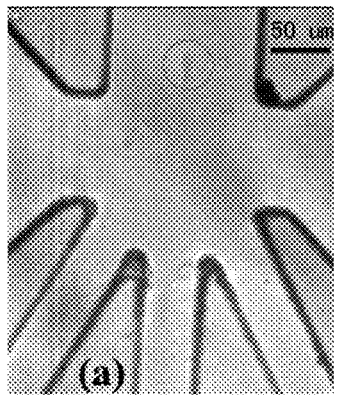
FIGS. 19A-19F show experimental and simulated trajectories of beads.
Figure 19B:
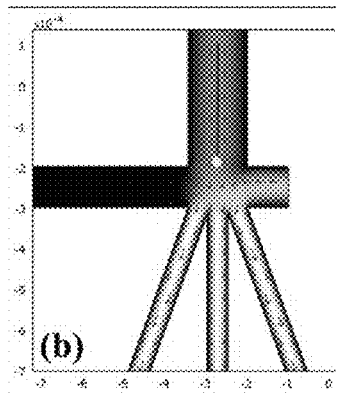
Figure 19C:
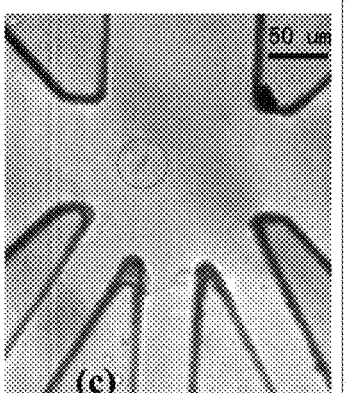
Figure 19D:
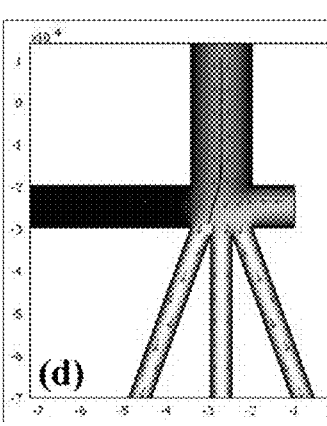
Figure 19E:
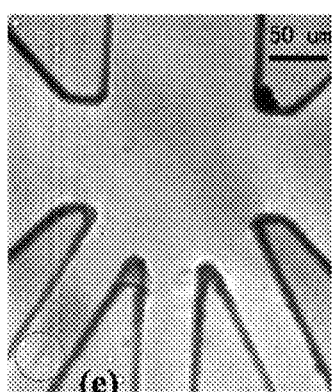
Figure 19F:
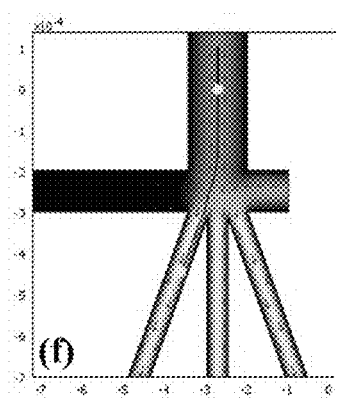

FIGS. 19A-19C illustrate sequential positions of a polystyrene bead obtained experimentally, and FIGS. 19D-19F illustrate the simulated trajectory of a bead using the incompressible Navier-Stokes equation shown.

Figure 20:
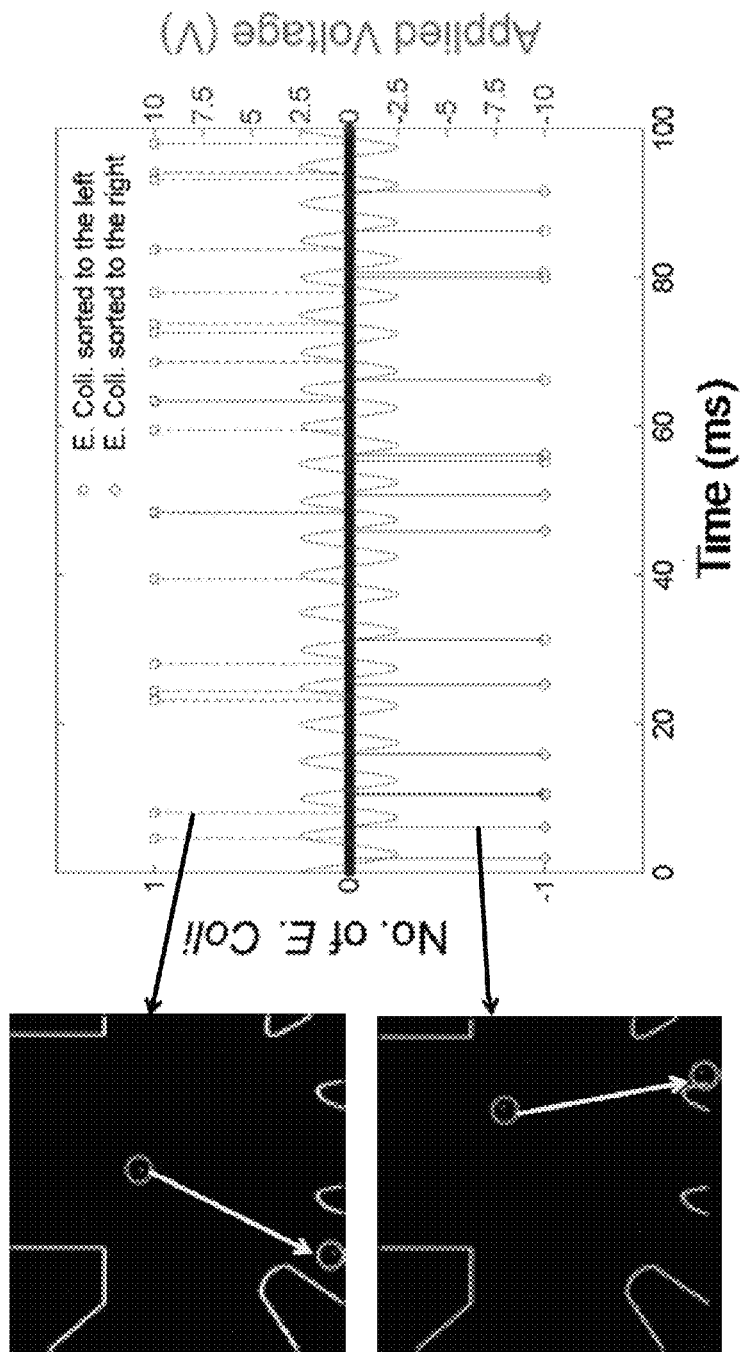
FIG. 20 illustrates the deflection of E. coli cells subjected to a sinusoidal input voltage as a control signal.

FIG. 20 illustrates the sorting of *E. coli* cells subjected to a sinusoidal control voltage signal at 6 Vp-p at 200 Hz.

Figure 21:
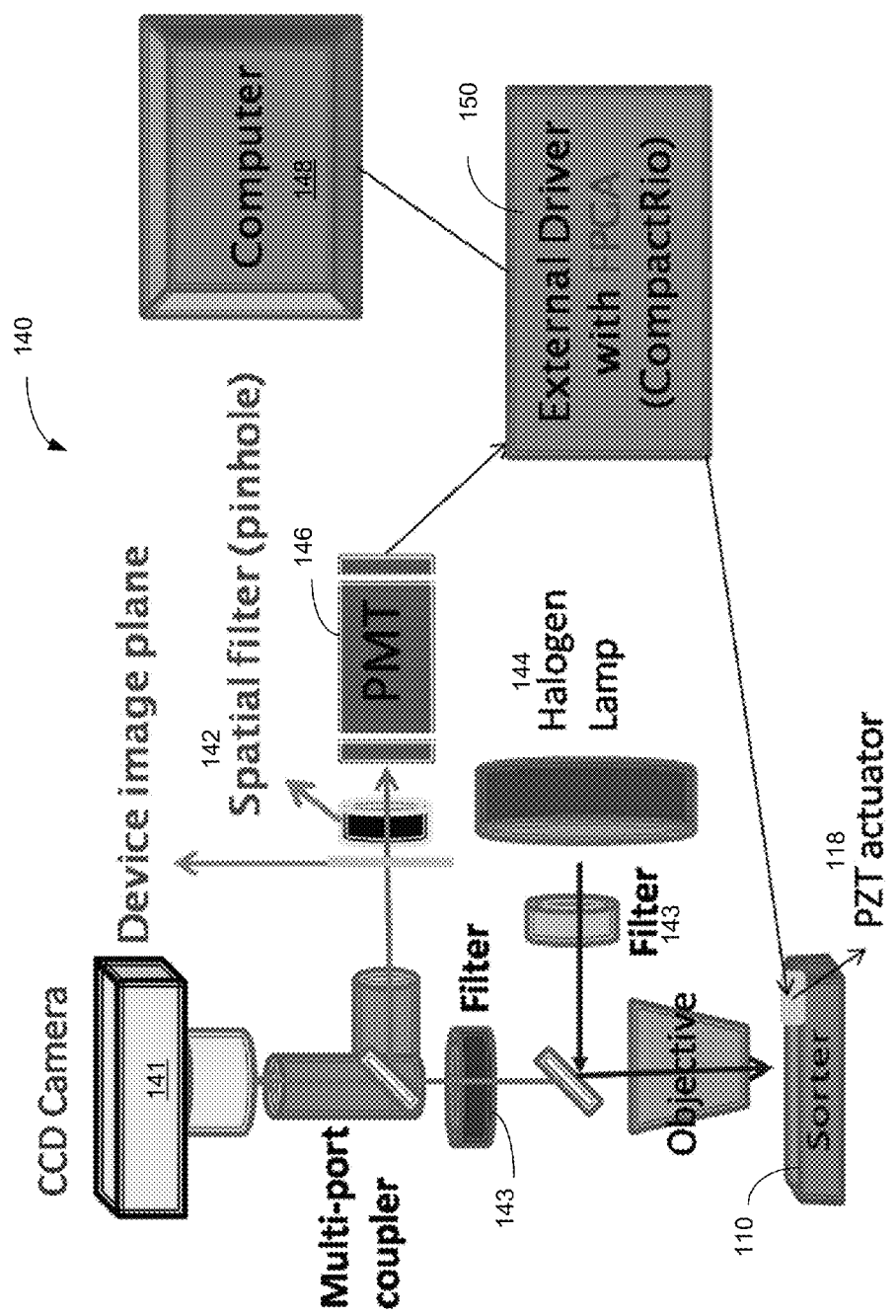
FIG. 21 illustrates a particle sorting system having closed loop control.

FIG. 21 illustrates a closed loop particle sorting system 140, including particle sorter 110, which operates in a closed loop manner to sort particles of interest from other particles in a fluid. A camera 141 for visualization is provided. The particle sorting system also includes a spatial filter 142 (see FIG. 22) having one or more slots and coupled to the input channel, as well as one or more optical filters 143. A light source 144, such as a halogen light, provides input light to the input channel. A detector 146 detects light emitted or scattered from a particle of interest in the input channel, which light has passed through the one or more slots of the spatial filter 142, and provides a detection signal over time. A processor and driver 150, having one or more components implements as a field programmable gate array (FPGA), is in communication with the detector 146 and operates to analyze the detection signal over time. The processor and driver 150 can be in communication with a computer 48 for receiving user input. The processor and driver 150 also generates a presence signal indicative of the presence of a particle of interest passing a predetermined location in the input channel, and generates the control signal for the piezoelectric actuator 118 in response to the presence signal. As described above, the piezoelectric actuator 118 causes a flow disturbance in the actuation area in response to the control signal, wherein the flow disturbance operates to direct a detected particle of interest along a trajectory to one of the plurality of output channels which is different than the output channel to which the particle would travel without the flow disturbance.

Figure 22:
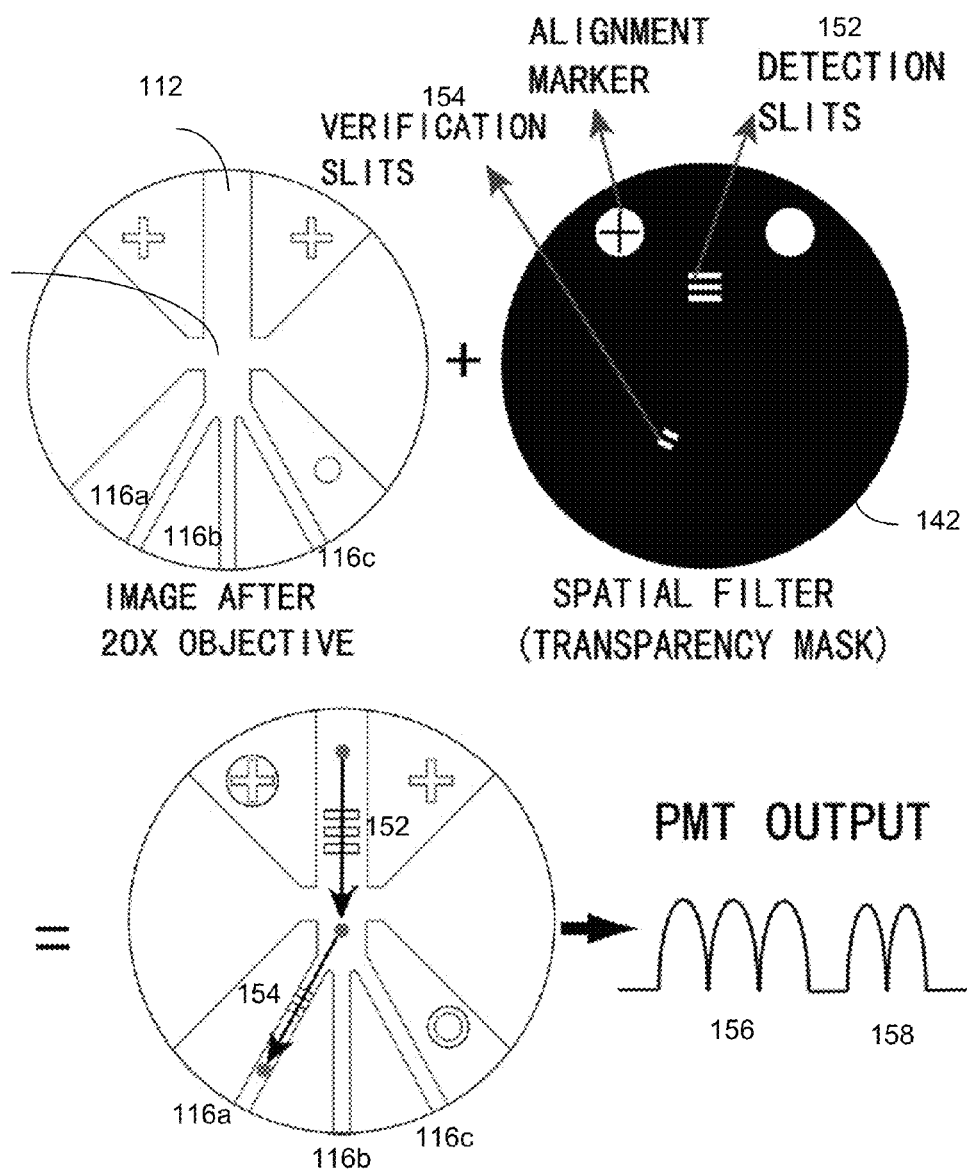
FIG. 22 illustrates a spatial filter for the particle sorting system of FIG. 21.

As shown in FIG. 22, the spatial filter 142 includes a plurality of detection openings or apertures 152 which can be aligned with the input channel 112, and which each allow light from a particle of interest through to the detector 146. The spatial filter 142 can also include a plurality of verification openings 154 aligned with one of the output channels, such as 116a. When a particle of interest travels past the detection openings 152, a signal 156 having an expected pattern (based on flow rate) is produced. This signal can be processed using digital signal processing (DSP) techniques to determine when a particle of interest is present in the input channel. Various DSP techniques can be used, including noise filtering to reduce noise, a finite impulse response filter, or banks of filters. When a particle of interest is present in the input channel, a control signal can be generated, which may need to be delayed so that the flow disturbance occurs when the particle of interest is at an appropriate location in the actuation area 114. Verification that the particle of interest has actually traveled to the desired output channel 116a can be obtained by checking that the signal 158 is obtained following signal 156.

The above spatial filter in FIG. 22 is an exemplary encoding structure in FIGS. 3A and 3B. The spatial filter allows only fluorescence from certain areas in the channel to reach the detector, thus cutting down the background and crosstalk. Each of the specially designed patterns 152 and 154 spatially encodes a fluorescent signal which is transformed into a temporarily encoded signal as the targeted particle/cell travels at a speed. Photolithographic transparency masks (Cad/art services, Inc.) can be used to create spatial filters. The spatially encoded patterns have triple slits (152) and double slits (154). The triple slit pattern (152) encodes the detection signal and the double slit pattern (154) the verification signal from the particles/cells sorted into the designated channel. In the sample spatial filter, the width of the slits is 0.25-0.5 mm, translated to 12.5-25 μm on the microfluidic channels before magnified by a 20× microscope objective. The spatial filter is designed to purposefully coincide with the image plane after magnification. As fluorescent particle passes through detection slits and gets sorted down to the verification slits, the PMT detector is expected to register signals of 3 peaks followed by 2 peaks.

Figure 23:
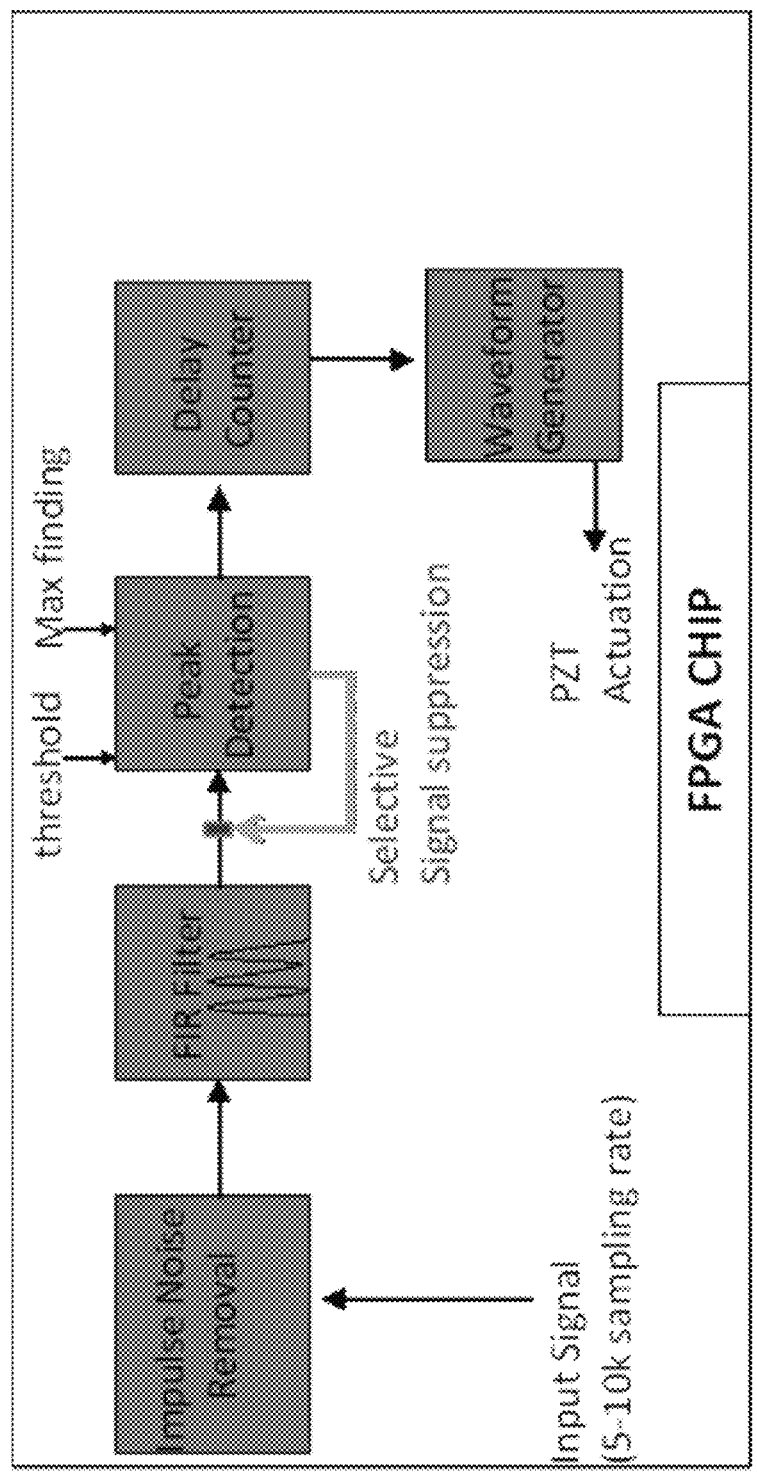
FIG. 23 is a block diagram showing operation of control circuitry for the closed loop system of FIG. 21.
Figure 24:
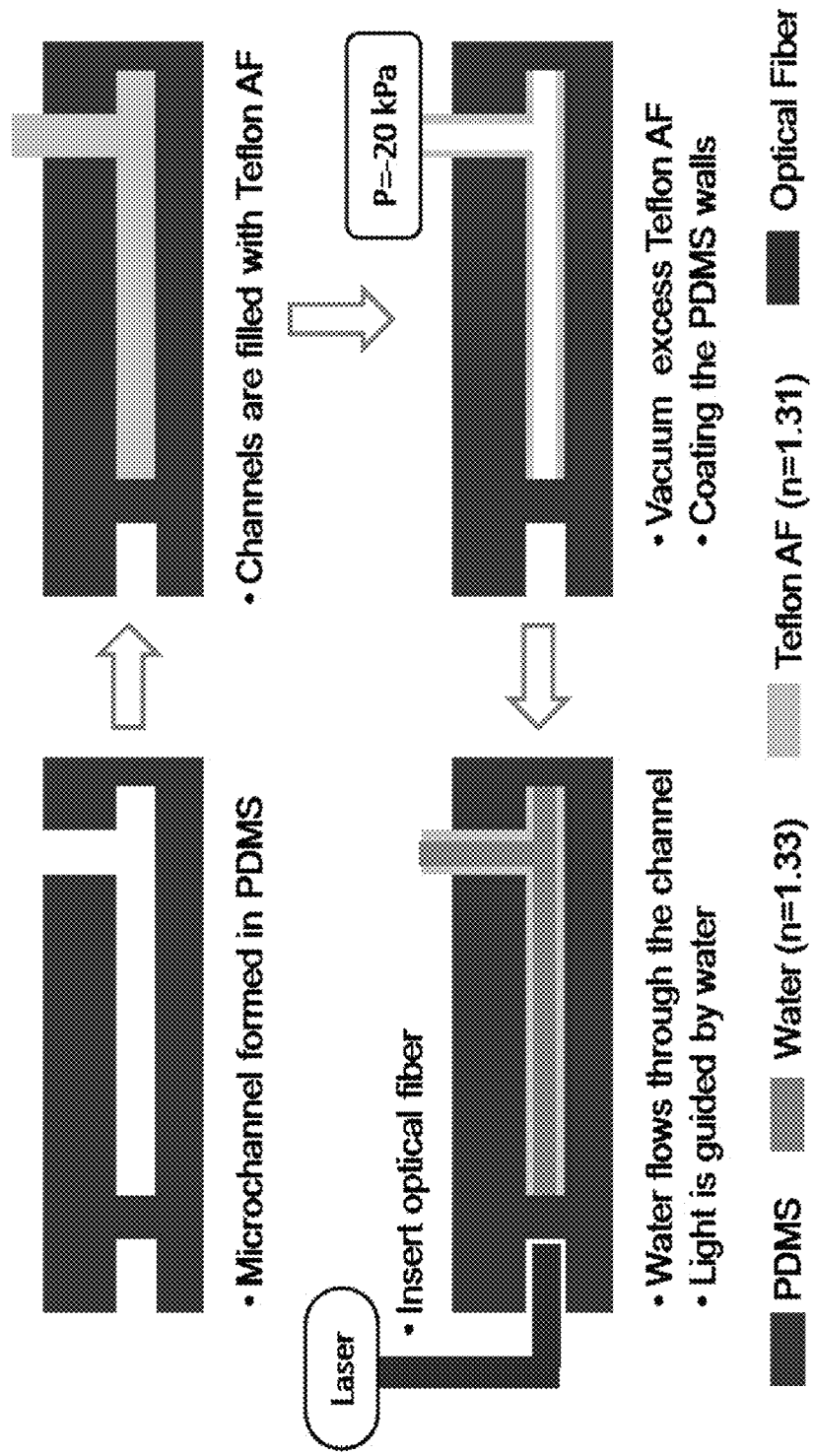
FIG. 24 shows an example of a fabrication process for Teflon AF coated fluid core waveguides. This process reduces the elastic mismatch between PDMS and Teflon AF.

FIG. 23 is a block diagram of one implementation of processor and driver 150, showing the process flow of the electronics control algorithm. The algorithm is programmed into the FPGA chip embedded in the external driver. For example, real-time electronic control is programmed using Labview (National Instrument) with a programmable external driver (CompactRio, NI). The external driver has an independent operating system with an embedded field-programmable gate array (FPGA) chip. The measured jitter of the system is less than 10 μsec. The random high pulse noises of PMT (e.g. caused by sporadic discharge of the device) are removed before running the signal amplification algorithm based on finite impulse response (FIR) filtering. With an FIR matched filter, the signal-to-noise (SNR) ratio can be increased by 18 dB. After SNR enhancement, threshold and search of maximum signal criteria are applied to determine the presence of the detected particle. A signal above threshold indicates that a particle/cell to be sorted is found, triggering the following actions: (a) a delay counter delays the firing of the pulse generator, (b) a preprogrammed output voltage signal is fired to drive the PZT actuator, (c) at certain time period the system is ready to detect the "verification" signal from the sorted sample traveling through the "verification zone", and (d) update record of the sorting efficiency and sorting error. The amount of time delay equals the travel time of the particle from the optical detection zone to the sorting junction. Until the sorted particle is verified, the PZT actuator will not be fired again. This avoids the problem of confusing the verification signal with the signal of particles traveling too close to the particle being sorted.

FIGS. 24-27 illustrate an exemplary method for fabricating optofluidic waveguide that is compatible with polydimethylsiloxane (PDMS). The light path follows the microfluidic channels, an architecture that can maximize detection efficiency and make the most economic use of chip area in many lab-on-chip applications. The PDMS based microfluidic channels are coated with Teflon amorphous fluoropolymers (Teflon AF) which has a lower refractive index (n=1.31) than water (n=1.33) to form a water/Teflon AF optical waveguide. Driven by a vacuum pump, the Teflon AF solution was flowed through the channels, leaving a thin (5 to 15 mm) layer of coating on the channel wall as the cladding layer of optical waveguides. This coating process resolves the limitations of spin-coating processes by reducing the elasticity mismatch between the Teflon AF cladding layer and the PDMS device body. We demonstrate that the resulting optofluidic waveguide confines and guides the laser light through the fluid core channel. Furthermore, the light in such a waveguide can be split when the fluid flow is split. This new method enables highly integrated biosensors such as lab-on-chip flow cytometers and micro-fabricated fluorescence-activated cell sorter (mFACS) with on-chip excitation Optofluidics is an emerging field that integrates microfluidics and optics on the same device to work synergistically. Devices that contain both microfluidic channels and on-chip photonic circuits, such as integrated biochemical sensors, show enhanced functionality and sensitivity and enable significant cost and size reduction. In order to assure that photons and biological samples in the fluid interact most effectively for the highest sensitivity, however, we desire the flexibility to direct and align the paths of light and fluid. In some cases, we need light beams to intersect the fluidic channels to localize the interrogation area. In other cases, we want the light wave and the fluid to share the same path to maximize their interaction. For the latter case, we still lack an effective fabrication method. Due to the fact that most polymers used in lab-on-a-chip devices have a higher index of refraction than water, light traveling in the fluidic channel will not be confined, suffering from high radiation loss. A PDMS-compatible process is provided here for coating microfluidic channels with a layer of low refractive index Teflon AF solution, enabling the water in the fluidic channel to be used as the waveguide's high index core. The Teflon AF coated waveguide works not only for straight fluidic channels but also for split channels. In addition to delivering the light, by Teflon coating the microfluidic channel, a channel is created with low sample adsorption, avoiding a troublesome problem found in many polymer-based microfluidic devices.

Teflon AF is an amorphous fluoropolymer that is chemically stable and optically transparent from UV to IR wavelengths. Unlike other fluoropolymers, Teflon AF has a refractive index (n=1.31) that is lower than the index of water (n=1.33), therefore a Teflon AF coating layer can be used to clad a fluid-core optical waveguide. Light will then be delivered through the same physical path as the fluid flows by total internal reflection (TIR) when the coated channels are filled with water or aqueous solutions. A procedure for coating Teflon AF onto PDMS channel walls is provided here by flowing Teflon AF solution through the micro channel, thereby creating the cladding layer for an optical waveguide along the path of fluid flow. The light introduced to micro channels is confined inside the core of the waveguide (i.e. microfluidic channel) and guided by fluid flowing through the channel.

Microfluidic channels that are 200 mm by 70 mm are fabricated in PDMS. A master mold is lithographically defined on an optically smooth Si wafer using SU-8 50 (MicroChem). Two replicas are created: one replica with microfluidic channels and one replica of an optically smooth blank Si wafer. A solution of 2% 1H,1H,2H,2H-perfluorodecyltriethoxysilane (Sigma Aldrich Inc.) is spin-coated onto PDMS substrates and heated at 110° C. for 10 minutes to promote adhesion between PDMS and the Teflon AF solution. Both PDMS surfaces are then activated for permanent bonding by UV/Ozone treatment (UVO-CLEANER 42, Jelight Inc.) for 3 minutes and bonded together, thus capping the microfluidic channels. A 6% Teflon AF solution (601-S2, DuPont Corp) is flowed into the microfluidic channels. Once they are filled, vacuum (P=−20 kPa) is applied for 20 minutes to remove excess Teflon AF solution from the channels (see FIG. 24.). The balance between the vacuum force and the adhesion to the PDMS channel wall determines the thickness of the cladding layer.

The process results in a smooth channel with a hollow core. The Teflon AF-coated PDMS device is heated to 155 degrees C. for 20 minutes to evaporate the fluoroinert solvent, and then heated further to 175 degrees C. (15 degrees C. above the its glass transition temperature) for 20 minutes to form a smooth Teflon AF layer. This relatively low temperature coating is compatible with PDMS process while significantly reducing the consumption of Teflon solution compared to the spin-coating process. Calculations show that a ~5 mm thick Teflon AF film is necessary to confine the light to the fluid core. In some implementations, the cladding thickness is typically 5 to 15 mm, thick enough to confine and guide light waves. The thickness of the Teflon AF coating layer can be further controlled by adjusting the applied vacuum pressure and concentration of the Teflon AF solution. After slowly cooling the devices to avoid cracking due to thermal mismatch, an optical fiber is inserted into the channel for light coupling. Deionized (DI) water is then introduced into the hollow core to serve as both the sample flow carrier and the core of the optofluidic waveguide.

Figure 25:
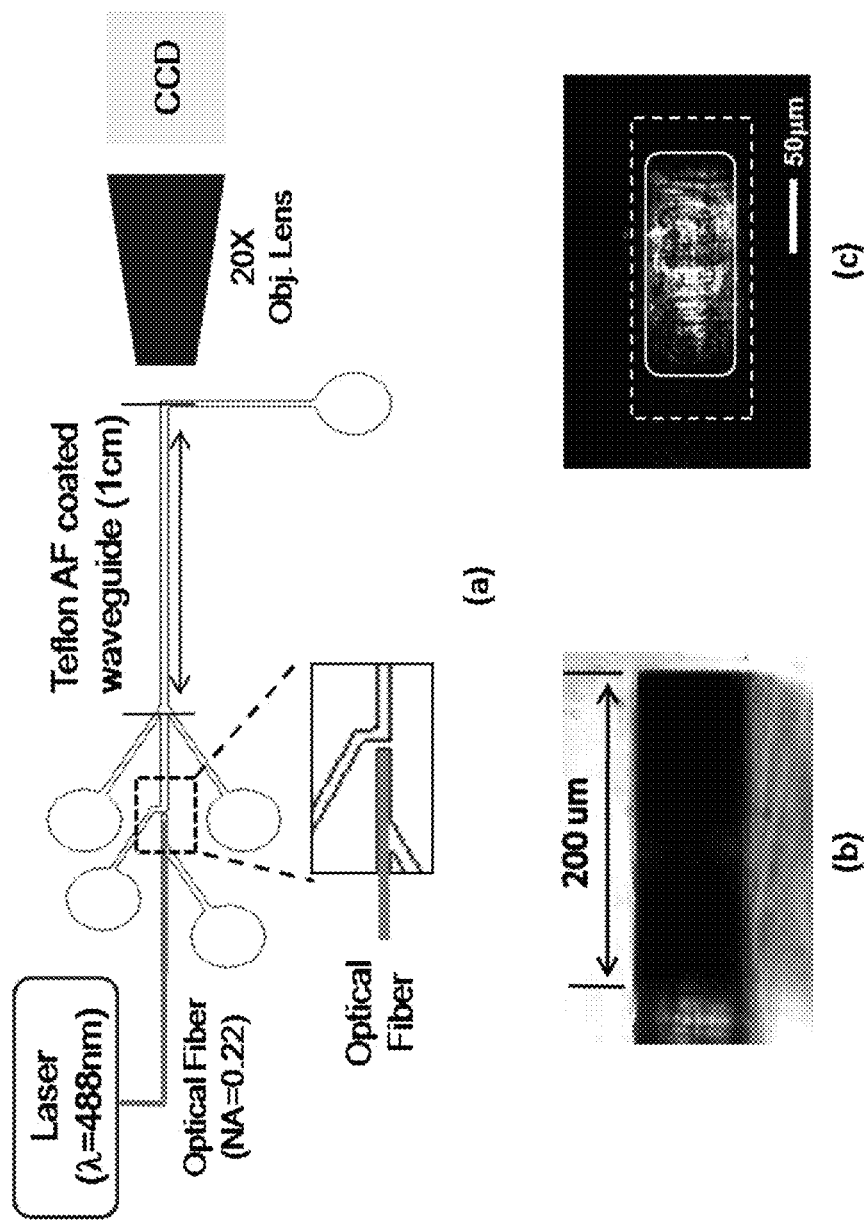
FIG. 25 shows an experimental setup for light output measurement, the cross section of the fluid core waveguide, and the light output from a fluid core waveguide with Teflon AF coating. The dotted box is the perimeter of the channel, and the solid line is the Teflon AF coated core layer.

The flowing DI water transports both the suspended samples and the light in the same channel. FIG. 1 illustrates the fabrication process of the Teflon AF coated optofluidic waveguide. The numerical aperture, NA=$(n_{core}^2 - n_{cladding}^2)$ 1/2, of the fluid core waveguide is 0.23; well-matched to the NA of the input multi-mode fiber (NA=0.22). The cross section of the fluid core waveguide is imaged by a charged coupled device (CCD) at the end of the channel as shown in FIG. 25 (a). FIG. 25 (b) shows the cross section of the fabricated microfluidic channel that is 200 mm by 70 mm. FIG. 25 (c) shows the light output of the optofluidic waveguide when the laser is on. The dotted box shows the wall of the PDMS channel, and the solid line shows the boundary between the Teflon AF cladding layer and the fluid core. It verifies that the light is confined to the fluid core of the optofluidic waveguide by the Teflon AF coating. A waveguide loss of 2.13 dB/cm at 488 nm wavelength is measured. Scattering is the dominant factor compared to light leakage and absorption. With improved smoothness of Teflon AF coating, we believe the waveguide loss can be reduced significantly.

Figure 26:
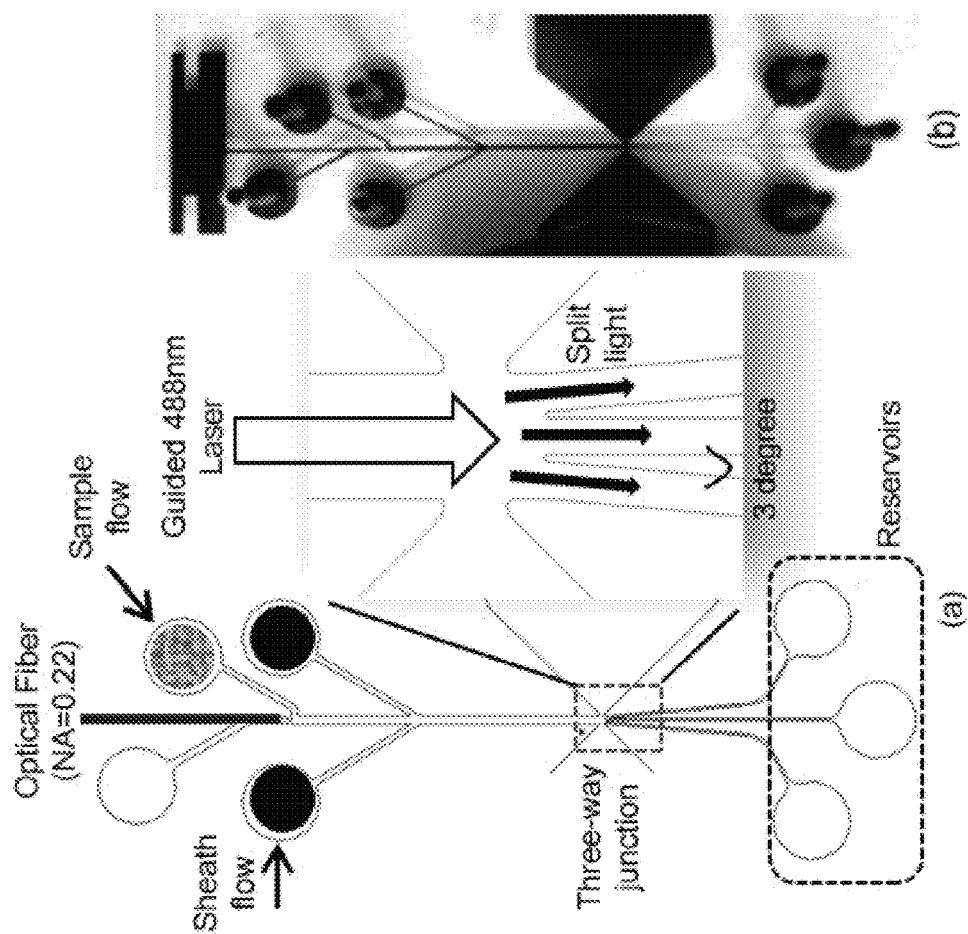
FIG. 26 shows the layout of the device where light can be split and guided at the 3-way junction, and a photograph of the device fabricated in PDMS.

FIG. 26 (a) shows the layout of a microfluidic channel which includes a splitting junction, and FIG. 26 (b) is a photograph of the device. Laser light (1=488 nm) is fiber-coupled into the microfluidic channel, in which water flows. Light is guided by the fluid flow, and at the three-way junction, as shown in the enlarged box in FIG. 26 (a), the 488 nm light is divided into three paths following the fluid flow towards the channel outlets. In order to demonstrate that light can be split and guided through three channels, we have filled the device with a diluted Rhodamine 6G solution that emits green fluorescence in all directions after absorption of the guided 488 nm light.

Figure 27:
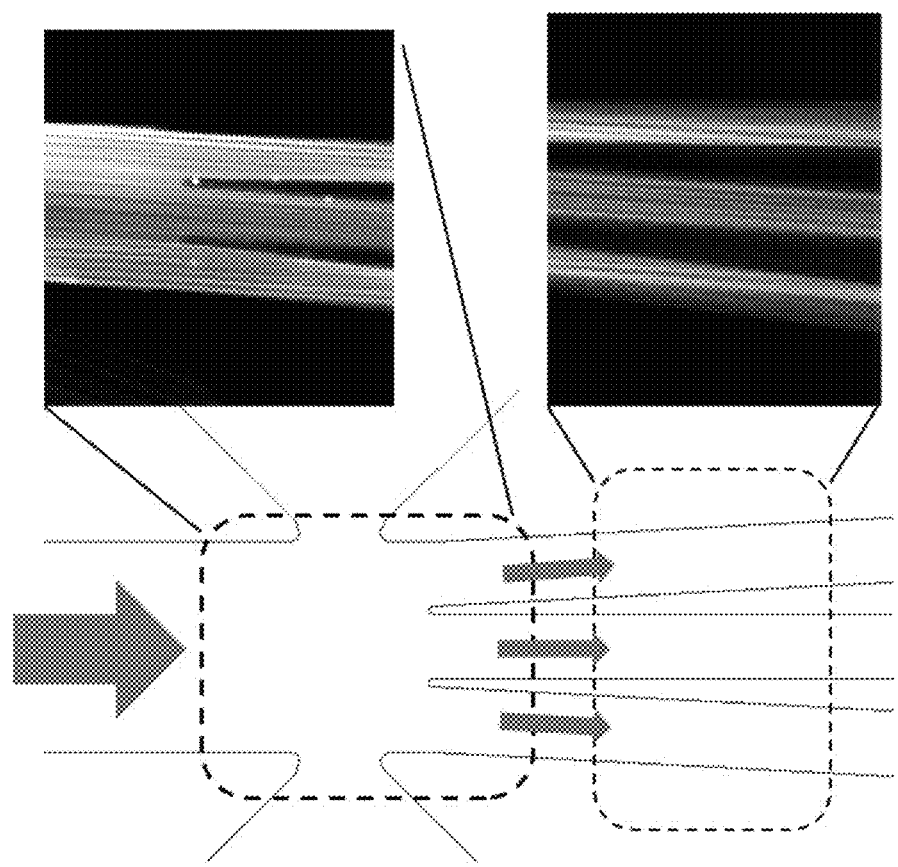
FIG. 27 shows the light emitted by Rhodamine 6G when the fluorescent dye in the fluid is excited by the 488 nm laser light sharing the same paths as the fluid. The 488 nm input light is guided through the entire paths of fluidic channels, even after the three-way split.

As shown in FIG. 27, the light guided from the upstream channel is divided into three split channels separated by 3-degrees. The result demonstrates that the excitation light is split into three channels and that the split light is still guided through the channels. Since the light always traces the fluid flow in which samples are suspended, excitation is performed at all locations, and thus detection can be performed at any position. This unique property provides a very convenient feature for lab-on-a-chip devices. For example, it becomes possible to perform highly sensitive fluorescence detection at multiple locations using only a single light source, imparting a high degree of design flexibility to miniaturized optofluidic devices, for example, lab-on-chip flow cytometers or micro-fabricated fluorescence-activated cell sorter (mFACS).

Figure 28:
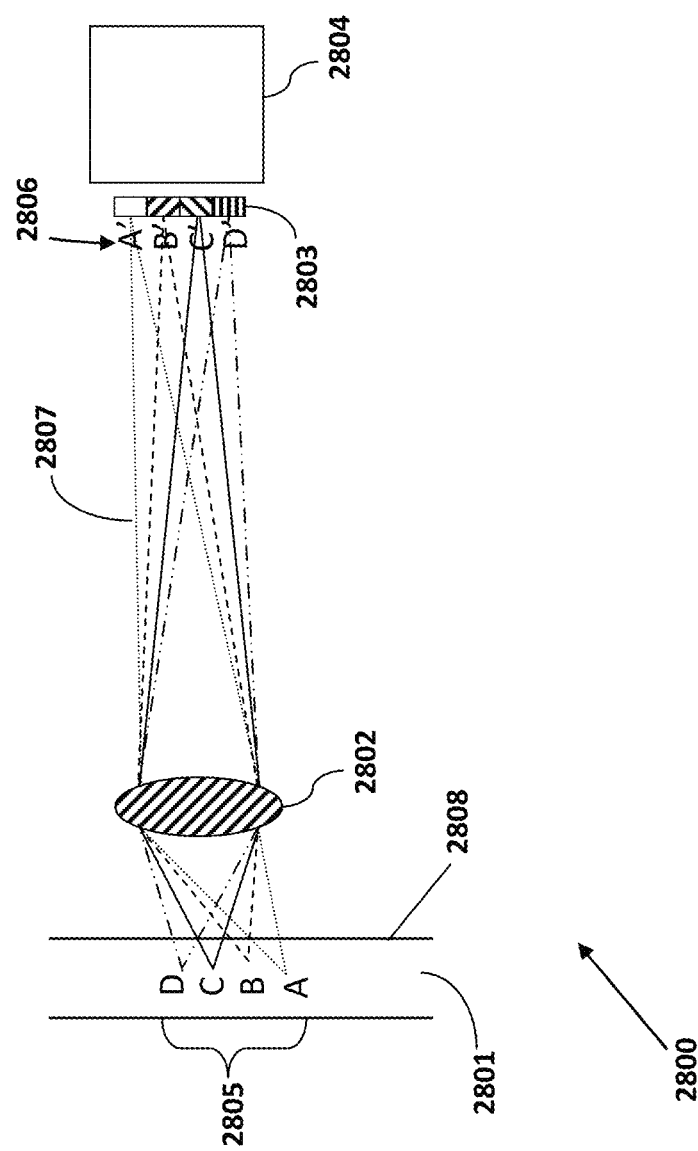
FIG. 28 is a schematic illustration showing an embodiment of a device used for flow cytometry or fluorescence-activated cell sorting (e.g. a non-limiting example of a COlor-Space-Time (COST) coding operation) illustrating a specific configuration of a lens.

Shown in FIG. 28 is a schematic illustration showing an embodiment of a device used for flow cytometry or fluorescence-activated cell sorting (e.g. an example of a COlor-Space-Time (COST) coding operation). The device in FIG. 28 (2800) illustrates an embodiment that comprises a fluidic channel (e.g. a microfluidic channel) 2801 where a sample (e.g., a particle or a cell) flows, channel wall 2808, a lens 2802, a series of optical filters 2803 and an optical detector (e.g. a PMT or photodetector) 2804. A sample (e.g. a particle or a cell) passing through a fluidic channel (e.g. a microfluidic channel) 2801 can emit light (e.g. fluorescent light) originating from positions A, B, C or D. The emitted light can pass through a lens 2802 and arrive at the image plane 2806 and contact one of the optical filters 2803 at the corresponding conjugate points indicated by A', B', C' and D'. Light paths 2807 are indicated by dashed or solid lines. For example light originating from position A will follow the indicated light path to A'. A lens, 2802, can transform light originating from a series of points within the sample path 2805 (located inside the fluidic channel) to the image plane 2806, through an array of optical filters 2803, to an optical detector 2804 (e.g. a PMT or photodetector). An array of optical filters can comprise a plurality of zones (e.g. color zones), where each zone in the array can transmit a subset of the light (e.g., a subset of a spectral content of electromagnetic radiation). Each optical filter within the array 2803 can have a different transmission spectrum. The energy distribution of light passing through any one of the filters or zones located at points A', B', C' or D' is defined by the spectral properties of the optical filter located at that point.

A light emitting sample (e.g. a particle or a cell) can transiently occupy positions A, B, C and D as it passes through the fluidic channel (e.g. a microfluidic channel) thereby generating multiple signals per sample. The waveform of these signals is determined by the transmission spectra of the optical filters and the characteristics of the sample. The combined optical signals of a sample can be digitally processed to determine the type of the particle and whether to sort the particle into a separate channel in a fluorescence-activated cell sorter system.

A fluidic channel (e.g. a microfluidic channel) can be part of a microfluidic device (e.g. a lab-on-a-chip) using sheath flow to confine the particles to the center of the fluidic channel. The microfluidic device can contain other features such as a sample (e.g. a cell or particle) sorting device. The sample sorting device can be downstream of the optical detection area and separate the sample of interest from the rest of the population. Such a microfluidic device can, in some embodiments, eliminate the generation of aerosols.

Figure 29:
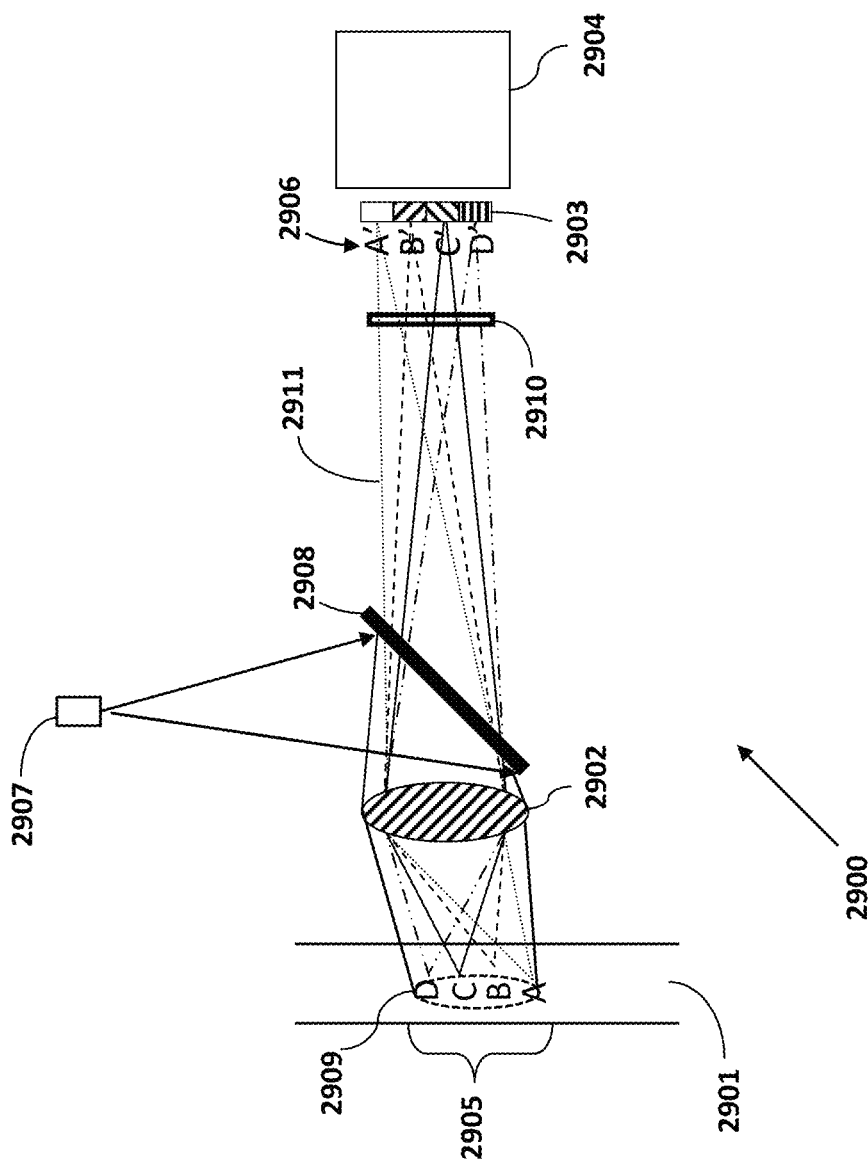
FIG. 29 is a schematic illustration showing an embodiment of a device used for flow cytometry or fluorescence-activated cell sorting (e.g. a non-limiting example of a COlor-Space-Time (COST) coding operation) illustrating a specific configuration of an excitation light source.

Shown in FIG. 29 is a schematic illustration showing another embodiment of a device used for flow cytometry or fluorescence-activated cell sorting (e.g. an example of a COlor-Space-Time (COST) coding operation). This device comprises a fluidic channel (e.g. a microfluidic channel) 2901, a lens 2902, a series of optical filters 2903 and an optical detector (e.g. a PMT or photodetector) 2904. Light paths 2911 are indicated by dashed or solid lines. Also shown is an excitation light source (e.g. a laser) 2907 directing light to a mirror 2908 (e.g. a dichroic mirror) which reflects the excitation light to a focal region 2909 within the fluidic channel (e.g. a microfluidic channel). The excitation light may contact a sample (e.g. a particle or a cell) located at any of the positions A, B, C or D within the sample path 2905. The excitation light originating from source 2907 can be focused by a lens 2902 to a desired focal region 2909. Also shown is an optical filter 2910 that can block the transmission of light of an undesired wavelength (e.g. light originating from the excitation light source 2907). Light (e.g. fluorescent light) emitted by a particle at positions A, B, C or D can pass through a lens 2902, a mirror 2908, a filter 2910, and contact one of the optical filters at the corresponding conjugate points on the image plane 2906 indicated by A', B', C' and D'. Light that is transmitted through one of the optical filters or color zones then proceeds on to the optical detector (e.g. a PMT or photodetector) 2904.

In an embodiment a mirror 2908 (e.g. a dichroic mirror) can be positioned at 45 degrees relative to the sample path 2905 or the image plane 2906. In some embodiments the mirror can be positioned between 30 and 60 degrees relative to the sample path 2905 or the image plane 2906. In some embodiments the mirror can be positioned between 10 and 80 degrees relative to the sample path 2905 or the image plane 2906. In some embodiments the mirror can be positioned at any angle that allows transmission of the excitation light source to a desired focal region 2909. The mirror 2908 can reflect light from an excitation light source (e.g. a laser) while allowing transmission of fluorescent light emitted from a sample. Since the intensity of the excitation laser beam can be many orders of magnitude greater than a fluorescent light signal, an optical filter 2910 can be introduced to block any stray light of the excitation laser from entering the array filter 2903 and optical detector (e.g. a PMT or photodetector) 2904. In some embodiments the optical filter 2910 can be a long pass filter or a precision optical notch filter.

Figure 30:
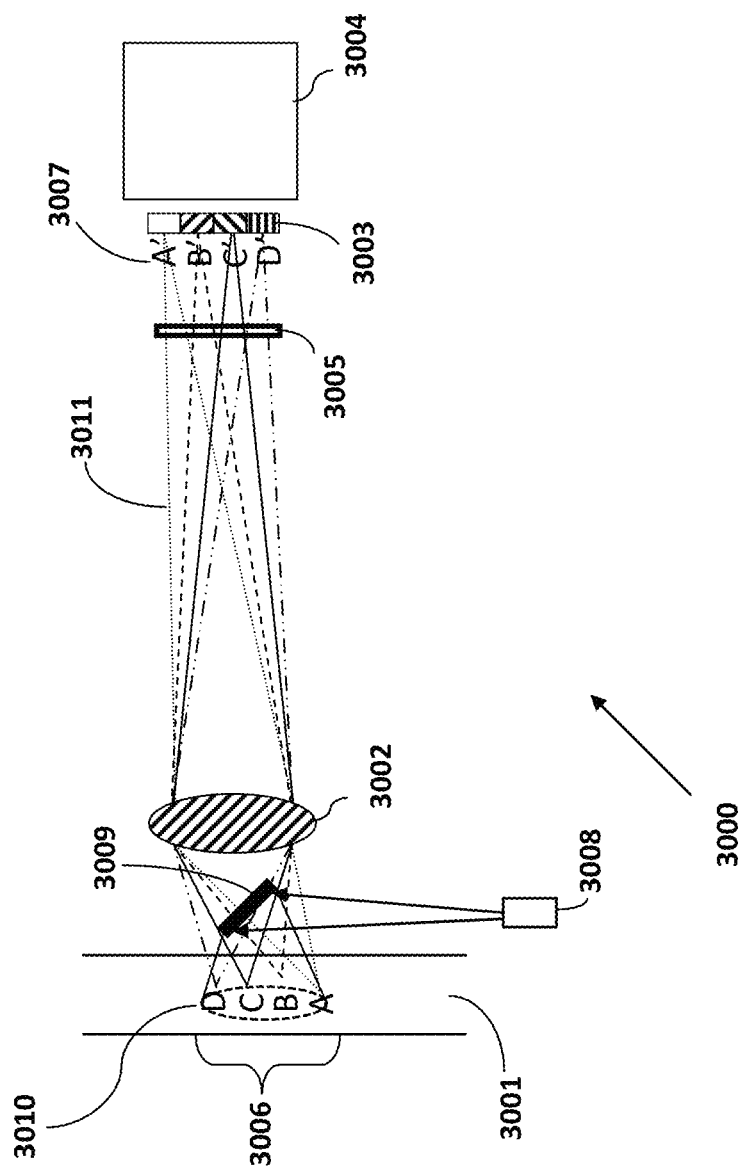
FIG. 30 is a schematic illustration showing one embodiment of a device used for flow cytometry or fluorescence-activated cell sorting (e.g. a non-limiting example of a COlor-Space-Time (COST) coding operation) illustrating a specific configuration of an excitation light source (e.g. a laser).

FIG. 30 illustrates another embodiment of a device 3000 that incorporates an excitation light source (e.g. a laser) 3008 and a mirror 3009. The device illustrated here comprises a fluidic channel (e.g. a microfluidic channel) 3001, a focal region 3010, a lens 3002, a filter 3005, a series of optical filters 3003 and an optical detector (e.g. a PMT or photodetector) 3004. The sample path 3006, sample positions A, B, C and D, light path 3011 and contact points A', B', C' and D' at the image plane 3007 are also shown.

The embodiment in FIG. 30 illustrates a mirror (e.g. a dichroic mirror) 3009 angled at about 45 degrees relative to the sample path 3006 or the image plane 3007. An excitation light source (e.g. a laser) 3008 directs light to the mirror 3009 which is reflected to the focal region 3010 located within the fluidic channel (e.g. a microfluidic channel). In this embodiment the mirror 3009 is located between the lens 3002 and the fluidic channel 3001. The mirror 3009 can reflect light from an excitation light source (e.g. a laser) while allowing transmission of fluorescent light emitted from a sample. An optical filter 3005 can be introduced to block any stray light of the excitation light source (e.g. a laser) from entering the array filter 3003 and optical detector (e.g. a PMT or photodetector) 3004.

One advantage of the flow cytometer device illustrated in FIG. 29 or FIG. 30 is a flexible method for introducing multiple excitation lasers for an increasing number of detection parameters. In some embodiments as illustrated in FIG. 29 or FIG. 30, multiple excitation light sources (e.g. multiple lasers) can be used. In such embodiments, the light source illustrated in FIG. 29 or FIG. 30 can be a combination of several lasers of different wavelengths (e.g. 405 nm, 488 nm, 532 nm, and 630 nm). In some embodiments, light from a light source (e.g. a laser) can emit from a single aperture after being conducted through a beam combiner or a wavelength demultiplexer.

In some embodiments a mirror (2908 or 3009) may reflect excitation light of all wavelengths to the focal region. In such an embodiment, the mirror may obstruct or block the transmission of light (e.g. fluorescent light) emitted from a sample. One solution to this potential problem is to position the mirror outside of the emission light path. Therefore in an embodiment a mirror (2908 or 3009) is positioned outside of the emission light path. Another solution is to reduce the size of the mirror so that the amount of emission light blocked (i.e. obstructed light) is reduced to an acceptable level. Therefore in another embodiment a mirror (2908 or 3009) is reduced in size so that the amount of obstructed light is reduced to an acceptable level. An acceptable level of obstructed light (e.g. fluorescent light emitted from the sample) can be between 0% and 50%. In some embodiments an acceptable level of obstructed light (e.g. fluorescent light emitted from the sample) is between 0% and 30%. In certain embodiments an acceptable level of obstructed light (e.g. fluorescent light emitted from the sample) is between 0% and 15%. For example, for a 50× objective lens with an 8 mm diameter aperture, a 1×2 mm mirror may block only about 3% of fluorescent light emitted from a particle.

Figure 31:
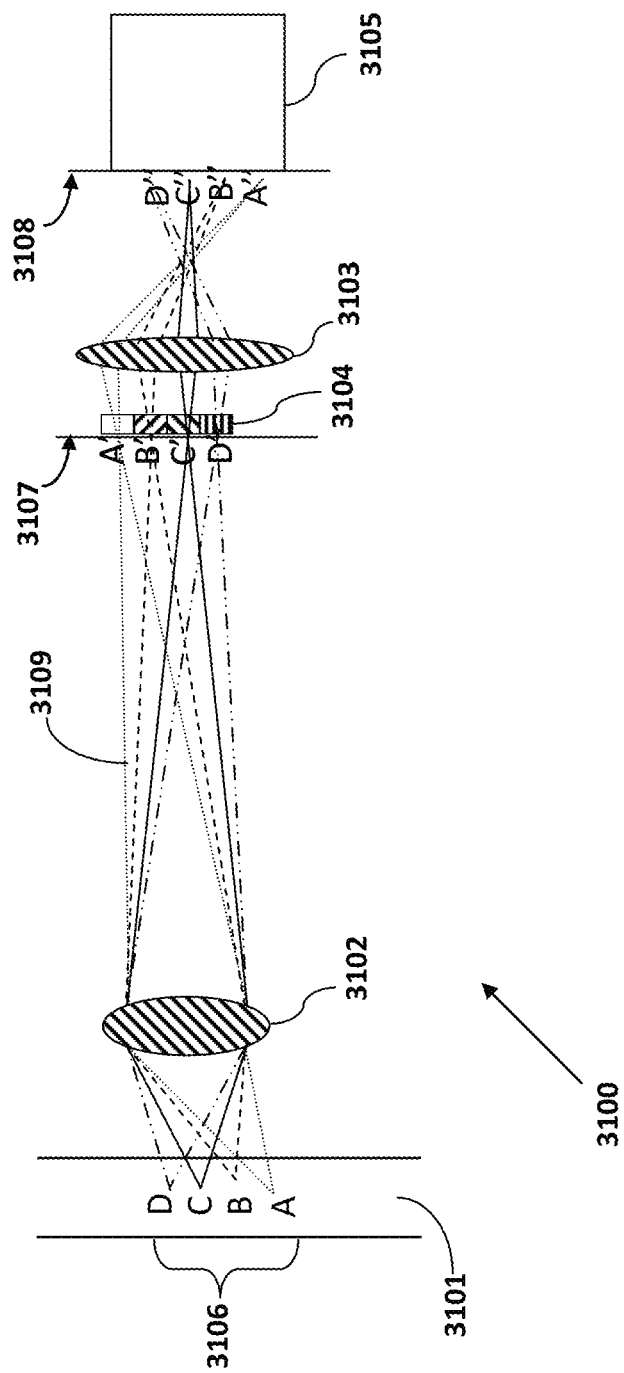
FIG. 31 is a schematic illustration showing one embodiment of a device used for flow cytometry or fluorescence-activated cell sorting (e.g. a non-limiting example of a COlor-Space-Time (COST) coding operation) comprising a lens located between an array of optical filters and an optical detector (e.g. a PMT or photodetector).

FIG. 31 illustrates another embodiment of a device 3100 that incorporates a lens 3103 positioned between an array of optical filters 3104 and the optical detector 3105 (e.g. a PMT or photodetector). As in the previous embodiment illustrated in FIG. 29, device 3100 comprises a fluidic channel (e.g. a microfluidic channel) 3101, a first lens 3102, a series of optical filters 3104 and an optical detector (e.g. a PMT or photodetector) 3105. The sample path 3106; sample positions A, B, C and D; light path 3109 and contact points A', B', C' and D' at the first image plane 3107 are also shown. A second lens 3103 can focus or concentrate light emanating from the first image plane 3107 at points A', B', C' and D' to corresponding points A", B", C" and D" on the second image plane 3108. Therefore light emanating from the sample at positions A, B, C and D can arrive at their corresponding positions A", B", C" and D" at the optical detector. In this embodiment, the number of filters (e.g. color zones) in the optical filter array is not limited by the size or shape of the photo sensitive area of the optical detector (e.g. a PMT or photodetector). In addition, the output waveform of the optical detector (e.g. a PMT or photodetector) is not affected by the non-uniformity of the optical detector (e.g. a PMT or photodetector) itself. Lens 3103 demagnifies images from filter 3104 onto image plane 3108 in some embodiments.

In some instances, as to be discussed herein, the number of fluorescent spectra the COST system can detect is related to the number of filters in an optical filter array. Decoupling the size of the array filter from the photosensitive area of the optical detector (e.g. a PMT or photodetector) can allow for detection of a larger number of parameters.

FIGS. 32A-32C illustrate an embodiment of a flow cytometer device 3200 that comprises a diffractive grating 3203 that can be used for the COST technique of sample (e.g. a particle or cell) detection. Device 3200 comprises a fluidic channel (e.g. a microfluidic channel) 3202, a lens 3201 (e.g. an objective lens), an optical detector (e.g. a PMT or photodetector) 3204, and a diffractive grating 3203 comprising a diffractive surface 3209. Diffractive grating 3203 can be any photo diffractive structure, such as a prism for example. As such, the diffractive element can be a transmissive or a reflective element. Also shown is a plate 3205 comprising a top surface 3206 and a channel 3207, where the channel 3207 includes an aperture at surface 3206. FIG. 32A, FIG. 32B and FIG. 32C differ with respect to the position of a light emitting sample (e.g. a particle or cell), where each sample position is represented by position A, B or C in the illustration. Each position A, B and C is located within the fluidic channel (e.g. a microfluidic channel) and is not part of the device.

A sample (e.g. a single particle or cell) that flows through a fluidic channel (e.g. a microfluidic channel) can transiently occupy positions A, B, or C and emanate light (e.g. fluorescent light). The light path emanating from each position A, B and C is illustrated by solid lines 3208. The position of a sample relative to the diffractive surface of the diffractive grating 3203 defines the wavelength range of light that passes through the aperture defined by channel 3207. For example, FIG. 32A illustrates that the optical detector (e.g. a PMT or photodetector) can detect red fluorescent light when the sample is at position A. FIG. 32B illustrates that the optical detector (e.g. a PMT or photodetector) can detect yellow fluorescent light when the sample is at position B and FIG. 32C illustrates that the optical detector (e.g. a PMT or photodetector) can detect blue fluorescent light when the sample is at position C. Thus, as a particle travels from position A to C, light detected by the photodetector is blue-shifted.

Therefore a sample that emits primarily blue light shows the strongest optical signal at position C, and then the signal diminishes as the particle travels further down the channel. The detected signal of a sample emitting primarily blue light will appear different than the signal from a different sample that emits primarily yellow or green light. Since each specific emission spectrum produces a corresponding output waveform, the output waveform can be treated as the distinguishing characteristics of that sample. Over the past years, due to the rapid development of high resolution, high sensitivity, and high frame-rate CCD and CMOS imagers, image-based cytometry has become a viable alternative to flow cytometry. In image-based cytometry, samples often are fixed to a glass slide or a surface and examined. The optical characteristics of a sample can be acquired by a photo detector, such as a CCD or CMOS imager, and then analyzed. Unlike flow cytometry that analyzes samples (e.g. cells or particles) in a serial manner, image-based cytometry often analyzes samples frame-by-frame in a parallel fashion. Multiple embodiments described herein can be applied to flow-based cytometry devices and to image-based cytometry devices.

Figure 33:
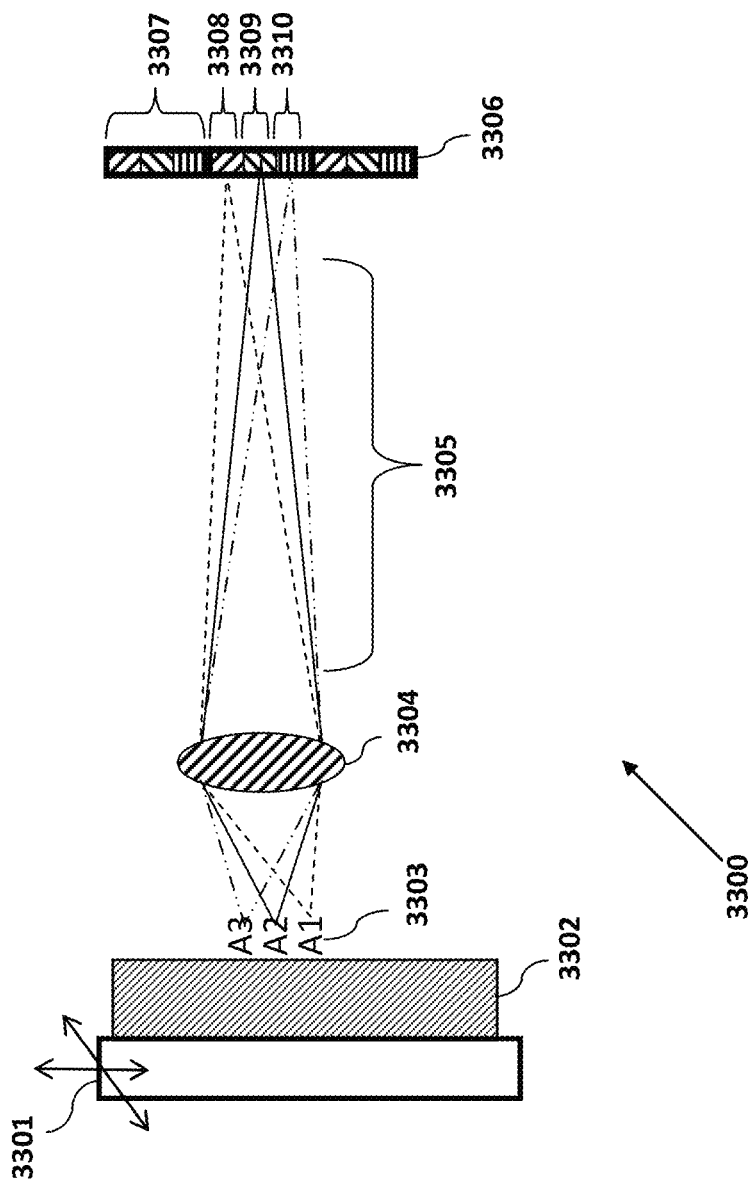
FIG. 33 is a schematic illustration of one embodiment of an image-based cytometer utilizing a non-limiting example of a COlor-Space-Time (COST) coding operation.

FIG. 33 is a schematic illustration of an image-based cytometer that can utilize COST techniques. Unlike a flow system where the particle traveling in the fluidic channel (e.g. a microfluidic channel) is detected sequentially by a single, highly sensitive optical detector, an image-based cytometer may use an array of detectors such as those found in CCD or CMOS devices with many (often several million) sensors (pixels) to detect a plurality of particles in parallel. Although the sensitivity of each sensor in a CCD or CMOS device may be lower than an optical detector (e.g. a PMT or photodetector), the detection time for static particles may be longer than for a flowing particle, thus compensating for the sensitivity difference between an imager and an optical detector, such as a optical detector (e.g. a PMT or photodetector). In FIG. 33 the image-based cytometer device 3300 comprises a moveable stage 3301, a lens 3304, and a CCD or CMOS imager 3306.

The imager may contain millions of pixels, and each of these pixels may be coated with an optical filter to be sensitive to red, green, and blue light, or R, G, B pixels. A set of RGB or RGBG pixels may form a unit 3307. Light emanating from a sample 3302 at position A1 may be projected through a lens 3304 and focused onto a red pixel on 3308. By altering the position of the stage 3301 to move the sample to position A2, the light of the same sample is focused onto a green pixel 3309, as indicated by the light path 3305. By altering the position of the stage 3301 further to move the sample to position A3, its light is focused onto a blue pixel 3310. By combining the three signals of the RGB pixels, one can determine the fluorescent properties of the sample.

Figure 34:
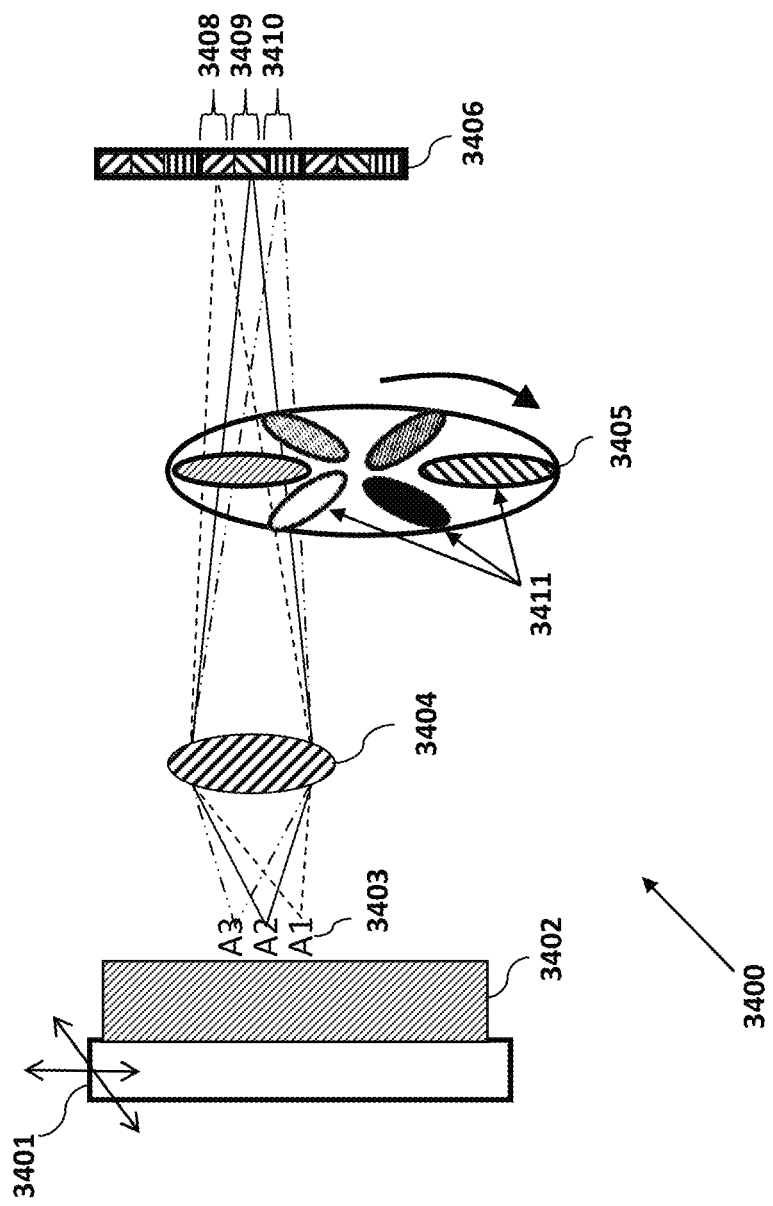
FIG. 34 is a schematic illustration of another embodiment of an image-based cytometer utilizing a non-limiting example of a COlor-Space-Time (COST) coding operation comprising a rotating wheel with a plurality of spectral filters.

The device in FIG. 33 essentially converts a standard fluorescent microscope into a cytometer system that can produce additional information about a sample. However, because conventional color imagers have only 3 colors (R, G, B), the number of detectable colors is limited. FIG. 34 illustrates a schematic of a device that can detect multiple colors.

Device 3400 is similar to device 3300 in that it comprises a moveable stage 3401, a lens 3404, and a CCD or CMOS imager 3406. The image-based cytometer device 3400 further comprises a rotating wheel 3405 with a plurality of spectral filters 3411 located between the lens 3404 and the imager 3406. For each position A1, A2, or A3, light is projected onto the red 3408, green 3409, and blue pixels 3410, respectively, similar to the device in FIG. 33. However, for the device shown in FIG. 34 the light also passes through a series of additional spectral filters 3411 on rotating wheel 3405 before reaching a pixel on the imager. In an embodiment, rotating wheel may contain 8 different spectral filters and therefore allow the detection of 24 different colors.

Figure 35:
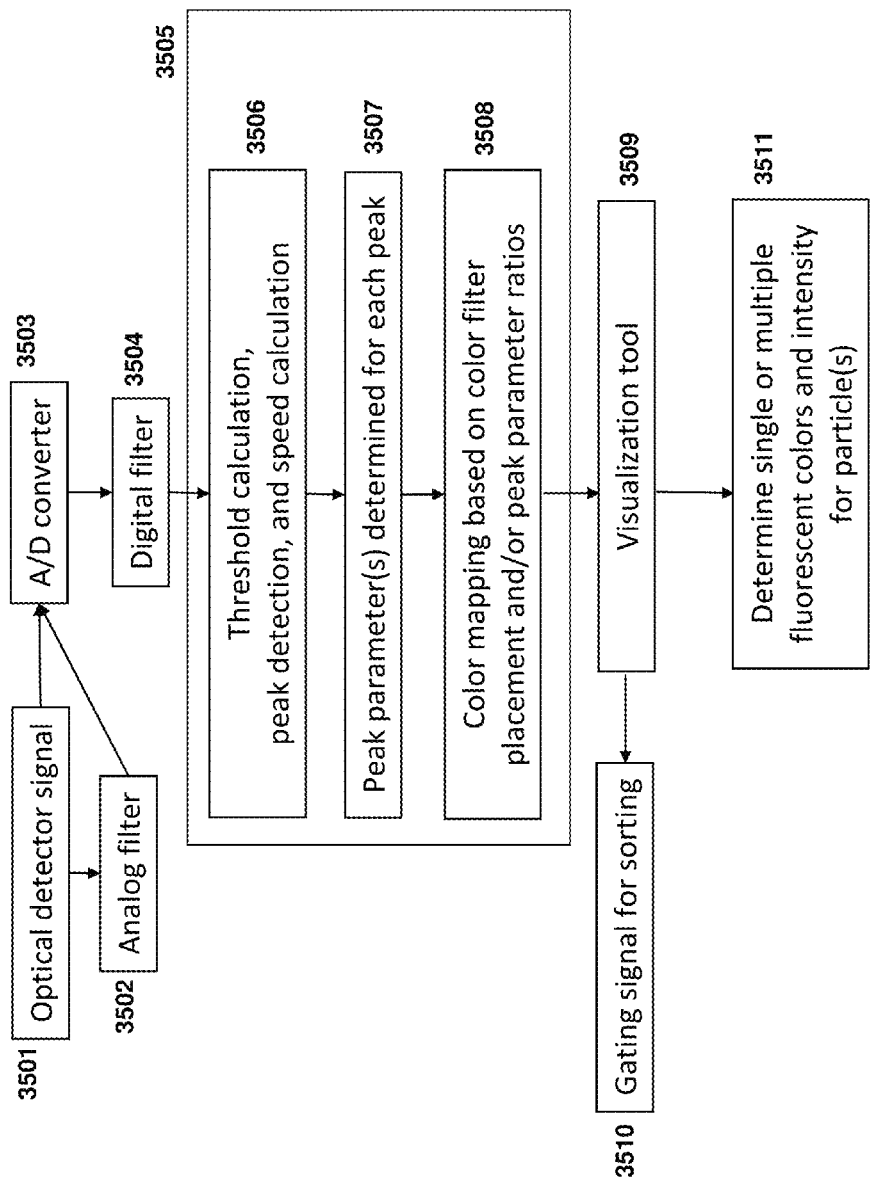
FIG. 35 is the block diagram for deciphering the fluorescent color of a sample from the COST signal.

FIG. 35 shows a block diagram rendition of a COST coding method embodiment that can be utilized for processing an optical detector (e.g. a PMT or photodetector) signal. When a particle passes through a detection zone, emitted light (e.g. fluorescence) can be detected by an optical detector (e.g. a PMT or photodetector). An optical detector (e.g. a PMT or photodetector) signal 3501 optionally can be passed through an analog filter 3502 to enhance the signal to noise ratio, or can be directly passed to an analog to digital converter (A/D converter) 3503. A digital filter 3504 downstream can further enhance the signal to noise ratio. The digital signal then can be processed by a computer processor (e.g. FPGA). Sub-processes 3506, 3507 and 3508 in process 3505 can be carried out by a computer processor. Sub-processes within process 3505 can be carried out as part of Windowed Peak Detection as shown in FIG. 10 in certain embodiments. During signal processing, signals can be processed and waveforms can be analyzed (e.g., all signals and all waveforms can be processed and analyzed). There sometimes is a threshold calculation phase in which a threshold level is set according to baseline noise (e.g., sub-process 3506). In a second phase, a previously calculated threshold can be used to analyze incoming signals for a waveform/COST signal. The speed of a particle also can be determined based on the location of the peaks (e.g., sub-process 3506). For peak detection, a waveform can be analyzed to identify peaks (e.g., sub-process 3506), and peak parameters (e.g., amplitude, time, area; sub-process 3507).

One or more peak parameters can be adjusted to compensate for an optical irregularity or signal irregularity at a suitable point in process 3505 (e.g., after sub-process 3507 and before sub-process 3508). As part of such adjustment, a calibration can be performed by passing a portion of a sample containing particles through the device configured with an all-pass filter in place of the color filter, where the all-pass filter includes zones that correspond to zones of a color filter. Another portion of the sample then can be passed through the device configured with the color filter, and signals detected from different zones of the color filter can be adjusted based on signals detected from corresponding zones of the all-pass filter.

The color corresponding to each peak can be mapped (e.g., sub-process 3508) based on the filter set used (e.g., color combinations using broad, continuous, or band pass filters among others). For example, a peak parameter can be mapped to a discrete band pass filter (i.e., color zone) in a color filter by placement on the color filter (e.g., sub-process 3508). A peak parameter sometimes is mapped to a zone in a color filter comprising zones of overlapping transparency according to one or more peak parameter ratios, which ratios provide for normalized peak parameters (sub-process 3508). Color mapping based on peak parameter ratios (normalized peak parameters) can be applicable to embodiments in which there is one fluorophore or quantum dot per particle (e.g., cell), and to embodiments in which there are multiple fluorophores or quantum dots per particle (e.g., cell), which are described in greater detail herein. Data can be further analyzed and visualized using a visualization tool 3509, which can reside on a personal computer (PC) to ultimately present and identify the fluorescent color(s) and fluorescent intensity emitted from a particle. A visualization tool often is a user interface that permits a user to analyze detection data and/or select certain parameters and functions of a flow cytometry device. A visualization tool sometimes allows a user to analyze detection data and identify particular particles or types of particles flowing through the device (e.g., 3511). A visualization tool sometimes allows a user to select parameters for sorting particular particles (e.g., 3510; select gating signal).

A COST coding process can be applied for detecting a plurality of spectra using a minimum number of optical detectors or imagers. Therefore, the designs proposed herein have fundamentally changed the scaling rule of flow cytometers which have traditionally required one optical detector for detection of each parameter (spectra).

As stated above, the COST coding process can distinguish a plurality of spectra from various kinds of cells or particles using a single optical detector. For some applications, the COST coding method can be applied in two general scenarios according to optical qualities of a sample (e.g., types of fluorophores effectively linked to cells (e.g., via antibodies)). In certain embodiments, a sample contains a mixture of cells or particles and each cell or particle is labeled by one single type of fluorescent dye or quantum dot. For instance, the sample may include a group of antibody-attached beads targeted to a group of specific antigens and each type of antibody-attached bead is uniquely identified by a specific type of fluorophore(s) or quantum dot(s). By detecting the fluorescence of fluorophore- or quantum dot-conjugated beads using a flow cytometer or a fluorescence-activated cell sorter to also isolate such beads, one can determine the presence and level of abundance of specific antigens. In such one-spectra-per-particle scenario, one can use a COST filer of four (4) spectra (e.g. white-red-green-blue (W/R/G/B)) to detect more than 20 spectra using the process outlined in FIG. 35. After the analog-to-digital (A/D) converter and removal of spurious optical detector noise and the thermal noise of electronics using digital filters, a peak detection or area detection method is used to identify or signify the signal level corresponding to the amount of light passing the filter of each spectra. Taking the ratio of the signal of each spectra and the signal passing the all-pass (white) filter, the "normalized" R- G- B-signals can be obtained for each sample. Each type of fluorophore or quantum dot possesses its unique ratios for the normalized R-, G-, B-signals. For any two different fluorophores or quantum dots, the amount of signal variation within the same fluorophore or quantum dot is significantly less than the separations among different fluorophores or quantum dots. As a result, one can apply the COST coding process to distinguish a plurality of spectrally distinct samples accurately.

In some embodiments, a single particle is spectrally distinguished by a plurality of fluorophores, and the COST coding process embodiment outlined in FIG. 35, for example, can be used to decipher the COST signal. With the assumption that there are N (e.g. 20) different types of fluorophores each having a specific fluorescence spectrum, according to the following relation in Equation (1), $t_{ij}$ is the transmission coefficient for jth fluorophore through the ith optical filter (e.g. j=1, 2 . . . N and i=1, 2, 3, 4); $C_j$ is the fluorescence intensity of jth fluorophore from the cell; and R, G, B, W represent the detected light intensity through the corresponding filters in the COST coded signal.

$$\begin{bmatrix} t_{11} & t_{12} & & t_{1,N-1} & t_{1N} \\ t_{21} & t_{22} & \cdots & t_{2,N-1} & t_{2N} \\ t_{31} & t_{42} & & t_{4,N-1} & t_{3N} \\ t_{41} & t_{42} & \cdots & t_{4,N-1} & t_{4N} \end{bmatrix} \begin{bmatrix} C_1 \\ C_2 \\ \vdots \\ C_N \end{bmatrix} = \begin{bmatrix} R \\ G \\ B \\ W \end{bmatrix}. \quad \text{Equation (1)}$$

The transmission coefficient for each of N fluorophores through the spectral filter can be calibrated as the spectral filter is designed. All coefficients $t_{ij}$'s therefore are known and can be stored in a data base. The linear system in Equation 1 contains four (4) independent equations, and four (4) fluorophores can be detected in a single particle out of many (e.g., 20) possible spectra. For instance, for a solution for [C1, C2, C3, C4, C5, . . . , C20] in Equation 1 of [0.5, 0.2, 0, 0, 0, . . . 0, 0, 0, 0.7, 1], it can be concluded that the particle contains four (4) types of fluorophores: C1, C2, C19, C20 with their intensity ratio being 5:2:7:10. In some instances, all C's may have non-zero values due to noise, and a threshold can be chosen to determine the presence of each type of fluorophore in a particle. The number of spectra in the spectral filter can be increased to detect more spectra co-exiting in a single particle. For example, by using an eight (8)-spectra filter, the COST coding process can detect as many as eight (8) fluorophores in one particle.

A continuously color graded spectral filter can be used in certain embodiments. Such a filter can be configured for a transmission spectrum continuously graded from red to blue color without any abrupt boundaries. Such a filter can comprise an all-pass (white) filter in the beginning and/or at the end of the filter to indicate the beginning and/or ending of the signal. In this manner, a COST signal becomes a continuous waveform (FIG. 36B) instead of a series of discrete peaks (FIG. 36A). One can digitally parse the COST signal into a series of spectral filters according to the transmission spectra at the given positions of the spectral filter. Since the number of filters can be digitally defined, the spectral filter can be divided into a plurality of spectra. A practical constraint of the number of spectra is the noise level that could corrode the signal when each spectral band is too narrow.

Such a dynamically adjusted spectral filter design, as shown by example in FIG. 36B, offers significant flexibility to a detection system. In immunology and cancer diagnosis, users often need to detect a very large number (e.g. 20) of spectra in one particle. One can purposely slow down the flow speed of a sample so that the COST signal covers a wide range in time domain, or in other words, the particle spends a longer time traveling through the detection zone. The longer signal duration allows users to divide the signal into a larger number of spectral divisions with adequate signal-to-noise ratio and enough number of sampling points over each spectral division. In other words, the COST coding technique not only simplifies the flow cytometer and FACS system by replacing multiple optical detectors with a single detector, but also offers the unique capability of trading flow speed (throughput) for the number of spectra the system can detect. Such tradeoffs can be dynamically adjusted by users according to their applications.

When the transmission characteristics of the filter changes continuously, users are given the flexibility of dividing the filter into any chosen number of units (e.g., FIG. 36B). If the particles under test are labeled with a large number of different fluorophores, the user may digitally divide the filter into a large number of units. On the other hand, if the application involves fewer different colors, then dividing the filter into fewer units is desirable for management of signal-to-noise ratio. To determine the speed of the particle, one can repeat a small section of the graded filter or add any "spectral signatures" in the filter (e.g. black out some small areas in the filter). When the signal waveform shows these signature patterns, the system can readily calculate the speed of the particle. This feature can also be used to verify if the actual flow velocity matches the set flow rate by users. This feature is useful since the set flow rate is based on an ideal laminar flow inside the channel. However, not all particles are located at the center of the channel and particle-particle interactions can push particles away from the center. Knowing the speed of each particle, besides the flow rate, helps enhance cell sorting efficiency.

In certain embodiments provided are flow cytometry devices comprising a microfluidic sensing channel through which sensing channel cells can flow and can be sensed, a branch downstream of the sensing channel, two or more microfluidic branch channels downstream of the branch, and an actuator configured for fluid communication with the branch and configured to drive cells, upon activation of the actuator, to one or more of the branch channels, which device is configured for a cell viability of greater than about 70.8% after cells are flowed through the device. Also provided in some embodiments are flow cytometry methods, comprising: (a) flowing cells through a microfluidic sensing channel, in which sensing channel cells can be sensed, in a flow cytometry device, which flow cytometry device comprises the sensing channel, a branch downstream of the sensing channel, two or more microfluidic branch channels downstream of the branch, and an actuator in fluid communication with the cells, which actuator is capable of driving cells to one of the branch channels upon activation of the actuator, and (b) sorting the cells flowing through the microfluidic channel to one of the branch channels, wherein cells that have passed through the device have a cell viability of greater than about 70.8%. Such microfluidic devices can include any suitable components described herein (e.g., color filter, detector and the like). Cell viability sometimes is about 71% or greater, about 75% or greater, about 80% or greater, about 85% or greater or about 90% or greater (e.g., about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater), which cell viability is determined after cells have flowed through the device. The actuator sometimes is a piezoelectric actuator (e.g., described herein). The actuator often is in fluid communication with the branch and/or cells in the device, often with substantially no air between the actuator and the branch and/or the cells. A flow cytometry device often does not generate droplets and often does not include an element that electrically charges cells, fluid in the device or droplets.

It has been determined that shear stress to cell membranes follows the following relation: $\tau = a\rho\upsilon f \tan(\theta)$, where "a" is the cell radius, "$\rho$" the average density, "$\upsilon$" the flow velocity, "f" the frequency of cell sorting actuator, and "$\theta$" the cell deflection angle by sorting. The product of flow speed and sorter frequency response (vf) determines the throughput, and it is found that the most effective approach of sorter design is to reduce the deflection angle "theta". Under the same transverse force by a piezoelectric actuator, a reduced theta design produces a more uniform transient velocity profile around the cell, thus yielding a significantly lower shear stress for enhanced cell viability. Neonatal rat primary cardiomyocytes sorted on a device comprising a piezoelectric actuator-driven sorter had a cell viability of 88.7%, compared to conventional sorting with a BD FACSAria system under gentle conditions (refrigerated, 20 psi, 100 μm nozzle) which sorted cells with a cell viability of only 70.8% (25% improved cell viability).

Figure 37:
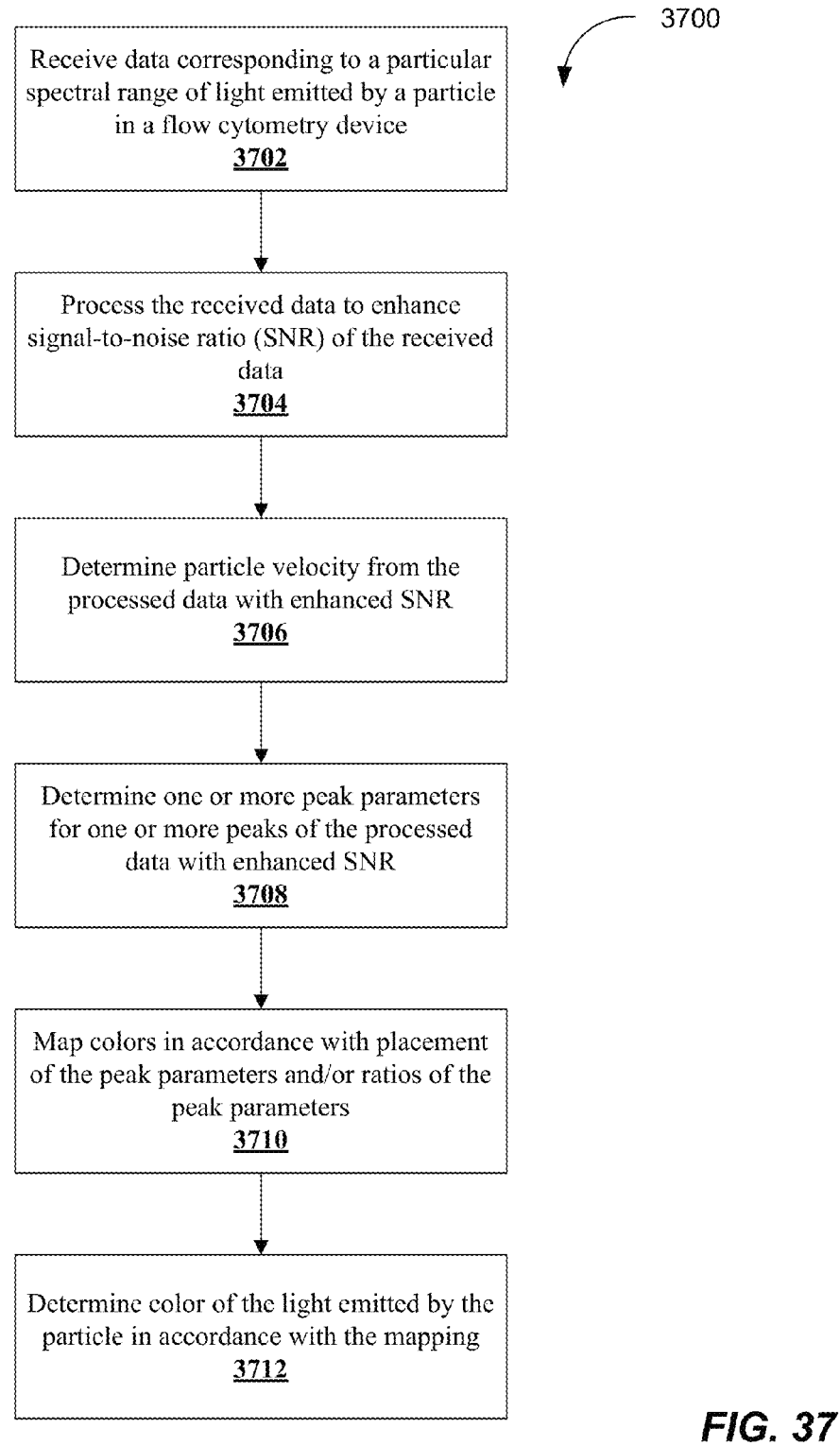
FIG. 37 illustrates a set of operations that can be carried out to analyze a particle in accordance with an exemplary embodiment.

FIG. 37 illustrates a set of operations 3700 that can be carried out to analyze a particle in accordance with an exemplary embodiment. In the exemplary operations 3700 the spectral characteristics of such as the color of light emitted by a particle is determined. The operations at 3702 includes receiving data corresponding to a particular spectral range of light emitted by a particle in a flow cytometry device. At 3704, the received data is processed to enhance signal-to-noise ratio (SNR) of the received data. At 3706, particle velocity is determined from the processed data with enhanced SNR. At 3708, one or more peak parameters for one or more peaks of the processed data with enhanced SNR is determined. At 3710, colors are mapped in accordance with placement of the peak parameters and/or ratios of the peak parameters, and at 3712, color of the light emitted by the particle is determined in accordance with the mapping of the colors.

Figure 38:
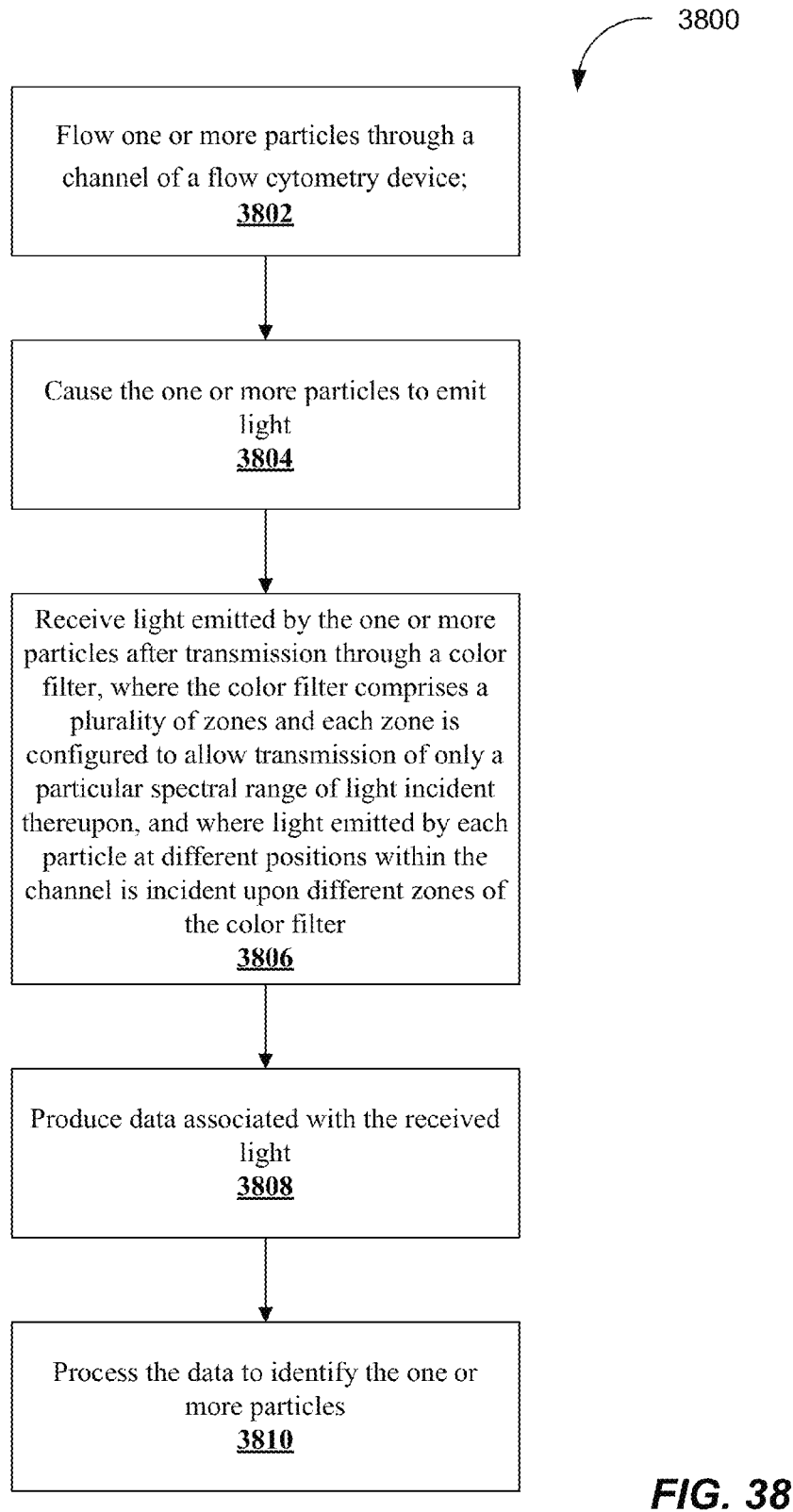
FIG. 38 illustrates a set of operations that can be carried out to analyze a particle in accordance with another exemplary embodiment.

FIG. 38 illustrates a set of operations 3800 that can be carried out to analyze a particle in accordance with an exemplary embodiment. In the exemplary operations 3800, the analysis of the particles includes identifying one or more particles. The operations at 3802 includes flowing one or more particles through a channel of a flow cytometry device. At 3804, one or more particles are cause to emit light. At 3806, the light emitted by the one or more particles are received after transmission of the light through a color filter. The color filter comprises a plurality of zones and each zone is configured to allow transmission of only a particular spectral range of light incident thereupon. In addition, light emitted by each particle at different positions within the channel is incident upon different zones of the color filter. At 3808, data associated with the received light is produced. For example, the operations at 3808 can include producing an analog signal corresponding to the received light, performing signal processing operations on the analog signal such as noise filtering, signal conditioning, error correction, conversion from analog to digital and the like. At 3810, the received data is processed to identify one or more particles.

Figure 39:
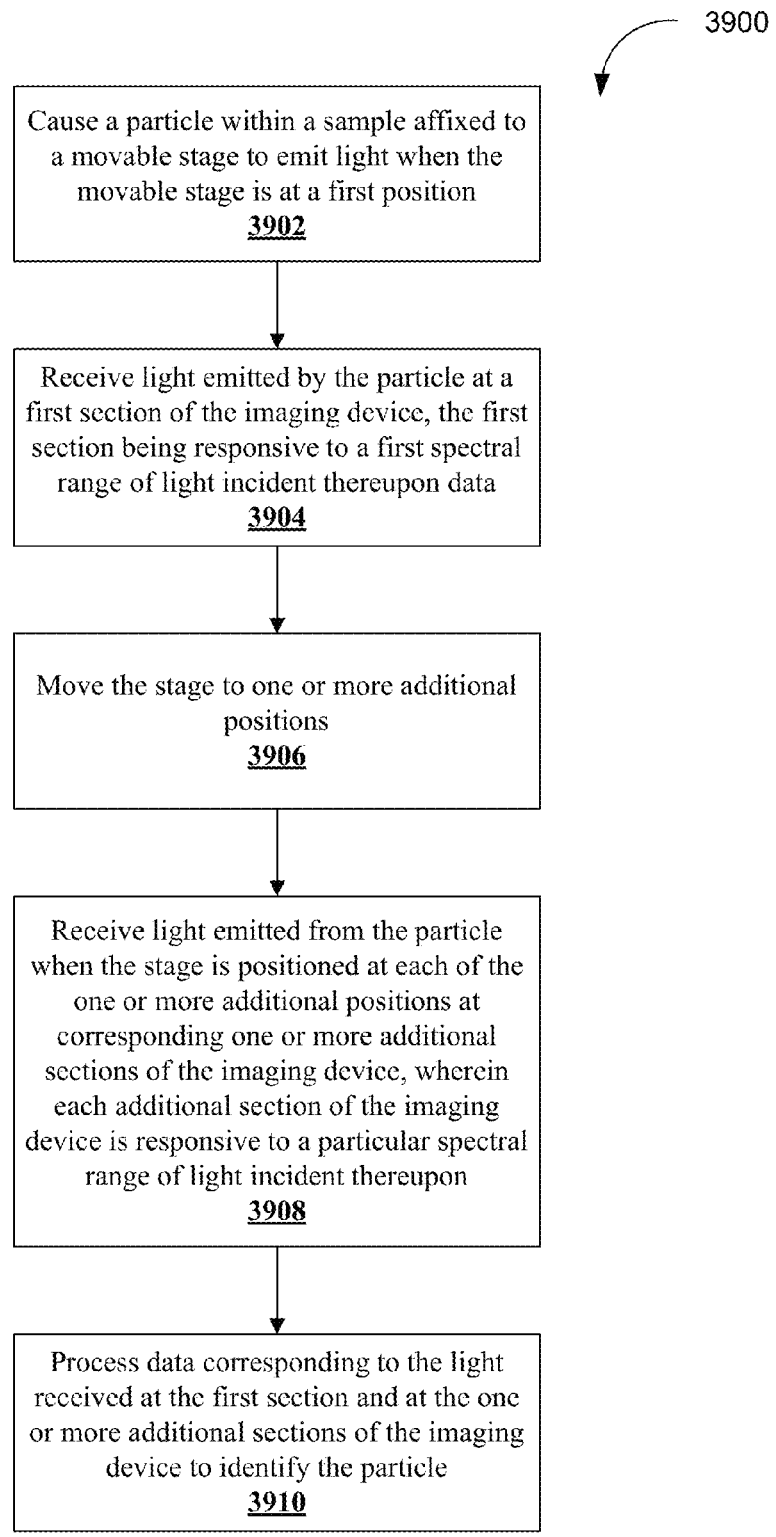
FIG. 39 illustrates a set of operations that can be carried out to analyze a particle in accordance with another exemplary embodiment.

FIG. 39 illustrates a set of operations 3900 that can be carried out to analyze a particle in accordance with an exemplary embodiment. In the exemplary operations 3900, the analysis of the particles includes identifying one or more particles. The operations at 3902 includes causing a particle within a sample affixed to a movable stage to emit light when the movable stage is at a first position. At 3904, the light emitted by the particle is received at a first section of the imaging device, where the first section is responsive to a first spectral range of light incident thereupon data. At 3906, the stage is moved to one or more additional positions. At 3908, the light emitted from the particle when the stage is positioned at each of the one or more additional positions is received at corresponding one or more additional sections of the imaging device. Each additional section of the imaging device is responsive to a particular spectral range of light incident thereupon. At 3910, data corresponding to the light received at the first section and at the one or more additional sections of the imaging device is processed to identify the particle.

Figure 40:
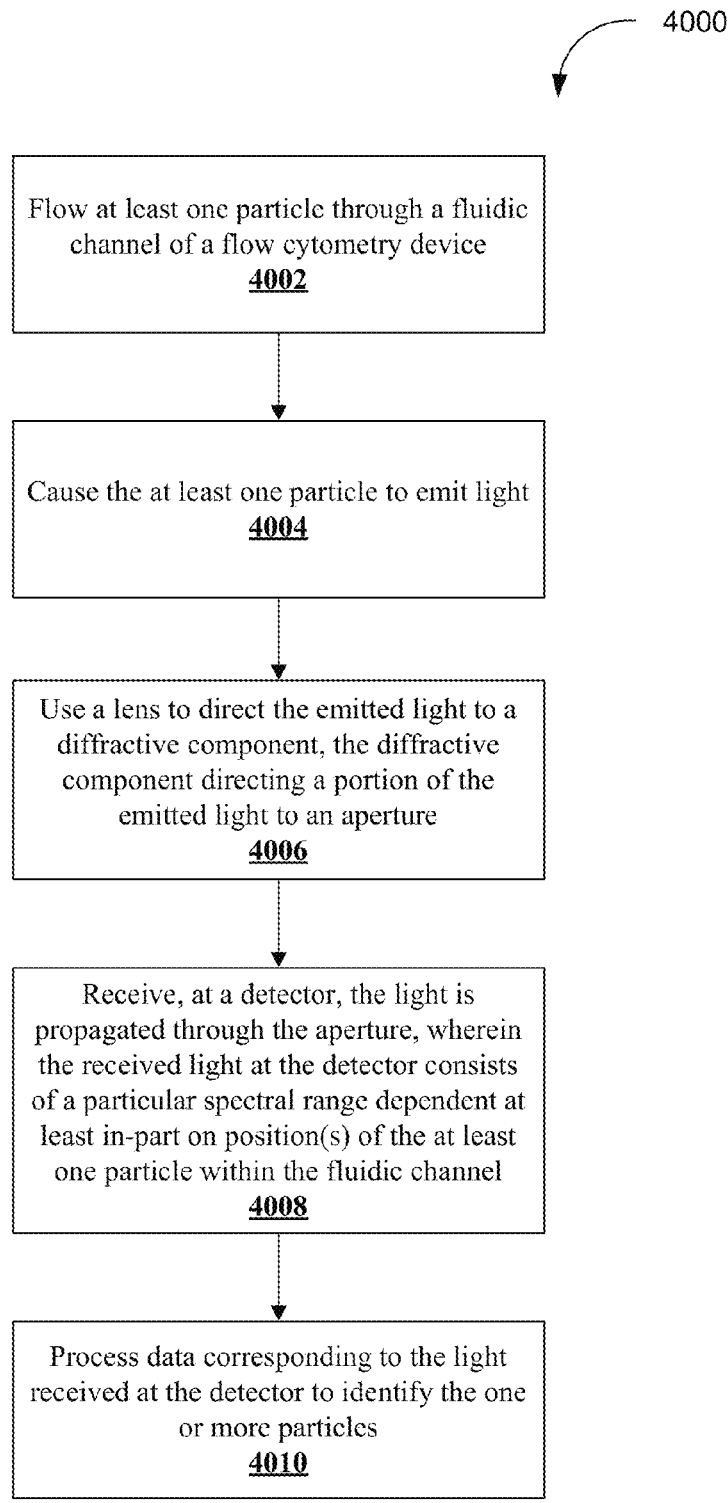
FIG. 40 illustrates a set of operations that can be carried out to analyze a particle in accordance with another exemplary embodiment.

FIG. 40 illustrates a set of operations 4000 that can be carried out to analyze a particle in accordance with an exemplary embodiment. In the exemplary operations 3900, the analysis of the particles includes identifying one or more particles. The operations at 4002 includes flowing at least one particle through a fluidic channel of a flow cytometry device. At 4004, at least one particle is caused to emit light. At 4006, a lens is used to direct the emitted light to a diffractive component, where the diffractive component directs a portion of the emitted light to an aperture. At 4008, the light that is propagated through the aperture is received at a detector, where the received light at the detector consists of a particular spectral range dependent at least in-part on position(s) of the at least one particle within the fluidic channel. At 4010, data corresponding to the light received at the detector is processed to identify the one or more particles.

It is understood that the various embodiments of the present application may be implemented individually, or collectively, in devices comprised of various hardware and/or software modules and components. In describing the disclosed embodiments, sometimes separate components have been illustrated as being configured to carry out one or more operations. It is understood, however, that two or more of such components can be combined together and/or each component may comprise sub-components that are not depicted. Further, the operations that are described in various figures of the present application are presented in a particular sequential order in order to facilitate understanding of the underlying concepts. It is understood, however, that such operations may be conducted in a different sequential order, and further, additional or fewer steps may be used to carry out the various disclosed operations.

Various embodiments described herein are described in the general context of methods or processes, some or part of which may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), Blu-ray Discs, etc. Therefore, the computer-readable media described in the present application include non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

For instance, in one exemplary embodiment, a computer program product, embodied on a computer-readable storage medium, is provided. The computer program product includes program code for receiving data corresponding to a particular spectral range of light emitted by a particle in a flow cytometry device, processing the received data to enhance signal-to-noise ratio (SNR) of the received data, determining particle velocity from the processed data with enhanced SNR, determining one or more peak parameters for one or more peaks of the processed data with enhanced SNR, mapping colors in accordance with placement of the peak parameters and/or ratios of the peak parameters, and determining color of the light emitted by the particle in accordance with the mapping.

The foregoing description of embodiments has been presented for purposes of illustration and description. The foregoing description is not intended to be exhaustive or to limit embodiments of the present invention to the precise form disclosed, and modifications and variations are possible in light of the above teachings or may be acquired from practice of various embodiments. The embodiments discussed herein were chosen and described in order to explain the principles and the nature of various embodiments and its practical application to enable one skilled in the art to utilize the present invention in various embodiments and with various modifications as are suited to the particular use contemplated. The features of the embodiments described herein may be combined in all possible combinations of methods, apparatus, modules, systems, and computer program products.

What is claimed is:

1. A flow cytometry device, comprising:
a channel capable of conducting a fluid containing at least one particle, the channel further capable of allowing light be transmitted to and from the channel;
a lens positioned between the channel and a single color filter and adapted to direct at least a portion of light transmitted from the channel to the single color filter, the single color filter having a continuously graded transmission spectrum from a first wavelength to a second wavelength without an abrupt boundary, the single color filter positioned at a stationary location with respect to the lens, the lens positioned to direct the light emanating from a corresponding range of positions of the at least one particle to impinge on only a portion of the single color filter as the at least one particle moves along the channel so that the light emanating from the particle at a first range of positions of the particle in the channel is directed by the lens to impinge on only a first portion of the single color filter, and as the particle transitions from the first range of positions to a second range of positions within the channel, the light emanating from the particle is directed to transition from falling on only the first portion to fall only on a second portion of the single color filter that allows transmission of light in a different spectral range of the transmission spectrum compared to the first portion of the single color filter; and
a detector configured to receive the light that is transmitted through the single color filter to produce detection signals in digital form; and
a processor implemented in electronic circuitry to receive the detection signals and configured to process the digital data of the detection signals to determine at least one characteristic of interest of the at least one particle, wherein the processor is further configured to filter the detection signals into a plurality of spectral bands within the transmission spectra of the single color filter, wherein a number of filtered spectral bands and spectral bandwidth of each filtered spectral band is changeable by the processor.

2. The flow cytometry device of claim 1, further comprising:
at least one light source positioned to direct light to the mirror;
one or more mirrors positioned to reflect the light from the light source(s) into the channel, wherein the one or more mirrors are substantially transparent to the light transmitted by the channel; and
an optical filter positioned between the lens and the detector and adapted to substantially block the light from the light source and to substantially transmit the light transmitted from the channel into the single color filter.

3. The flow cytometry device of claim 2, wherein at least one of the one or more mirrors is positioned between one of:
the lens and the detector, and
the lens and the channel.

4. The flow cytometry device of claim 1, further comprising an additional lens positioned between the color filter and the detector.

5. The flow cytometry device of claim 1, wherein each portion of the single color filter allows transmission of a spectral range of light that is non-overlapping with spectral ranges allowed to be transmitted by all other portions.

6. The flow cytometry device of claim 1, wherein at least one portion of the single color filter is adapted to allow transmission of a spectral range of light that is overlapping with transmission spectral range of at least one other portion.

7. An imaging device, comprising:
a stage configured to move in one or more dimensions and configured to receive an object for imaging, wherein at least a portion of the object is capable of transmitting light; and
a lens positioned between the stage and an image sensor and adapted to direct the light emitted by the at least a portion of the object to the image sensor,
wherein the image sensor comprises a plurality of light sensing elements arranged as a plurality of sensing element subsets, each sensing element subset being responsive to a particular spectral range of light incident thereupon, a single continuously graded color filter positioned between the lens and the image sensor, the single continuously graded color filter having a continuously graded transmission spectrum from a first wavelength to a second wavelength without an abrupt boundary, and wherein the image sensor is aligned with the lens and the object so as to receive, at a first subset of the sensing elements, a first spectral range of light emitted by the object when the stage positions the object at a first position, and to receive a second spectral range of light emitted by the object at a second subset of sensing elements when the stage positions the object at a second position, the imaging device further comprising a processor implemented in electronic circuitry to receive detection signals produced by the image sensor and configured to process the detection signals to determine at least one characteristic of interest of the object, wherein the processor is further configured to filter the detection signals into a plurality of spectral bands within the transmission spectra of the single continuously graded color filter, wherein a number of filtered spectral bands and spectral bandwidth of each filtered spectral band is changeable by the processor.

8. The imaging device of claim 7, wherein each portion of the color filter is adapted to allow transmission of only a particular spectral range of light.

9. A method for identifying one or more particles by flow cytometry, comprising:
  flowing one or more particles through a channel of a flow cytometry device;
  causing the one or more particles to emit light;
  receiving light emitted by the one or more particles after transmission through a lens that directs the light to a single color filter, wherein the single color filter comprises a plurality of contiguously graded transmission spectrum from a first wavelength to a second wavelength without an abrupt boundary, and wherein the single color filter is positioned at a stationary location with respect to the lens, the lens positioned to direct the light emanating from a corresponding range of positions of each particle to impinge on only a portion of the single color filter as each particle moves along the channel so that the light emanating from the particle at a first range of positions of the particle in the channel is directed by the lens to impinge on only a first portion of the single color filter, and as the particle transitions from the first range of positions to a second range of positions within the channel, the light emanating from the particle is directed to transition from falling on only the first portion to fall only on a second portion of the single color filter that allows transmission of light in a different spectral range of the transmission spectrum compared to the first portion of the single color filter;
  producing digital data associated with the received light; and
  processing the digital data to identify the one or more particles, wherein processing the digital data comprises selecting a plurality of dynamically selectable spectral bands, and filtering the digital data into the plurality of spectral bands within the transmission spectra of the single color filter, wherein a number of selected spectral bands and a spectral bandwidth of each selected spectral band is changeable within the spectra of the single color filter.

10. The method of claim 9, further comprising determining velocity of the one or more particles flowing through the channel.

11. The method of claim 10, further comprising directing at least one of the one or more particles through a channel branch based on identity and velocity of the at least one of the one or more particles.

12. The method of claim 9, wherein the one or more particles are identified based on at least a color of the received light.

13. The method of claim 9, wherein a first particle of the one or more particles emits light at a different spectral range than a second particle of the one or more particles.

14. The method of claim 9, wherein
  the received light emitted by the one or more particles corresponds to a continuous waveform.

15. The method of claim 14, further comprising modifying velocity of the one or more particles flowing through the channel to facilitate parsing of the data into a particular number of spectral bands.

16. The method of claim 15, wherein at least one of the velocity and the number of spectral bands are specified by a user of the flow cytometry device.

17. A method for identifying a particle by an imaging device, comprising:
  causing a particle within a sample affixed to a movable stage to emit light when the movable stage is at a first position;
  receiving light emitted by the particle at a first section of the imaging device, the first section being responsive to a first spectral range of light incident thereupon;
  using a lens to direct the light emitted by the particle onto an image sensor;
  using a single color filter positioned between the lens and image sensor, the single continuously graded color filter having a continuously graded transmission spectrum from a first wavelength to a second wavelength without an abrupt boundary;
  moving the stage to one or more additional positions;
  receiving light emitted from the particle when the stage is positioned at each of the one or more additional positions at corresponding one or more additional sections of the imaging device, wherein each additional section of the imaging device is responsive to a particular spectral range of light incident thereupon;
  processing data corresponding to the light received at the first section and at the one or more additional sections of the imaging device to identify the particle, wherein the processing comprises selecting a plurality of dynamically selectable spectral bands, and filtering the data into the plurality of spectral bands within the transmission spectra of the single color filter, wherein a number of selected spectral bands and a spectral bandwidth of each selected spectral band is a changeable within the spectra of the single color filter.

* * * * *